United States Patent
Rosenstock et al.

(10) Patent No.: US 6,458,121 B1
(45) Date of Patent: Oct. 1, 2002

(54) APPARATUS FOR ATHERMAPEUTIC MEDICAL TREATMENTS

(75) Inventors: Yehuda Rosenstock, Freeport; Samuel Sadinsky, Kings Park; David M. Ross, Great Neck, all of NY (US)

(73) Assignee: Diapulse Corporation of America, Great Neck, NY (US)

( * ) Notice: Subject to any disclaimer, the term of this patent is extended or adjusted under 35 U.S.C. 154(b) by 0 days.

(21) Appl. No.: 08/618,409

(22) Filed: Mar. 19, 1996

(51) Int. Cl.$^7$ ............................................. A61B 11/39
(52) U.S. Cl. .......................... 606/34; 606/41; 607/115
(58) Field of Search .................... 606/34, 41, 42; 607/115, 100–102

(56) References Cited

U.S. PATENT DOCUMENTS

| | | | | |
|---|---|---|---|---|
| 5,370,645 A | * | 12/1994 | Klicek et al. ................. | 606/34 |
| 5,406,503 A | * | 4/1995 | Williams, Jr. et al. ........ | 606/34 |
| 5,540,681 A | * | 7/1996 | Strul et al. .................... | 606/34 |
| 5,817,092 A | * | 10/1998 | Behl ........................... | 606/41 |
| 5,849,010 A | * | 12/1998 | Wurzer et al. ................ | 606/34 |
| 5,931,835 A | * | 8/1999 | Mackey ....................... | 606/34 |
| 5,957,969 A | * | 9/1999 | Warner et al. ................ | 606/34 |

* cited by examiner

Primary Examiner—Robert L. Nasser
(74) Attorney, Agent, or Firm—Myron Amer P.C.

(57) ABSTRACT

Apparatus is disclosed herein which is capable of administering DIAPULSE® treatments, and also capable of applying electromagnetic energy to a treatment area for modified DIAPULSE treatments and for new applications, both thermal and non-thermal, including research. The apparatus provides: more precise control of treatment parameters, including burst repetition rate, power level, and treatment duration, using a minimal number of hardware components; dynamic adjustment of power radiated to a treatment area to a selected power level; the capability of varying treatment parameters in software beyond the variations possible in the earlier DIAPULSE® apparatus; the automatic creation and updating of a patient file which logs treatment parameters and other information, and the ability to access, upload and down load the patient file and information therein; and the reduction of power consumption and power dissipation by and in the improved apparatus. The apparatus includes a power monitor and a processor which cooperate to provide closed loop control of the power of the RF pulses output by the apparatus, and "fail-safe" control of the apparatus to prevent the apparatus from radiating pulses at power levels above a given maximum and upon detection by the apparatus of an abnormal condition.

1 Claim, 11 Drawing Sheets

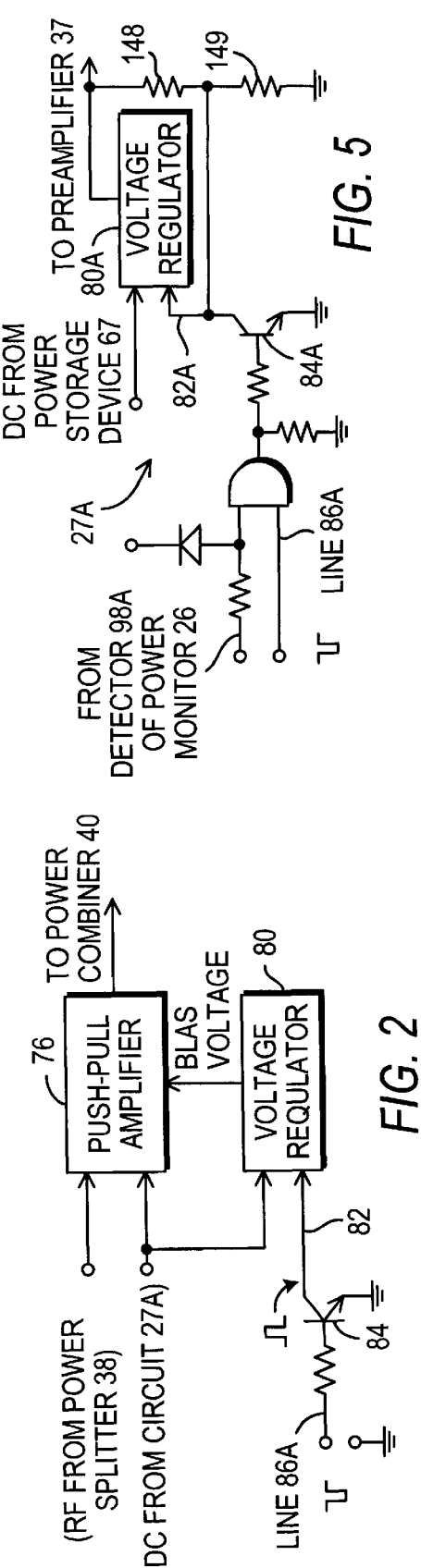
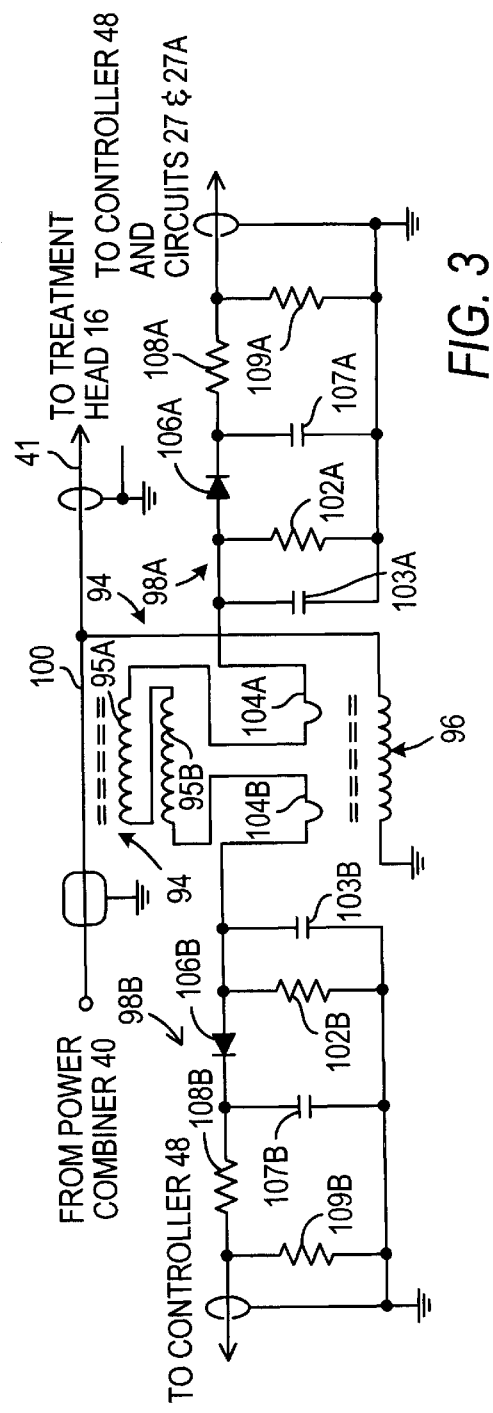
FIG. 5
FIG. 2
FIG. 3

ROOM/BED 05-09-1995, 16:24:02, JOHN DOE, 99999, NORTH SHORE, 25 , M, 4,

| Date | Time | Col3 | Col4 | Col5 |
|---|---|---|---|---|
| 05-09-1995 | 16:25:00 | 600 | 6 | 1 |
| 05-09-1995 | 16:25:45 | 80 | 2 | 1 |
| 05-09-1995 | 16:26:18 | 80 | 2 | 1 |
| 05-09-1995 | 16:29:13 | 80 | 2 | 2 |
| 05-09-1995 | 16:29:41 | 80 | 2 | 1 |
| 05-10-1995 | 12:38:42 | 600 | 6 | 1 |
| 05-10-1995 | 12:40:27 | 600 | 6 | 1 |
| 05-11-1995 | 09:47:16 | 600 | 6 | 9 |
| 05-11-1995 | 09:48:42 | 600 | 6 | 1 |
| 05-11-1995 | 09:50:13 | 600 | 6 | 1 |
| 05-11-1995 | 09:52:41 | 600 | 6 | 2 |
| 05-11-1995 | 10:14:55 | 600 | 6 | 15 |
| 05-11-1995 | 10:35:13 | 600 | 6 | 17 |
| 05-11-1995 | 12:33:51 | 160 | 4 | 1 |
| 05-11-1995 | 12:36:38 | 160 | 4 | 1 |
| 05-11-1995 | 12:42:08 | 160 | 4 | 2 |
| 05-11-1995 | 12:42:15 | 160 | 4 | 1 |
| 05-11-1995 | 12:52:06 | 600 | 5 | 1 |
| 05-11-1995 | 13:18:34 | 600 | 6 | 1 |
| 05-11-1995 | 14:07:05 | 600 | 6 | 42 |
| 05-11-1995 | 17:05:09 | 400 | 6 | 2 |
| 05-12-1995 | 10:34:45 | 600 | 6 | 1 |
| 05-12-1995 | 16:02:01 | 300 | 3 | 1 |
| 05-12-1995 | 16:02:11 | 300 | 3 | 1 |
| 05-12-1995 | 16:02:57 | 300 | 6 | 1 |
| 05-12-1995 | 17:09:16 | 500 | 4 | 1 |
| 05-12-1995 | 18:00:03 | 300 | 6 | 1 |
| 05-12-1995 | 18:02:04 | 600 | 5 | 1 |
| 05-12-1995 | 18:11:14 | 600 | 5 | 1 |
| 05-12-1995 | 18:24:00 | 600 | 6 | 1 |
| 05-12-1995 | 19:07:59 | 600 | 6 | 1 |
| 05-12-1995 | 19:10:07 | 600 | 6 | 1 |
| 05-12-1995 | 20:14:53 | 600 | 6 | 60 |
| 05-13-1995 | 15:04:41 | 600 | 6 | 25 |
| 05-13-1995 | 15:19:58 | 80 | 6 | 1 |
| 05-13-1995 | 15:20:06 | 80 | 6 | 1 |
| 05-13-1995 | 15:20:12 | 80 | 6 | 1 |
| 05-13-1995 | 15:20:18 | 80 | 6 | 1 |
| 05-13-1995 | 15:20:34 | 80 | 6 | 1 |

APPARATUS FOR ATHERMAPEUTIC MEDICAL TREATMENTS

COPYRIGHT NOTICE

A portion of the disclosure of this patent document contains material which is subject to copyright protection. The copyright owner has no objection to the facsimile reproduction by anyone of the patent disclosure, as it appears in the Patent and Trademark Office public patent files or records, but otherwise reserves all copyright rights whatsoever.

BACKGROUND OF THE INVENTION

The invention disclosed herein relates to an apparatus for administering electromagnetic energy to tissue for medical and research purposes. In particular, the present invention relates to such apparatus which administers the electromagnetic energy athermapeutically (non-thermally). Also, the invention relates to a method for providing and updating patient and research files which store information regarding the treatment parameters and the patient or research project.

Prior art apparatus for administering high frequency electromagnetic energy athermapeutically has been available for many years from Diapulse Corporation of America, of Great Neck, N.Y. Such apparatus, referred to by Diapulse Corporation of America as the "Diapulse Wound Treatment System"™ ("DWTS"™), and referred to herein as "DIAPULSE® apparatus," has been used extensively for the athermapeutic treatment of damaged tissue, and treatments using such apparatus have come to be identified as "DIAPULSE® treatments" or "DIAPULSE® Therapy". The following patents relate to earlier DIAPULSE® apparatus, including the treatment head thereof: U.S. Pat. Nos. 2,276,994; 2,276,995; 2,276,996; 3,043,310; 3,181,535; 3,464,010; 3,670,737 and 4,226,246; Canadian Patent No. 679,371; and French Patent No. 2,301,965. The entire disclosures of all of those patents are hereby incorporated herein by reference.

DIAPULSE® apparatus available from Diapulse® Corporation of America generates and delivers short bursts of high peak power RF electromagnetic pulses to an area to be treated in or on the patient's body without causing any significant rise in temperature in the treated area. A DIAPULSE® treatment applies the energy to the desired treatment area by radiating it from a treatment head placed adjacent the treatment area, either in direct contact with or in close proximity to the treatment area. The specific operating parameters of DIAPULSE® treatments are: radiation of RF electromagnetic pulses of 27.12 MHz (11 meter band) in short, squared bursts of 65 μsec., at selectable burst repetition rates between 80 to 600 bursts per second (duty cycle between 0.5% and 3.9%), at selectable peak powers between about 300 and about 1000 watts, providing average powers of from about 1.5 W to about 38 W. Pulse frequencies of 0.5 of 27.12 Mhz and 1.5 of 27.12 Mhz may also be used, i.e. pulse frequencies of 13.56 MHz and 40.68 Mhz, respectively. The treatment head size and the treatment area size are such, that with the parameters given above, the DIAPULSE® treatment is athermapeutic, and the pulsed energy delivered to the treatment area is "non-thermal" in a medical sense.

The efficacy of the high amplitude, short duration electromagnetic pulses applied in DIAPULSE® treatments resides in the ability of these pulses to affect the electrical state of living cells, rather than to generate heat. As understood, these high amplitude, short duration electromagnetic pulses achieve beneficial effects by accelerating the return of the electrical state of damaged tissue to its normal condition, thus hastening the resulting electrochemical and chemical responses, and increasing blood flow, which are involved in healing and pain relief. Scientific blind, double blind and control studies have proved that DIAPULSE® treatments accelerate the healing of tissue damaged by burn, laceration, contusion, abrasion and surgical intervention, reduce edema, erythema, and inflammation, and prevent and relieve acute and chronic pain. These studies also show DIAPULSE® treatments to be effective in the treatment of a wide range of specific applications from the treatment of head injuries, pressure ulcers and acute and chronic wounds (due to surgery and otherwise) to the treatment of ankle sprains. See, for example, Ross, Jesse, Utilization of Pulsed High Peak Power Electromagnetic Energy (Diapulse Therapy) to Accelerate Healing Processes, Digest International Symposium, IEEE Antennas and Propagation Society, Stanford University, Jun. 20–22, 1977, pp. 146–149; Ross, Jesse, Results, Theories, and Concepts Concerning the Beneficial Effects of Pulsed High Peak Power Electromagnetic Energy (Diapulse® Therapy) in Accelerating the Inflammatory Process and Wound healing, presented at The Bioelectromagnetics Society 3rd Annual Conference, Washington, D.C., Aug. 9–12, 1981; Ross, Jesse Evolution, Prevention and Relief of Acute and Chronic Pain with the Application of Diapulse® Therapy (Pulse of High Peak Power Electromagnetic Energy), published in Schemerz, 1/1984, pp. 9–16; Ross, Jesse, Biological Effects of pulsed Peak Power Electromagnetic Energy using Diapulse®, published in Emerging Electromagnetic Medicine, O'Connor, M. E., Bentall, R. H. C., Monohan, J. C., editors, Springer-Verlag, 1990, pp. 269–281; Itoh, Masayoshi et al., Accelerating Wound Healing of pressure Ulcers by Pulsed High Peak Power Electromagnetic Energy (Diapulse®), Decubitus, 4(1):24:February 1991; Pennington, Gerard M., et al., Pulsed, Non-Thermal, High Frequency Electromagnetic Energy (Diapulse®) in the Treatment of Grade I and Grade II Ankle Sprains, Military Medicine, Vol. 158, No. 2, February 1993; Sambasivan, M., Pulsed Electromagnetic Field in Management of Head Injuries Neurology India, (1993) 41 (Suppl.), pp. 56–59; Salzberg, Andrew C. et al., The Effects of Non-Thermal Pulsed Electromagnetic Energy (Diapulse®) on Wound Healing of Pressure Ulcers in Spinal Cord-Injured Patients: A Randomized Double-Blind Study, Wounds, Vol. 7, No. 1, January/February 1995, pp. 11–16; Tung, Shirley et al., The Application of Diapulse® in the Treatment of Decubitus Ulcers: Case Reports, Contemporary Surgery, Vol. 47, No. 1, July 1995, pp. 27–32.

There is a need, however, for an improved apparatus capable of administering DIAPULSE® treatments, and also capable of applying electromagnetic energy to a treatment area for modified DIAPULSE® treatments and for new applications, both thermal and non-thermal, including research.

SUMMARY OF THE INVENTION

It is an object of the invention disclosed herein to provide an improved apparatus for the application of electromagnetic energy for medical treatments and/or research.

It is another object of the invention to provide such treatment apparatus with improved and/or expanded control of treatment parameters.

It is another object of the invention to more precisely control parameters of medical and/or research treatments in an apparatus which delivers high frequency electromagnetic pulses to treatment areas; other objects are to do so using a minimal number of components, and to be able to vary such treatment parameters in software, in response to settings input by a user or in response to settings stored in the apparatus. Another object is to vary the settings stored in the apparatus at the site of the apparatus and/or remotely.

It is another object of the invention to control more closely the power output of high frequency electromagnetic pulses radiated by apparatus for conducting medical treatments and/or research. Another object is to provide for "fail-safe" operation in the sense that such apparatus does not radiate the electromagnetic pulses at unsafe power levels, or for time periods sustained for longer than the time periods of the bursts, or when the apparatus is not set to radiate the pulses.

It is another object of the invention to automatically store in apparatus for conducting medical treatments and/or research (or apparatus coupled thereto) treatment parameters and other information for each patient or research project and for each treatment session. Another object is to process and/or print these parameters and information either directly from or by the apparatus, or after transfer of the parameters and information to other apparatus or storage devices. Another object is to be able to transfer such information, including information which controls the treatment parameters for a particular patient or treatment session, into and out of such apparatus through a communication link from and/or to a remotely located apparatus. Another object is to provide multi-media capability for such apparatus which includes at least storing and/or displaying of images.

It is another object of the invention to provide some indication or alarm (e.g., audio, visual or both, and/or an electronic record), when the treatment head of a medical treatment apparatus is moved out of the position it was initially set in (or a patient moves relative to the treatment head).

It is another object of the invention to provide a transportable apparatus for conducting medical treatments and/or research in which treatment parameters may be changeably entered at a given site, and the treatment defined by the entered parameters carried out by the apparatus at another site.

It is another object of the invention to reduce power consumption and/or power dissipation in apparatus for generating and delivering bursts of high peak power electromagnetic RF pulses.

A more specific object is to improve the prior DIAPULSE® apparatus in one or more, and preferably all, of the following ways, while at the same time retaining the specific operating parameters described above of DIAPULSE® treatments:

more precise control of treatment parameters, including burst repetition rate, power level, and treatment duration, using a minimal number of hardware components;

dynamic adjustment of power radiated to a treatment area to a selected power level;

the capability of varying treatment parameters in software beyond the variations possible in the earlier DIAPULSE® apparatus;

the automatic creation and updating of a patient file which logs treatment parameters and other information, and the ability to access, upload and down load the patient file and information therein;

the reduction of power consumption and power dissipation by and in the improved apparatus; and provide an entirely "solid-state" apparatus.

An improved apparatus for applying electromagnetic energy to a treatment area is disclosed herein which has the capability of maintaining (and does maintain) the specific operating parameters described above of DIAPULSE® treatments, has the capability of regulating these parameters more precisely and/or for safety purposes, and also the capability of changing these parameters for use in DIAPULSE® type treatments and research, and in new or modified treatments and research, both non-thermal and thermal. A method for creating and updating, etc., a patient or research file is also disclosed. The file may be multimedia, e.g., include images and/or sound.

When operated in a non-continuous or pulsed manner, as when administering DIAPULSE® treatments, the inventive apparatus generates and radiates bursts of RF electromagnetic energy to a treatment area, with reduced power consumption and dissipation by causing the primary (or major) RF power handling or generating component(s) to be in an off or non-conductive state except substantially during the bursts. According to the invention, power to the primary RF power component(s) is continuously maintained, i.e., the power to the primary RF power component(s) is not pulsed, and the primary RF power component(s) is (are) caused to turn on or conduct substantially only during the bursts. Specifically, the inventive apparatus includes a primary RF power component in the form of one or more RF power amplifiers which output high peak RF power pulses in bursts. According to the invention, power is connected to the RF power amplifier(s) continuously, and the RF power amplifier(s) is (are) biased on for the length of each burst and is (are) biased off substantially at all other times. In the preferred embodiment, two RF power amplifiers are provided connected in parallel, and a power splitter is provided to supply input pulses to the two RF power amplifiers from a common source, e.g., an RF preamplifier, and a power combiner is provided at the outputs of the two RF power amplifiers to combine the pulses output by the RF power amplifiers and provide the combined pulses to a radiating device, e.g., a treatment head.

In another embodiment, the primary RF power component(s) may be one or more solid state RF power oscillators which are selectively biased into oscillation during the bursts.

In the preferred embodiment, bias is supplied to the RF power amplifier(s) by a bias circuit which may be enabled and disabled by a control signal. In accordance with the invention, the bias circuit is enabled for substantially only the duration of each burst, i.e., are gated into enablement for substantially only the duration of each burst. The bias circuit in the preferred embodiment comprises at least one controllable voltage regulator coupled to supply, when enabled, the bias voltage to the RF power amplifiers(s).

In the preferred embodiment, power is supplied to the primary RF power component(s) through a power storage device which stores power between bursts supplied by a power supply, and then releases the stored power to the primary RF power component(s) during the bursts. Thus, the power supply continuously supplies power to the power storage device at a low rate compared to the peak power of the RF pulses. This has the advantage that the power supply may have a continuous power rating which is substantially less than the peak power of the pulses in each burst or series of bursts output by the primary RF power component(s). Also, in the preferred embodiment, pulses to be amplified are not supplied to the primary RF power component(s) except during the time periods of the bursts. In the preferred embodiment, the power supply is a DC power supply and the power storage device(s) comprise one or more capacitors.

The inventive apparatus controls the repetition rate of the bursts of pulses in accordance with a burst repetition rate selected by a user, and includes a configurable logic device, coupled to a pulse generator, which comprises a plurality of separately configurable logic elements. The configurable logic device outputs pulses to be amplified during the bursts and outputs signals which control operating parameters, e.g., the burst repetition rate and burst duration. In the preferred embodiment, these signals control the voltage regulator(s) which supplies(y) the bias voltage(s) to the power amplifier(s). The configurable logic device may be configured to support operation of the apparatus for all of these operating parameters without being reconfigured, but can be reconfigured, if desired, to change an operating parameter or parameters. Alternatively, the configurable logic device may be configured to operate in a plurality of modes in which the configurable logic device is reconfigured, preferably dynamically, from mode to mode. In the preferred embodiment, the reconfigurable logic device is dynamically reconfigurable to operate in each of a plurality of modes. In the preferred embodiment, a memory device is provided to store a plurality of configuration files, each file when loaded into the configurable logic device causing the configurable logic elements to be configured to operate in one of the plurality of modes. A controller or processor is coupled to the configurable logic device and the memory device to select the configuration file stored in the memory device to be loaded into the configurable logic device based on a desired burst duration and/or repetition rate which may be input by a user or determined by the apparatus according to a program or dynamically in response to measured or detected parameters. In the preferred embodiment, the burst repetition rate is selected by the user and the burst duration is fixed, but could be made variable, and the configurable logic device is a logic cell array.

According to the invention, the controller comprises a system processor or controller and a local processor or controller. The configurable logic device is coupled to the local controller which causes information stored in a memory device coupled to the local controller to be transferred to the configurable logic device to configure or program it. The local controller is directed by the system processor which is preferably that of a computer. In the preferred embodiment, the inventive apparatus includes at least one input device coupled to the system processor for inputting information related to one or more of the parameters of the bursts, including but not limited to the following: the time between bursts (burst repetition rate), the duration of the bursts, a desired peak power level of the pulses in the bursts, and an overall length of time that the bursts are to be supplied. In the preferred embodiment, the burst length is in the order of 65 $\mu$sec., and the burst repetition rate is from about 80 bursts per second to about 600 bursts per second ("bps") (time between bursts of from about 12.5 msec. to about 1.6 msec).

The parameters may be set by a user through any suitable input device (e.g., keyboard, mouse and display, touch screen, digitizer). In lieu of or in addition to setting parameters with an input device, the parameters may be stored in memory and set into the apparatus according to a program controlling the processor. The parameters may be input into or changed in the memory by any suitable input device, or by downloading from an apparatus co-located with or located remotely from the inventive apparatus, or dynamically in response to measured, detected or monitored conditions or parameters.

Like earlier DIAPULSE® apparatus, the preferred embodiment of the inventive apparatus generates high peak power RF pulses in short bursts for athermapeutic treatment. This apparatus includes an RF pulse generator, an amplifier, and a radiating device coupled to the amplifier for radiating electromagnetic pulses received from the amplifier.

According to preferred embodiments of the invention, the inventive apparatus includes a closed loop, real time power adjustment system for automatically adjusting RF electromagnetic power delivered to a load to a desired level. The power adjustment system comprises a power monitor which provides in real time a first (or forward) power level signal related to the forward power level of RF pulses radiated by the radiating device. This signal may be used by itself to regulate the peak power level of the pulses output by the power amplifier(s) to the load, which here comprises the treatment head and the treatment area. The amplifier includes a variable gain stage. A processor or controller which controls the timing of the bursts is coupled to receive at least the first signal, calculate therefrom the forward power level of the RF pulses delivered to the load, and provide a control signal to the amplifier gain control stage which causes the amplifier to adjust the amplitude of RF pulses supplied to the radiating device at or closer to the desired power level in real time, e.g., within the time period between bursts. The apparatus thus can sample and regulate the peak power output by the apparatus, and does not depend upon colormetric measurements to regulate the power output. This real-time power measurement and regulation capability minimizes the time period during which power may be radiated at an unwanted, and perhaps unsafe, level.

In the preferred embodiment, the power monitor also provides a second (or reflected) power level signal related to the reflected power level of an RF signal reflected by the load. The processor or controller also receives the second signal, calculates the power reflected from the load and provides the control signal to the variable gain stage in response to both the first signal and the second signal.

In the preferred embodiment, the power monitor provides analog first and second power level signals, and the apparatus comprises an analog to digital converter coupled to receive the analog power level signals from the power monitor and provide digital power level signals to the processor, and the processor provides digital signals to the variable gain stage which cause the amplifier to supply RF pulses at the desired power level. In the preferred embodiment, the processor provides the digital signals to a digitally controlled resistance, which controls the gain of the variable gain stage.

The power adjustment system may also include a second closed loop for automatically limiting the RF electromagnetic power delivered to the load to a below a maximum level. In the preferred embodiment, the second loop is analog, is not controlled by a processor and is responsive only to the first analog power level signal. This second closed loop includes a circuit which receives the first analog power level signal and prevents the power level of the amplified pulses from exceeding a given maximum value. Also, the system may include a third loop which ensures that the electromagnetic power is not radiated unless the control signal(s) directing same are present. The second and third loops provide the "fail-safe" operation referred to above.

In the preferred embodiment, the variable gain amplifier stage comprises one or more solid state devices (e.g., transistors) whose DC supply or bias level is adjusted to adjust the gain thereof. The adjustment may be made by the power monitor system as described above, or in response to data or settings input by a user or stored in the apparatus in software or hardware. An RF transformer is coupled to the output of the solid state device(s) to couple pulses output thereby to a preamplifier or amplifier. The DC supply or bias is supplied to the primary of the RF transformer which supplies the DC to the solid state device(s). In the preferred embodiment, the solid state device is an RF transistor having its collector coupled to the transformer primary and operating in the common base mode. The digitally controlled resistance is coupled to another transistor operating in the common emitter mode with its emitter coupled to the transformer primary, its collector coupled to a source of DC power, and its base coupled to the variable resistance. This arrangement enables the gain of the RF transistor to be controlled with low frequency components.

The power adjustment system is used in the preferred embodiments of the invention for the application of DIAPULSE® treatments, but the entire power adjustment system or parts thereof may be used in other applications, both thermal and non-thermal.

The invention also provides an indication or alarm when there has been a change by a given amount of the RF energy delivered to the treatment area (detected in the preferred embodiment by a ratio of the forward and reflected power levels at the treatment head). This may be caused by relative movement between the treatment head and the treatment area, i.e., in the case of a patient, either the treatment head or the patient has moved, or other factors. Such movement is manifested by a mismatch in the forward and reflected power levels at the treatment head, which is detected. When the mismatch reaches or passes a given value, an indication is provided by the apparatus, which could be audio, visual or simply an electronic recording of same. The indication may be provided by any conventional audio device, display, indicator, etc.

According to the invention, files such as patient or research project files may be automatically generated, updated and maintained in apparatus for applying treatments to a treatment area. Such apparatus may be apparatus of the type disclosed or referred to herein, or other apparatus. The apparatus receives information input by the user, which includes identifying information about the patient or project, and at least one treatment parameter selected by the user. The apparatus measures, monitors, detects, or tracks the at least one treatment parameter while the apparatus is administering the treatment, creates or modifies at least one file based on the identifying information about the patient or project, and stores the identifying information and the at least one treatment parameter in the at least one file. The apparatus may also measure or obtain treatment information and/or at least one treatment attribute, and also store the treatment information or attribute in the file. For example, the treatment information or attribute may be optical data (e.g., scanned photographically, magnetically, electromagnetically, ultra-sonically, etc.) relating to the treatment area, which provides the apparatus with multi-media capability. If desired, sound may also be provided to enhance the apparatus' multi-media capability. The at least one treatment attribute may be obtained while the apparatus is administering the treatment, or before or after the treatment has been administered. The information in the file may be displayed, printed and/or stored, and may be accessed for uploading, down loading and modification by other apparatus, either by direct connection or a communication link.

DESCRIPTION OF THE DRAWINGS

The invention is illustrated in the figures of the accompanying drawings which are meant to be exemplary and not limiting, in which like references in different figures refer to like or corresponding parts, and in which:

FIG. 2 is a block diagram of one of the power amplifiers depicted in FIG. 1 and an embodiment of a gate circuit for turning off the bias to that power amplifier;

FIG. 3 is a block diagram of the power monitor of the apparatus of FIG. 1;

FIG. 5 is a block diagram of a circuit for cutting off power to the power amplifiers if the apparatus radiates electromagnetic power in the absence of the appropriate control signal;

FIGS. 6–8 are screen displays for touch screen inputs of the touch screen of the apparatus of FIG. 1, in which:

FIG. 6 is a screen for inputting identifying information about a patient;

FIG. 7 is a screen for selecting treatment parameters; and

FIG. 8 is a screen displayed while a treatment is in process; and

FIG. 9 is a sample patient file record generated by and stored in the apparatus of FIG. 1.

DETAILED DESCRIPTION OF THE PREFERRED EMBODIMENTS

The preferred embodiments will be described herein with reference to the drawings and the computer program listings contained in the Appendix, which are incorporated into and form part of this specification.

Figure 1:
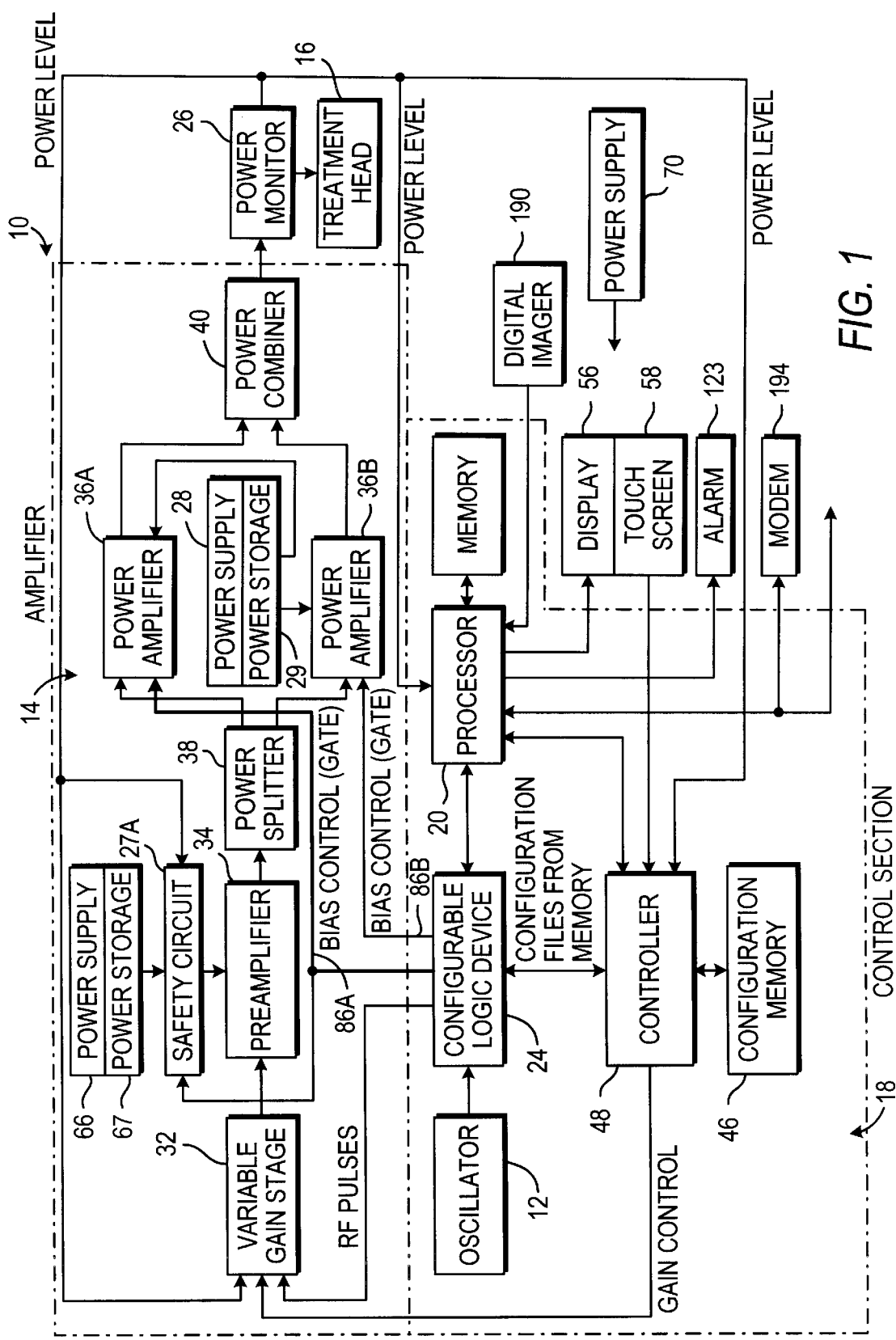
FIG. 1 is block diagram of an improved athermapeutic treatment apparatus in accordance with a preferred embodiment of the invention.

Referring to FIG. 1, an improved, computer-controlled DIAPULTSE® treatment apparatus 10 of the type described above generates and radiates from a treatment head 16 short bursts of high frequency, high power electromagnetic pulses at a frequency of 27.12 MHz., although the apparatus may generate and radiate at other frequencies if desired. A crystal oscillator 12 generates a 27.12 MHz. square wave clock signal which is used both as a timing signal and as the source of the RF pulses radiated by the treatment head 16 after amplification by an RF amplifier 14. The apparatus 10 is controlled by a control section 18 which includes a processor 20 and memory 22. A crystal oscillator associated with the processor 20 functions as the system clock. In the preferred embodiment, the processor 20 is a 486 or higher model microprocessor available from Intel Corporation. However, other processors available from Intel and other sources may be used.

As shown in FIG. 1, the clock signal from the oscillator 12 is fed into a configurable logic device 24, described below, which outputs the 27.12 MHz clock pulses to the amplifier 14 in short bursts, at a burst repetition rate selected by the user. In the preferred embodiment, the configurable logic device is a Xilinx XC2018 logic cell array ("LCA"). Other suitable configurable logic devices may be used, both those that are configured once for operation with all system parameters and those that are dynamically reconfigurable for system operation in modes as described herein. Such other devices will be apparent to those having skill in the art from the disclosure herein. The bursts of RF pulses are amplified by the amplifier 14 to a desired amplitude and delivered to the treatment head 16 via an RF coaxial cable 41 and a power monitor 26. The treatment head 16 radiates electromagnetic pulses at a peak RF power level selected by the user to an area of a patient to be treated. As mentioned above, the RF load comprises the treatment head 16 and the patient. Since the impedance of patients varies from patient-to-patient and in different parts of a patient's body, and since the treatment head 16 may be positioned differently for any patient or treatment area, the amount of RF power reflected back from the treatment head 16 due to a mismatch between the RF power amplifiers 36A, B and the RF load may vary from treatment to treatment. To compensate for this, an adjustable tuned circuit (not shown) is provided in the treatment head 16. Further compensation for this and/or to tune different lengths of a coaxial cable 41 coupling the amplifier 14 to the treatment head 16 another adjustable tuned circuit (not shown) may be provided at the apparatus side of the coaxial cable.

In accordance with the invention, the apparatus 10 additionally includes a closed loop, real-time power adjustment system, described below, which adjusts the power radiated to the patient in response to: both the forward and reflected power levels described above, and also in response only to the forward power level. The power adjustment system measures, or detects, in the power monitor 26 (FIG. 1) the level of RF (forward) power delivered to the treatment head 16 (which is representative of the RF power radiated to the patient) and the level of RF power reflected at the treatment head 16, and supplies this information to the control section 18 which then adjusts the gain of amplifier 14 to thereby adjust the forward RF power level.

The power adjustment system includes three closed control loops, one including the processor 20 and the other two bypassing the processor 20. As shown in FIG. 1, in one loop, the processor 20 receives the forward and reflected power levels detected by the power monitor 26. As described below, processor 20 computes the actual power delivered to the treatment head 16, and determines a revised amplitude of the RF pulses to be radiated which would provide an actual RF power at or closer to the power level selected by the user. The processor 20 provides revised signals to the amplifier 14 to essentially continuously adjust the amplitude of the pulses in real time. The processor 20 controls the duration of the treatment and the burst repetition rate (duty cycle) of the RF pulse bursts, and controls the amplifier 14 to set the amplitude of the RF pulses delivered to the treatment head 16 to achieve peak adjustable RF power levels of from less than about 300 watts to about 1000 watts or more, and average power levels of from less than about 1.5 W to about 38 W or more, all as selected by the user who may be a doctor, nurse, therapist, medical professional, etc., or even the patient him or herself. The apparatus 10 has the capability of providing peak powers of less than about 300 W and more than about 1000 W and average powers of less than about 1.5 W and more than about 38 W, primarily or exclusively under software control, except that where higher peak and average powers are desired, it may also be necessary to provide higher power hardware components.

In another loop (not shown in FIG. 1 and described below with reference to FIG. 4), the forward detected RF power level signal from the power monitor 26 is fed to a circuit 27 which is a fail-safe circuit that prevents the pulses output by the amplifier 14 from exceeding a maximum amplitude value in the event that the forward power exceeds a predetermined safety threshold. This eliminates any danger to the patient should the burst length, burst repetition rate and/or pulse amplitude change.

The RF amplifier 14 includes an RF preamplifier 34 and RF power amplifiers 36A and 36B. Power for the RF preamplifier 34 (FIG. 1) is supplied by a DC power supply 66 and an associated power storage device 67. In a third loop shown in FIG. 1, the forward detected RF power signal from the power monitor 26 is fed to a circuit 27A (shown schematically in FIG. 5) which cuts off the power from the power supply 66 if a given level of forward power is detected in the absence of a control signal (line 86A, or line 86B in FIG. 4). Circuit 27A is another fail-safe circuit which ensures that the apparatus 10 does not radiate power unless the apparatus 10 generates the appropriate control signal.

Power for the RF power amplifiers 36A and 36B (FIG. 1) is supplied by a DC power supply 28 and an associated power storage device 29. The DC power supply 28 has a continuous power rating significantly less than the peak power of the radiated pulses. The continuous rating of the power supply 28 depends upon the peak power and the average power of the radiated pulses. For example, for a maximum peak power of about 1000 w and a maximum average power of about 38 watts, the continuous power rating of power supply 28 may be only 38 watts, plus any losses and a safety factor, which in the case of amplifiers 36A, 36B is in the order of 50%. In the preferred embodiment where the maximum peak power is about 1000 W and average power is about 38 W, the power supply 28 has a continuous rating of 100 W and the power storage device 29 comprises 10,000 $\mu f$ of capacitance connected across the output of the power supply 28. The fail-safe circuit 27 (FIG. 4) also eliminates the risk that the peak power will be sustained.

The three-loop system described above provides for precise, computerized, fail-safe control over the power radiated by the apparatus, thus improving the quality and safety of the treatments.

The amplifier 14 (FIG. 1) also includes a variable gain stage 32, whose gain is controlled by the first loop discussed above, in addition to the preamplifier stage 34 and the power amplifiers 36A and 36B. The power amplifiers 36A and 36B are turned on only a short time before each burst is generated and during each burst, and are turned off all other times. The configurable logic device 24 provides a signal to control the timing of the turn-on of the power amplifiers 36A and 36B, and also passes RF clock pulses to the variable gain stage 32 of the amplifier 14 during the short burst periods. Turning off the amplifiers 36A and 36B during most of the time between bursts and not supplying RF clock pulses to the amplifier 14 between bursts reduce power consumption and dissipation in the amplifier 14, and allow the use of components with lower continuous ratings. The output of the preamplifier 34 is split in a power splitter 38, and the outputs of the power amplifiers 36A and 36B are combined in a power combiner 40. The output of the power combiner 40 is supplied to the treatment head 16 through the power monitor 26 and the coaxial cable 41.

Apparatus 10 may also be operated in an open loop mode, i.e., without any power adjustment responsive to signals from the power monitor 26. During open loop operation, information regarding power levels provided by the power monitor 26 may simply be ignored. However, it is preferred that apparatus 10 not be operated without the closed loop fail-safe circuits 27 (FIG. 4) and 27A (FIGS. 1 and 5).

The configurable logic device 24 (FIG. 1 ) can be configured to provide timing for a number of different burst repetition rates. A configuration memory 46 stores configuration files which are selectively loaded into the configurable logic device 24 via a local controller 48 to configure the logic device 24 to provide the timing for different burst repetition rates. The use of a dynamically reconfigurable logic device 24 to control the burst repetition rate allows software configuration thereof without the need to replace or provide additional hardware components. The frequency of the RF pulses output by the treatment head 16 and the length of the pulse bursts may also be adjusted through software configuration of the configurable logic device 24. Frequencies higher than 27.12 MHz, require a higher frequency clock oscillator 12 (or a frequency doubler, etc.), with the configurable logic device 24 being configured to provide lower frequency clock signals as needed. Thus, the improved DIAPULSE® apparatus 10 is fully adjustable by software within given ranges imposed by certain hardware components. Outside these ranges, the apparatus 10 is still adjustable in software but also may require different or additional hardware components. For example, the apparatus 10, via the configurable logic device 24 (and memory and a processor), has the capability of adjusting the duration of bursts and the burst repetition rate from a single cycle and a single bps, respectively, up to continuous wave which, however, would require replacement of some hardware components in order to operate at the higher average power levels of longer bursts and higher burst repetition rates.

The apparatus communicates information to the user through a video display screen 56 (FIG. 1) (e.g., an LCD flat panel display) and the user enters patient data and treatment parameters through a touch screen 58, e.g. an IR touch screen available from Carrol Touch Screen or a resistive touch screen available from Elographics Inc.. Other types of displays and input devices may be used, such as a conventional CRT monitor and a keyboard, mouse, or electronic stylus and digitizer.

Information entered by the user, as well as actual treatment data including the time duration of the treatment, are stored in memory 22 (FIG. 1) in an automatically generated and updated patient file. The patient file is stored on a hard disk (or in another memory device) and retrieved in later treatment sessions with the same patient so that the user can selectively utilize the same treatment parameters or adjust the parameters based on the effects of the previous treatment. The patient file of the apparatus 10 may be uploaded to and/or downloaded from and/or modified by another source, and may be printed from a printer coupled directly to the apparatus 10, or elsewhere. The other source may be remotely located and linked by a communication link such as telephone lines, as will be described below.

The DC power supply 66 (FIG. 1) in the preferred embodiment is 24 v, and the associated power storage device 67, comprises 10,000 μf of capacitance connected across the output of the power supply 66. The power supply 66 supplies DC to the preamplifier 34 and a cooling fan (not shown). The DC power supply 28 which supplies power to the power amplifiers 36A and 36B in the preferred embodiment is 48 v. A third power supply 70 supplies DC to circuits in control section 18.

All of the components of apparatus 10 may be housed together as a stand alone unit. Alternatively, all or parts of apparatus 10 may be housed within a commercially available computer e.g., a desk top computer such as a personal computer, and integrated with the computer. For example, all or some of the circuits of apparatus 10 may be installed in one or more printed circuit boards which are mounted in the computer. The processor 20, memory 22 and the power supply 70 may be embodied in the commercially available computer, which may be housed as described above. In the preferred embodiment, the oscillator 12, the configurable logic device 24, the controller 48 and the configuration memory 45, as well as the variable gain amplifier stage 32 and the fail safe circuit 27, are all contained on a single printed circuit board, and comprise the components shown in FIG. 4. The fail safe circuit 27A may also be contained on that board. The other components shown in FIG. 1 are not contained on that board.

Referring to FIG. 1, bursts of RF pulses from the configurable logic device 24 are fed into the variable gain amplifier stage 32, which receives gain control signals from the control section 18, as will be described in detail below with reference to FIG. 4. The output from the variable gain amplifier stage 32 is fed into preamplifier 34 having a nominal power gain of 40 dB and capable of developing 20 watts of RF power. The preamplifier 34 may be conventional. The preferred embodiment of the preamplifier 34 is described in literature published by Motorola, and includes a Motorola MHW59 hybrid module driving a pair of MRF426 power transistors. However, other preamplifiers apparent to those of skill in the art may be used.

The output from the preamplifier 34 is fed into power splitter 38 (FIG. 1), which in the preferred embodiment is conventional, e.g., a ferro-magnetic device having a nominal input and output impedance of 50 ohms. The power splitter 38 divides the power level of the incoming pulses in half, sending half to each of two identical power amplifiers 36A and 36B connected in parallel, which may be conventional. The preferred embodiment of power amplifiers 36A and 36B is described in literature published by Motorola, and each amplifier 36A, 36B includes a push-pull circuit 76 (FIG. 2) employing four MRF150 RF power FETs. Other power amplifiers apparent to those of skill in the art may be employed. Each amplifier 36A, 36B has a gain of 20 dB and can produce RF pulses of up to 600 W peak power. The power amplifiers 36A and 36B are used in a hybrid parallel configuration to obtain a combined peak output power of up to 1200 W at the output of the power combiner 40.

In the preferred embodiment described herein, the preamplifier 34 and power amplifier 36A, 36B provide up to 1000 W peak power output and up to 38 W average power. However, as pointed out above, other preamplifiers and amplifiers may be provided for substantially higher or substantially lower peak and average power outputs for use in other applications, both non-thermal and thermal.

Referring to FIG. 2, which shows only one power amplifier 36A (power amplifier 36B is the same), the RF pulses output by the preamplifier 34 are supplied to the push-pull circuit 76 which outputs amplified RF to the power combiner 40. The power for amplifying the pulses in amplifier 36A is supplied by power supply 28 and power storage device 29, which are coupled to the push-pull circuit 76 of both amplifiers 36A and 36B. The push-pull circuit 76 also receives a bias voltage from a voltage regulator 80 (part of the bias circuit) that in cooperation with circuitry in amplifier 36A either provides a bias voltage to the push-pull circuit 76 or does not. The voltage regulator 80 receives DC power from power supply 28 and power storage device 29, and provides or does not provide a more regulated, lower DC bias voltage to the push-pull circuit 76, and a bias control signal on a control input 82 which enables and disables the voltage regulator. The logic level of the signal on control input 82 determines whether the voltage regulator 80 is enabled or disabled, and whether it provides a bias voltage to the push pull circuit 76. Specifically, in the preferred embodiment, a logic one signal on the control input 82 enables the voltage regulator 80, and a logic zero disables it. A transistor 84 coupled between the control input 82 and line 86A from the configurable logic device 24 functions as an inverter. Thus, a logical zero signal from the logic device 24 on line 86A enables the voltage regulator 80 to cause it to provide a bias voltage which either causes or allows the power amplifier 36A to conduct, and a logical one signal from the logic device 24 on line 86A disables the voltage regulator to cause it to turn the power amplifier 36A off. Since power amplifier 36A is biased off except for the short burst periods, the signal on line 86A to turn amplifier 36A on is a short negative going pulse, which is inverted by transistor 84 to a short positive-going pulse, as shown schematically in FIG. 2.

Stated another way, configurable logic device 24 (FIG. 4) provides a gate signal on line 86A to gate voltage regulator 80 on for the burst periods and a short time therebefore. In this embodiment, the configurable logic device 24 provides a 75 µs negative-going pulse as the on gating signal on lines 86A and 86B (FIG. 1) at a selected burst repetition rate of between 80 to 600 bps. The amplifiers 36A and 36B are gated on for this short period of time and are off at all other times. For 75 µsec. on-times, at burst repetition rates of from 80 to 600 bps, the on duty cycle for the power amplifiers 36A and 36B is very low—from about 0.6% to about 4.5%. However, the actual duty cycle is that of the 65 µsec. bursts when the amplifiers 36A and 36B are on and amplifying pulses output by the preamplifier 34 to provide the high peak power pulses, which is from 0.5% to about 3.9%. With such low duty cycles, the power amplifiers 36A and 36B may be operated far in excess of their continuous power ratings, with little or no power being consumed when the power amplifiers 36A and 36B are off and in the 10 µsec. before each burst. At the highest on duty cycle of 3.9%, the average power needed to deliver bursts of radiated RF electromagnetic pulse power of 1 kW is about 38 W. Accordingly, the present invention provides the ability to use a power supply 28 as small as 38 W (plus losses and a safety factor) to deliver short, high peak power, non-thermal bursts of RF electromagnetic pulses. However, to provide for losses and to provide a safety factor, a 100 W power supply 28 is used.

As one skilled in the art will recognize, one power amplifier with twice the capacity of the two amplifiers 36A and 36B may be used in place of the two amplifiers. In that case, only one control line 86 from the configurable logic device 24 is required, and the power splitter 38 and power combiner 40 are not required and may be omitted from the circuit.

The amplified RF pulses from power amplifiers 36A and 36B (FIG. 1), combined in power combiner 40, are fed via a coaxial cable past the power monitor 26 to the treatment head 16. The power monitor 26 forms part of the three closed control loops described above for controlling the level of power output by apparatus 10.

Referring to FIG. 3, the power monitor 26 comprises a current transformer 94. a voltage transformer 96, and two identical video detector circuits 98A and 98B, one of which, detector 98A, serves as a forward power detector, and the other, detector 98B, serves as a reflected power detector. The power monitor may also be considered to include an analog-to-digital converter 112, as described below. A short length of conductor 100 in an RG-8/M coaxial cable from the power combiner 44 to the treatment head 16 is exposed and serves as the primary winding of current transformer 94. Current transformer 94 induces an AC current in its secondary 95A, 95B proportional to the RF current in conductor 100. Voltage transformer 96 generates an AC potential at each of two independent single turn secondaries 104A and 104B. These generate an AC potential proportional to the current in conductor 100 across respective parallel RC circuits, composed of resistors 102A, 102B and capacitors 103A, 103B, which act as terminating impedances. As discussed above, the treatment head 16 and the patient constitute a load to the amplifier 14. For a resistive load presented to the amplifier 14 equal to 50 ohms (the RF pulse impedance), the AC potentials across resistor 102A and capacitor 103A at the input to forward power detector 98A are in phase and are additive, while the AC potentials across resistor 102B and capacitor 103B at the input to the reflected power detector 98B are out of phase and are thus subtractive. For a load with a reactive component or a resistance not equal to 50 ohms, the magnitude of the AC potentials at the forward and reflected detectors 98A and 98B are vectorial summations of components thereof.

The AC signals provided by the transformers 94, 96 (FIG. 3) are rectified by video detectors 98A and 98B comprised respectively of diodes 106A and 106B, filter capacitors 107A and 107B, and resistors 108A, B and 109A, B. The values of these components are selected so that the outputs of the video detectors 98A and 98B are fast varying analog power level signals related to the phase angles and magnitudes of the forward and reflected RF pulses, respectively. A similar power detector is described in U.S. Pat. No. 5,424,691, the entire disclosure of which is incorporated herein by reference. The power monitor 26 is available from Tandy Corporation.

Figure 4:
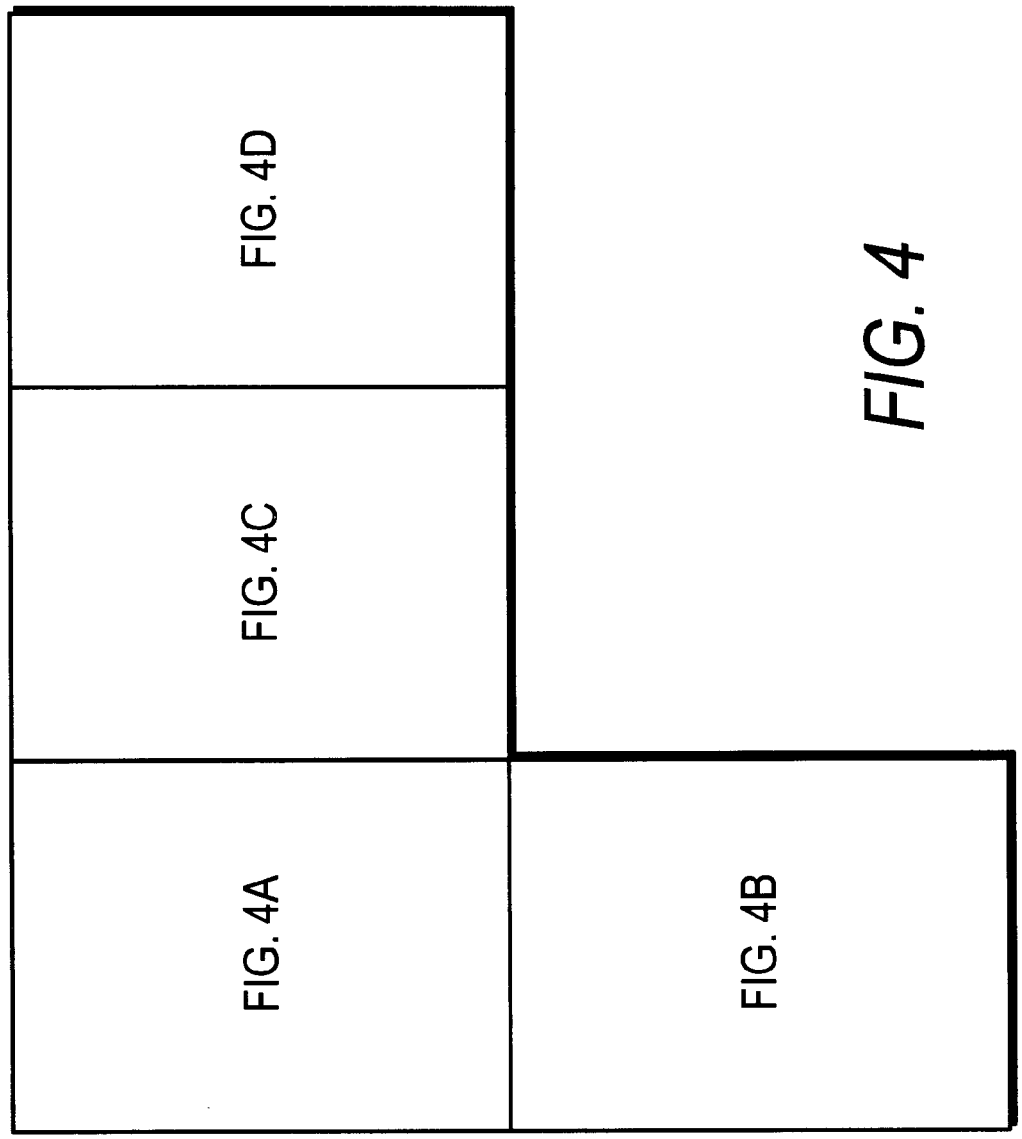
FIG. 4, consisting of FIGS. 4A, 4B, 4C and 4D, is an schematic diagram, mainly at the integrated circuit level, of a part of the control section of the apparatus of FIG. 1.
Figures 4A, 4B:
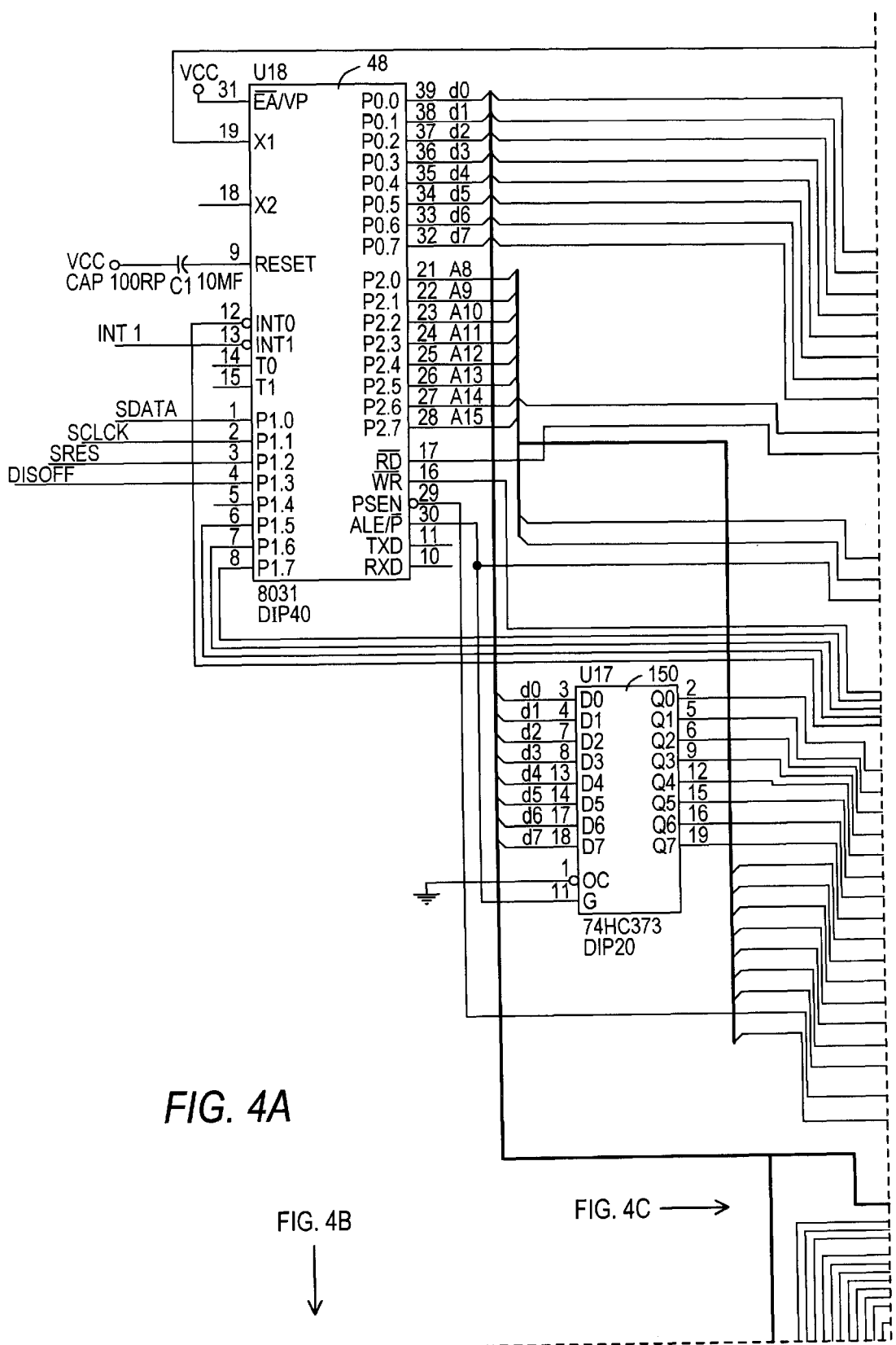
Figure 4B:
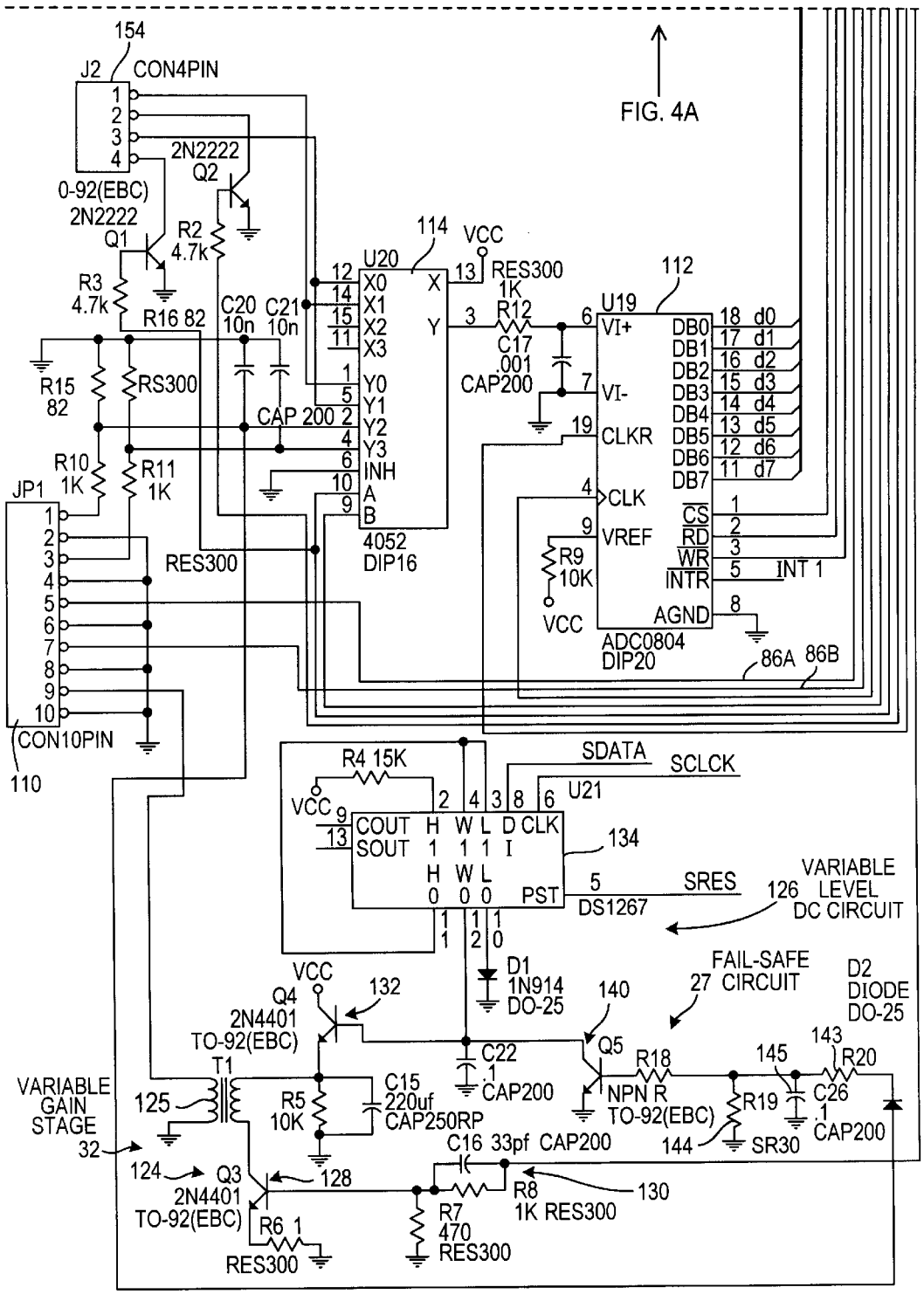
Figure 4C:
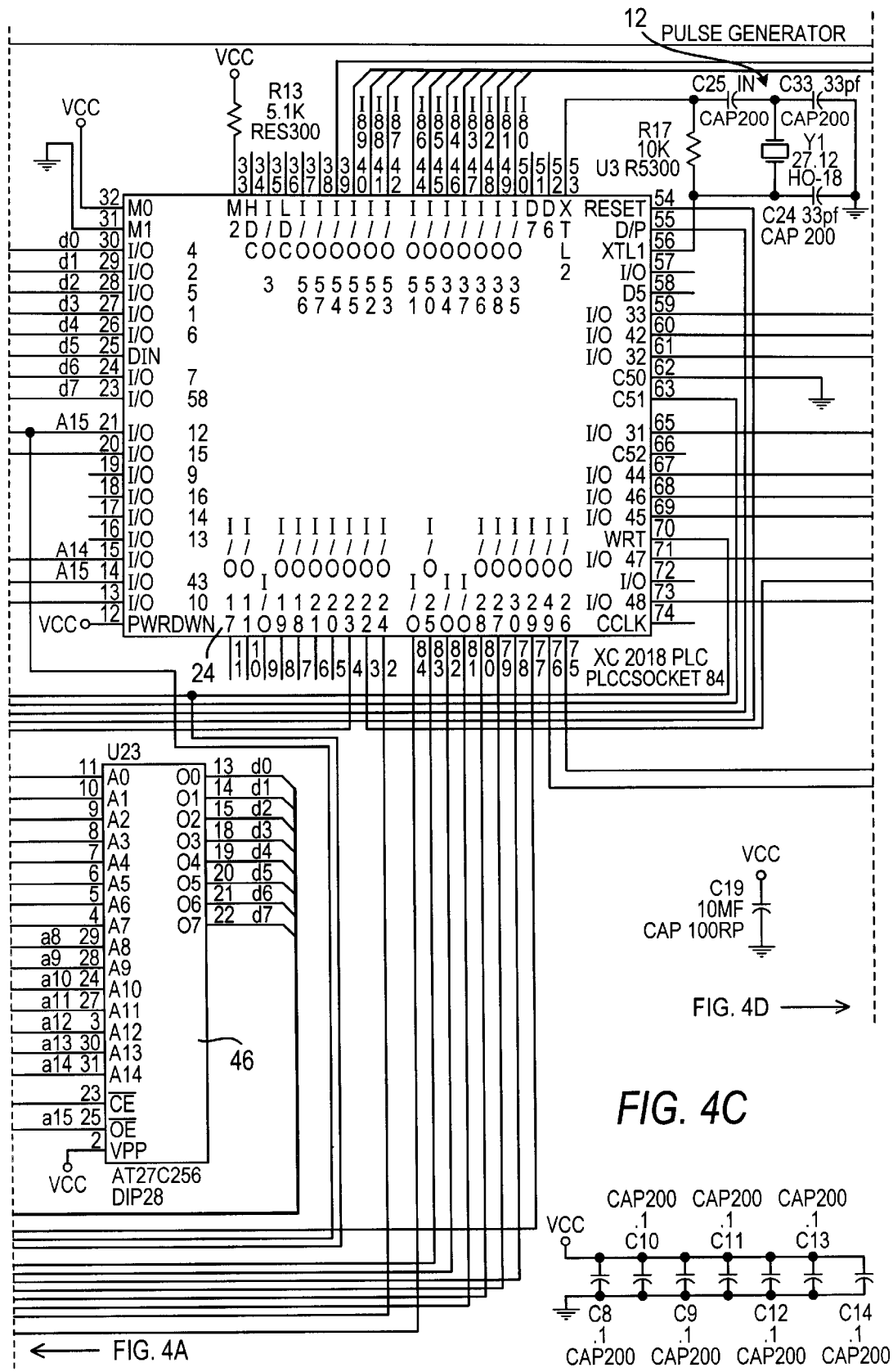
Figure 4D:
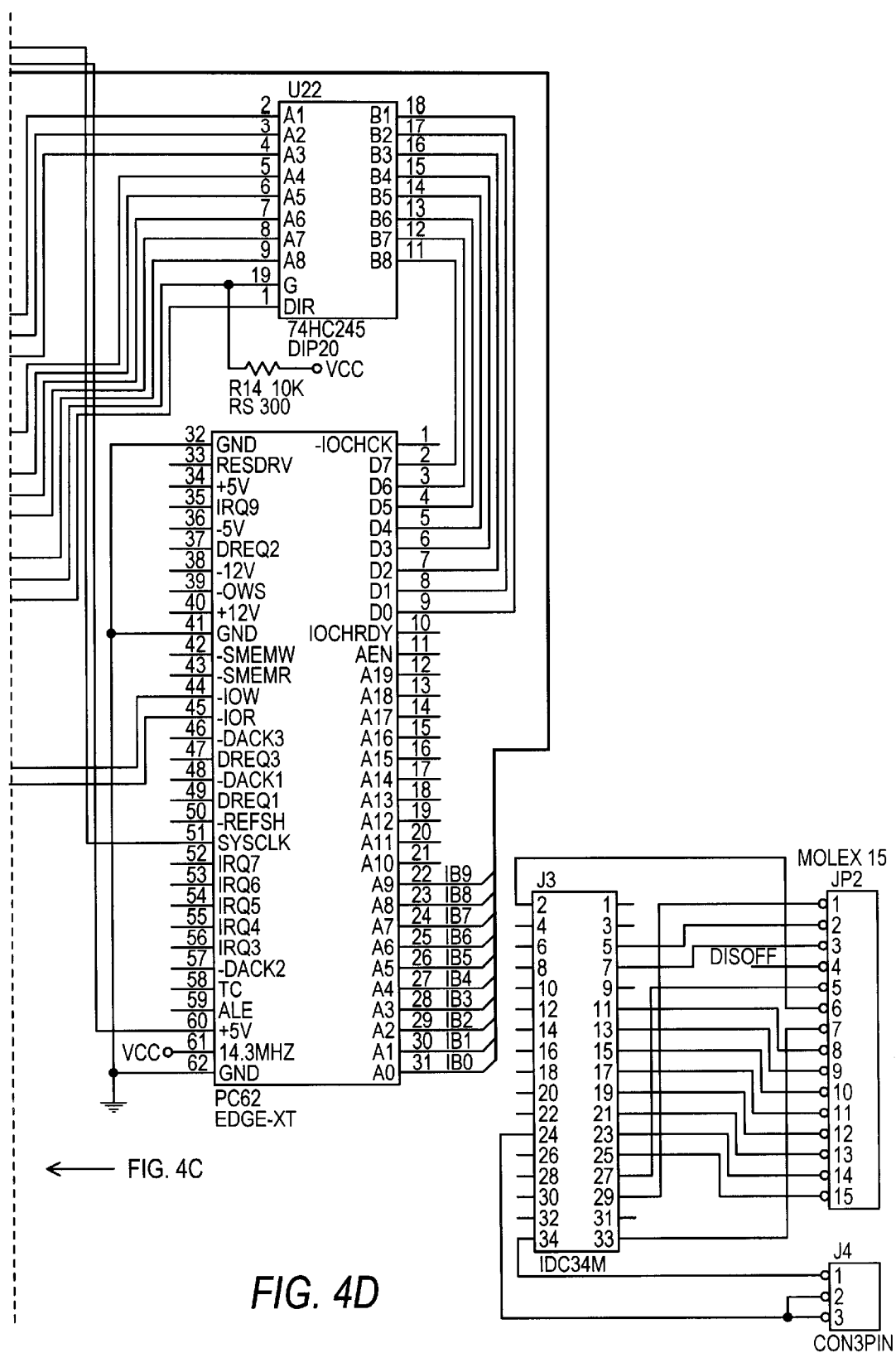

Referring to FIG. 4, in which all of the components shown therein are mounted to the printed circuit board described above, the analog power level signals output by the power monitor 26 are received on the printed circuit board through pins 1 and 3 of connector 110, and supplied to an analog-to-digital converter ("A/D") 112 through a multiplexer (MUX) 114. A/D 112 supplies digital power level signals to the controller 48 corresponding to the value of the analog power level signals. These digital power level values are provided to the processor 20 which processes the power level values to compute a value for the actual power delivered to the load, which is the forward power value minus the reflected power value. This forms part of the first closed loop described above for the real time control of the power output by the apparatus 10. (A/D112 may be considered part of the power monitor when converting analog power level signals to digital power level signals.) This actual power value is used to raise or lower the amplitude of the RF pulses output by the power amplifiers 36A and 36B so that the actual power level is closer or equal to the desired power level, as selected by a user. Because the detectors 98A and 98B are video detectors, the forward and reflected power levels are measured in real-time, and changes in the forward and reflected power levels can be detected, and appropriate changes to the RF pulse amplitude can be made, in the time period between the bursts of RF pulses. Thus, power regulation is essentially instantaneous, occurring in the preferred embodiment within from about 1.6 msec to about 12.5 msec (the time between bursts).

The processor 20 also compares the actual power value (forward to reflected power ratio) to a preset value, and when the actual power value reaches or passes (equals or falls below) the preset value, the processor outputs a signal to alarm 123 to activate it. Alarm 123 remains activated as long as the actual power value is less than or equal to the preset value. When the actual power value again exceeds the preset value, the processor 20 terminates the signal to the alarm 123, which then turns off. Alarm 123 may be any conventional audio device, indicator device, video device or display. A change in the ratio may be caused by movement of the treatment head relative to the treatment area, or by other factors. The indication or alarm notifies the patent or attendant of such movement, and the need for readjustment. If desired, the occurrence of an alarm signal may be stored to indicate a change in the power delivered to the treatment area, or for other reasons.

Referring to FIG. 1, the processor 20 supplies signals to controller 48 which in turn supplies signals to the variable gain amplifier stage 32 to adjust the amplitude of the RF pulses output by the power amplifiers 36A and 36B, which cause the variable gain amplifier stage 32 to either raise or lower the forward power level by the value of the reflected power, or, as in the preferred embodiment, which adjust the forward power level using conventional PID (proportional, integral, derivative) algorithms, well known in the art, to bring the actual power level closer to the desired power level more slowly to avoid a succession of back and forth adjustments and overshoots.

Referring to FIG. 4, the variable gain amplifier stage 32 includes an RF amplifier 124 coupled to receive the RF pulses from the configurable logic device 24, an RF transformer 125 coupled between the RF amplifier 124 and the input of the preamplifier 34 (FIG. 1) via connector 110 (FIG. 4), and a variable level DC circuit 126 for supplying a level of DC to the RF amplifier 124 via the primary of transformer 125 corresponding to the gain desired of the RF amplifier 124. The higher the DC level, the higher the output of the RF amplifier 124. The RF amplifier 124 comprises a transistor 128 having its collector coupled to the primary of transformer 125, its base coupled to receive RF clock pulses from the configurable logic device 24 through a high pass filter 130, and its emitter connected to ground through a resistor. RF pulses amplified at the collector of transistor 128 are supplied to the preamplifier 34 via connector 110. The DC level of the collector of transistor 128 determines its gain, which is set by a transistor 132 as controlled by a DS1267 digitally controlled, dual potentiometer 134, available from Dallas Semiconductor. The dual potentiometer 134 receives serial digital signals from the processor 20 (not shown in FIG. 4) via the controller 48 over the SDATA line into a data-in pin DI, which set the resistance values of the two potentiometers. The two potentiometers in the dual potentiometer 134 are connected in series between Vcc and ground, to provide a variable resistance to the base of transistor 132, as follows. The high end H1 of one potentiometer is connected to Vcc through a resistance. The wiper W1 of the one potentiometer is connected to its low end L1, which is connected to the high end HO of the other potentiometer. The low end LO of the other potentiometer is connected to ground through a diode. The wiper WO of the other potentiometer is connected to the base of transistor 132. The resistance value set in dual potentiometer 134 between the high end H1 of the first potentiometer and the wiper WO of the second potentiometer determines the DC voltage at the base of transistor 132, with the lower the setting of this resistance the lower the voltage value at the base of transistor 132. The high pass filter 130, transistor 128 and transformer 125 convert the square wave RF clock pulses output by variable gain stage 124 into a sinusoidal signal which is then input to the preamplifier 34 (FIG. 1) off the printed circuit board via connector 110 (FIG. 4).

The variable gain amplifier stage 32 (FIG. 4) just described provides the ability to digitally control the amplitude of the high frequency RF pulses output by the power amplifiers 36A and 36B using low frequency components so that the treatment head 16 delivers RF pulses of a desired magnitude as selected by the user. In the preferred embodiment, the user has six possible peak power settings, each at six possible burst repetition rates, as shown in the screen display of FIG. 7, although many more can be provided if desired. These settings provide six levels of peak power and 36 levels of average power, as shown in Table 1 below. The actual power levels may differ from those listed in Table 1, and the actual power levels for open loop operation may be different from those in closed loop operation. Known calibration techniques may be employed to obtain the actual power levels.

TABLE 1

| Power Setting | Burst Repetition Rate | | | | | | |
|---|---|---|---|---|---|---|---|
| | 600 | 500 | 400 | 300 | 160 | 80 | |
| 6 | 975 | 975 | 975 | 975 | 975 | 975 | Pk. Pwr. |
|   | 38 | 31.6 | 25.3 | 19 | 10.1 | 5.07 | Av. Pwr. |
| 5 | 780 | 780 | 780 | 780 | 780 | 780 | Pk. Pwr. |
|   | 30.4 | 25.3 | 20.3 | 16.2 | 9.1 | 4.06 | Av. Pwr. |
| 4 | 585 | 585 | 585 | 585 | 585 | 585 | Pk. Pwr. |
|   | 22.8 | 19 | 15.2 | 11.4 | 6.08 | 3.04 | Av. Pwr. |
| 3 | 488 | 488 | 488 | 488 | 488 | 488 | Pk. Pwr. |
|   | 19 | 15.85 | 12.68 | 9.5 | 5.07 | 2.53 | Av. Pwr. |
| 2 | 390 | 390 | 390 | 390 | 390 | 390 | Pk. Pwr. |
|   | 15.2 | 12.65 | 10.14 | 7.6 | 4.05 | 2.03 | Ag. Pwr. |
| 1 | 293 | 293 | 293 | 293 | 293 | 293 | Pk. Pwr. |
|   | 11.4 | 9.5 | 7.6 | 5.7 | 3.04 | 1.52 | Av. Pwr. |

The forward power level signal from the power monitor 26 is supplied both to the A/D 112 and to the fail-safe circuit 27 (FIG. 4), which also controls the gain of the variable gain amplifier stage 32 when the actual power delivered reaches a predetermined safety threshold. The fail-safe circuit 27 forms part of the second closed control loop, and comprises a transistor 140 with its collector connected to the base of transistor 132, its emitter connected to ground, and its base connected to a diode 142, resistors 143 and 144, and capacitor 145. During normal system operation, i.e., when bursts are no longer than the se burst length (e.g. 65 μs), the voltage at the base of transistor 140 will be about 0.3 V, which is not enough to turn it on. However, if the RF pulses exceed the set burst length by a predetermined threshold, or if the burst repetition rate increases, or the bursts become continuous, the base voltage at the transistor 140 will increase to turn transistor 140 on. This has the same effect as the potentiometer 134 lowering the voltage to the base of transistor 132, except that transistor 140 eventually will somewhat abruptly turn on fully to ground the base of transistor 132, which turns transistor 132 off so that no DC component is supplied at the transformer 125. With no DC component supplied to transistor 128, it does not pass the RF pulses supplied by the configurable logic device 24 so that no RF input is provided to preamplifier 34. Thus, the power amplifiers 36A and 36B will output pulses of varying magnitude between zero and a maximum value as controlled by the fail safe circuit 27, eliminating the risk of harm to the patient and to system components as the result of increased forward power due to certain failures in apparatus 10.

Another safety circuit 27A (FIG. 1), which forms part of the third closed control loop, acts to cut off the DC voltage to the preamplifier 34 if the power monitor 26 detects a given level of forward power (detector 98A in FIG. 3) in the absence of the gate signal on lines 86A, 86B (FIG. 4) from configurable logic device 24. Thus, if apparatus 10 is providing high power pulses to the treatment head 16 when it shouldn't be, circuit 27A cuts off the DC voltage to the preamplifier 34. Referring to FIG. 5, the DC voltage from the power storage device 67 is supplied to a voltage regulator 80A from which the DC voltage is supplied to the preamplifier 34. As for the voltage regulator 80 in FIG. 2, a logic level one provided on the control input 82A of voltage regulator 80A enables the voltage regulator 80A and allows it to output a DC voltage to the preamplifier 34, and a logic level zero disables the voltage regulator 80A so it does not output a DC voltage. The conditions for providing a logic level zero on input 82A are the presence of a logic level one from the forward power detector 98A and the absence of the gate signal on line 86A or B. AND gate 147 logically and's these conditions, and when they are both present, provides a logic level one to transistor 84A to turn it on and ground the control input 82A to the voltage regulator 80A. When these conditions are not present, the output of AND gate 147 is a logic level zero, transistor 84A is off, and the voltage level at control input 82A is a logic level one, as provided by the voltage division of resistors 148 and 149.

FIG. 4 also shows the circuitry for outputting the RF pulse bursts at the desired repetition rate and for controlling the touch screen interface and the timing of the A/D 112. This circuitry includes the local controller 48 programmed to carry out tasks requested by the processor 20, memory 46 in the form of an EPROM, a latch 150, the MUX 114, and filters and scaling circuitry for pulse and touch screen monitoring, and touch screen connector 154.

Still referring to FIG. 4, the controller 48 in the preferred embodiment is an Intel 8031 microcontroller, programmed to, among other things, control data transfers between the processor 20 and components shown in FIG. 4, and to control the configuration of the configurable logic device 24 by selecting one of the configuration files stored in the memory 46 to be loaded into the configurable logic device 24. The programming for the Intel 8031 microcontroller 48 is contained in the Appendix. The configurable logic device 24 receives signals from the crystal oscillator 12 at the XTL1 and XTL2 inputs. An oscillator (not shown) associated with the processor 20 on a motherboard of a desk top computer functions as the system clock. The configurable logic device 24 passes the RF pulses to the variable gain amplifier 32 in 65 μs bursts at the selected burst repetition rate by counting down the 27.12 MHz. clock.

Figure 6:
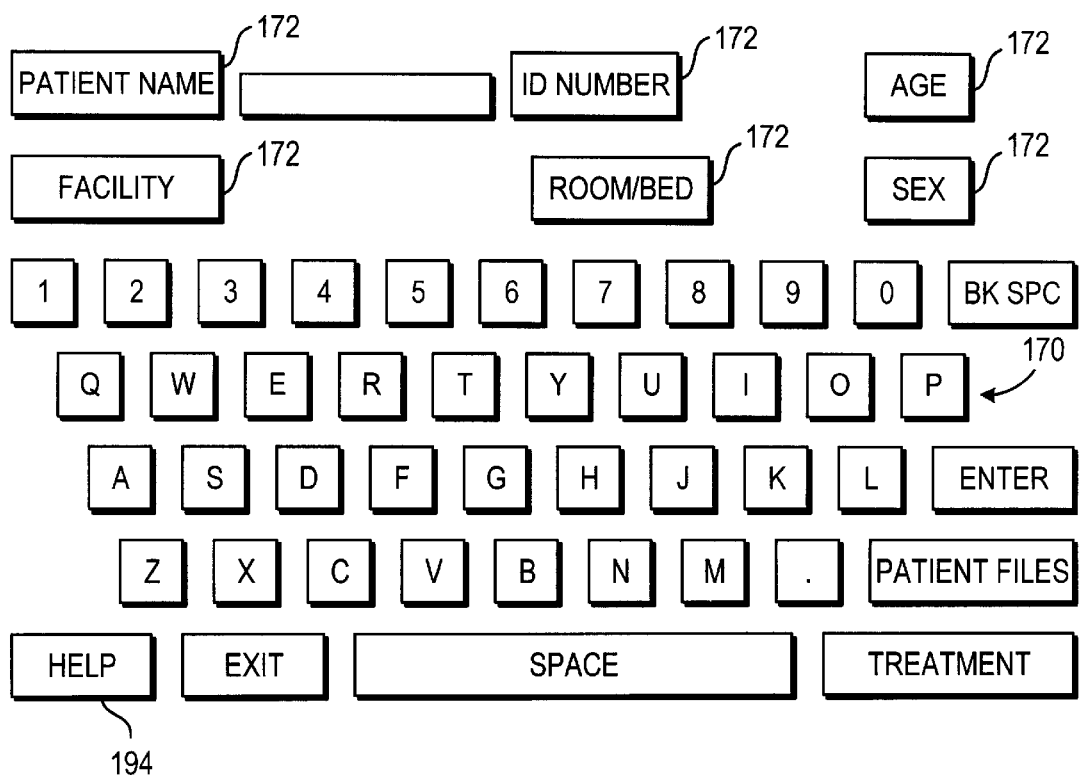

As shown in the screen display of FIG. 6, and in Table 1, the user can select from six possible burst repetition rates (labeled "frequency" in the FIG. 6 screen display). Referring to FIG. 4, for each burst repetition rate, the configurable logic device 24 is configured to count down different times between pulses. The controller 48 selects the appropriate configuration file to be loaded into the configurable logic device 24 by addressing the file in the memory 46 through latch 150. The selected configuration file is output from the memory 46 over the data lines as 8-bit data words and loaded into the configurable logic device 24 at the data input lines shown in FIG. 4. The configuration files for the Xilinx XC2018 logic cell array generated using the XACT development system available from Xilinx and stored in memory 24, are contained in the Appendix.

Still referring to FIG. 4, in addition to providing the RF pulses, the configurable logic device 24 performs other functions. It provides the bias control signals on lines 86A and 86B to pins 5 and 7 on connector 110 to the two power amplifiers 36A and 36B (FIG. 1) 10 μs before the configurable logic device 24 passes an RF pulse burst. The configurable logic device 24 also controls the timing of the A/D 112 so that the A/D 112 converts the analog forward and reverse potentials received from the power monitor 26 over pins 1 and 3 of connector 110 into digital signals during the brief duration of each RF pulse burst. The A/D converter 112 is a high speed converter capable of making about 30,000 conversions per second, thereby providing digital conversions in real time.

The timing of inputs to the A/D 112 (FIG. 4) is controlled by the configurable logic device 24 through MUX 114 as follows. MUX 114 contains two 4:1 multiplexers, indicated in FIG. 4 by inputs X0–X3 and output X, and inputs Y0–Y3 and output Y. The detected forward and reverse power signals received from the power monitor 26 (via connector 110) are input to the second multiplexer at inputs Y2 and Y3. Inputs Y0 and Y1 receive signals from the touch screen 58 (FIG. 1). The configurable logic device 24 uses the two inputs A and B of the MUX 114 to toggle the MUX 114 between the four inputs Y0–Y3 and output it to the A/D 112 through the output Y. The other 4:1 multiplexer in the MUX 114 is used to provide signals to the touch screen 58 via pins 1 and 2 of connector 154. The outputs from the A/D 112 are fed to the controller 48 which then feeds them to the processor 20 to be processed.

In this manner, the configurable logic device 24 controls the timing so that the detected analog forward and reverse RF power signals within each 65 μs RF pulse burst and the analog signals received from the touch screen are converted by the A/D 112 and supplied to the processor 20 by the controller 48 in real time so that the user can effect changes in system operation in real time.

In FIG. 4, U22 is a bus transceiver coupled to the bus of the processor 20, and J1–J4, JP1 and JP2 are connectors for interfacing the printed circuit board on which the components shown in FIG. 4 are mounted with the processor 20 and other components of apparatus 10 not mounted on the printed circuit board.

In accordance with further aspects of the present invention, user interface, data entry, total treatment time, and record keeping functions are controlled by a software program running on the processor 20. In the preferred embodiment, the software is written in the Visual Basic programming language, a compiler for which is available from Microsoft Corporation. The source code for the software program is contained in the Appendix.

Figure 7:
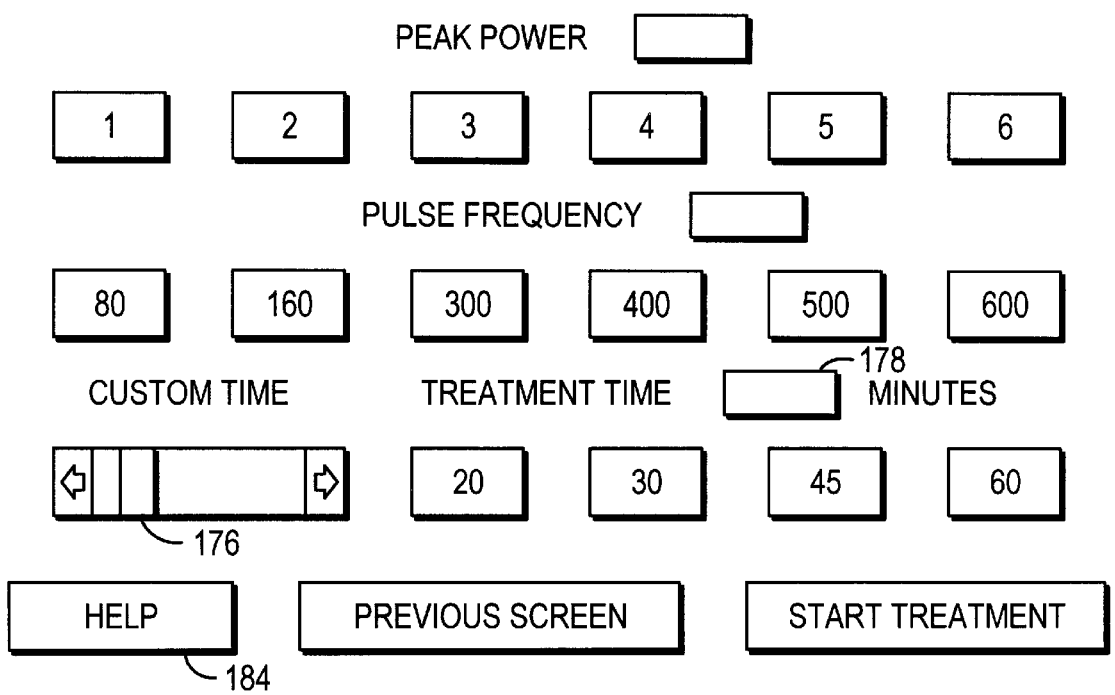
Figure 8:
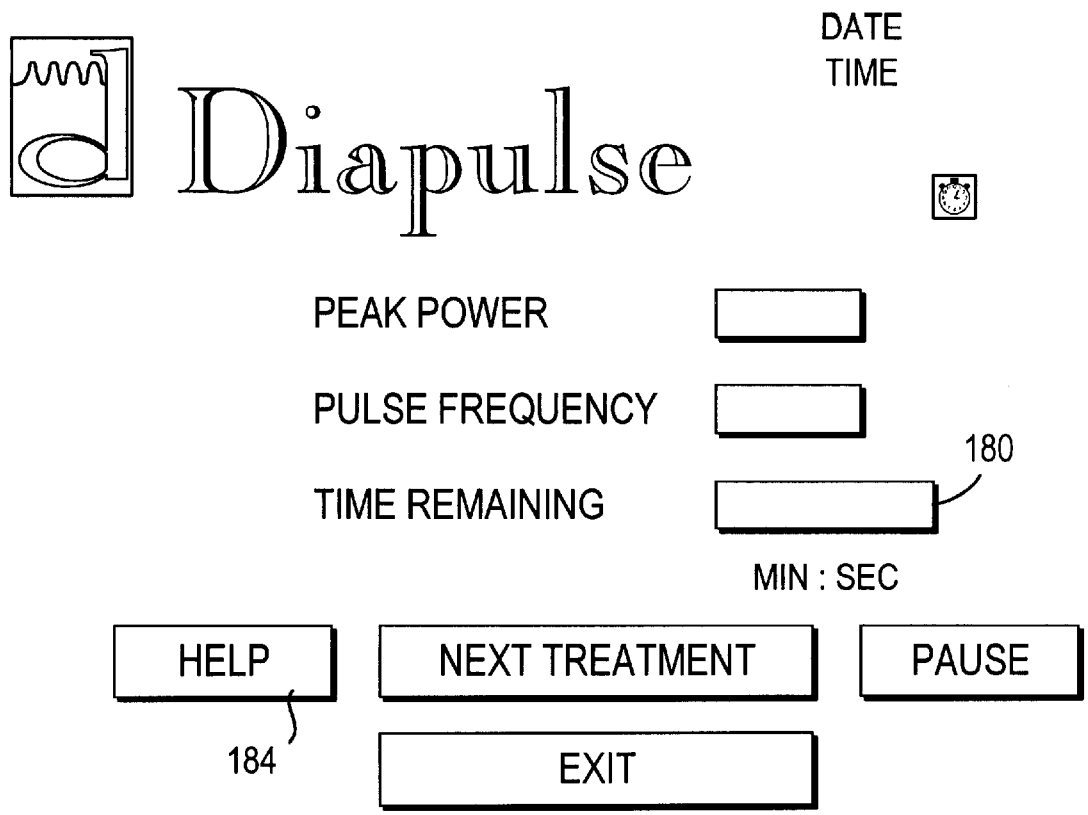

FIGS. 6–8 show screen displays through which the user enters patient information and selects treatment parameters. All pertinent patient data is entered through the screen display shown in FIG. 6, which contains a "QWERTY" type keyboard image 170 and icons 172 representing the categories of information to be entered, including patient name, patient ID number, patient age, name of facility in which treatment is being administered, patient's room/bed number, and patient's sex. Previously entered data for a patient already treated with the device may be recalled from a patient file stored in memory, such as hard disk, by touching the "Patient Files" icon on the screen display shown in FIG. 6 and entering some identifying information about the patient. Apparatus 10 then uses conventional search techniques to search for any existing patient files based on the identifying information entered by the user.

If no existing patient file is found or searched for, the user enters all the patient data. After all patient data has been entered, the apparatus 10 prompts the user for the next screen, shown in FIG. 7. This screen display allows the user to enter desired treatment parameters, including peak power level (from 1 to 6, as shown in Table 1). pulse frequency (i.e., burst repetition rate, from 80 to 600 bps), and total treatment time, entered either by selecting one of the available choices (20, 30, 45, or 60), or entering any custom length of time (Custom Time™) by moving button 174 to a desired position along a bar 176 until the desired time appears in minutes in a treatment time field 178. Once the treatment parameters have been selected, the user presses the "Start Treatment" icon to initiate the RF pulses. The processor 20 counts the time duration of the treatment until the total treatment time selected by the user is reached, at which point the processor 20 stops the treatment.

If the user retrieves the patient file for a previously treated patient, the treatment parameters for that patient are automatically entered into the fields in FIG. 7. The user may then elect to use the same treatment parameters or change the parameters. This provides for the ability to improve the quality of treatments based on the effects of prior treatments and to save input time.

The screen display in FIG. 8 is a treatment screen which advises the user as to the selected power and frequency for the current treatment being administered and keeps track of the time remaining on a down counting timer 180. The user can stop the treatment at any time by touching the "Pause" icon, and can restart the treatment by selecting the same icon, which changes to read "Resume" after a pause is initiated. While a treatment is paused, the apparatus 10 stops counting the total actual treatment time, and continues counting when the treatment is resumed.

At the end of the treatment, the apparatus 10 automatically stores the date and time, patient information, and treatment parameters, including the actual treatment time, into a patient file stored on the hard disk. If no patient file exists, the system creates a file and stores it. If a patient file already exists, the additional information is added to the file. FIG. 8 shows an example of a patient file, showing the information recorded and the file structure. The first line 182 of the file contains the date and time of file creation and identifying information about the patient, including (in order) patient name, patient ID number, facility, patient age, gender and room/bed number. The remaining lines 184 of the patient file each contain the date and time of a given treatment as well as the treatment parameters, including burst repetition rate, power level setting, and actual total treatment time. When an existing patient file is found and opened, the identifying information and last set of treatment parameters are retrieved from the file and displayed on the screen, enabling the user to use the same parameters for a new treatment or to change the information and/or parameters.

Apparatus 10 includes a help system for providing on-screen help to users. A help button 184 is provided on each screen, which when touched provides help information for that screen.

If desired, other information regarding a patient or research project may be input to the patient or research file. This may be done by inputting the information via down loading, as described below, or via an input device. For example, in the treatment of wounds, it would be desirable to have optical representations of the wound at various stages of the treatment. As shown in FIG. 1, optical data may be input into system 10 via any conventional digital imaging device, for example a conventional TV camera (e.g., a ccd device) or digital still camera 190. The camera 190 may be controlled entirely by apparatus 10 to provide digital images of the wound to the apparatus 10 at any predetermined time immediately before, during or immediately after a treatment, or semi-automatically in response to prompts output by apparatus 10 on display 56 and commands input on the touch screen 58, or manually in response to user control of apparatus 10. Programs for controlling the digitizing and input of optical images to apparatus 10 may be conventional and are known or can easily be constructed by those of skill in the art. Apparatus 10 may also be provided with sound input and playback to provide multi-media operation similar to that in current personal computer systems. A microphone, speakers, CD ROM drive, etc., may be provided in known manner to implement multi-media operation.

Referring to FIG. 1, patient file information and/or parameter settings may be down loaded from and/or up loaded to and/or modified by other apparatus, for example, through a serial port 192 (e.g., according to the RSC-232-C standard) coupled to processor 20. Such down loading, up loading, and modification may be accomplished remotely via a modem 194 and a telephone line, or an ISDN telephone line, or any other suitable communication link and associated hardware and software. Up loading, downloading and remote access are conventional and well known, and further details therefore are not supplied herein.

The apparatus 10 may be provided in modified form to carry out a programmed treatment with no or little user input other than initiating the treatment. A programmed treatment may be loaded via the serial port 192, including programming to cause the display to provide minimal prompts and the touch screen to accept minimal inputs, limited to, for example, power on/off, start and stop. The modified apparatus may include all or part of the patient file system described above for apparatus 10, including up and down loading. The modified apparatus may be provided with a digital imager 190 and multi-media capability to enhance and simplify data collection during transportable use of the modified apparatus. Also, the modified apparatus need not include a display and touch screen, but simply may be provided with an on/off switch and a start/stop switch or switches.

While the invention has been described and illustrated in connection with preferred embodiments, many variations and modifications as will be evident to those skilled in this art may be made without departing from the spirit and scope of the invention, and the invention as set forth in the appended claims is thus not to be limited to the precise details of methodology or construction set forth above as such variations and modification are intended to be included within the scope of the appended claims.

APPENDIX

COMPUTER PROGRAM LISTINGS (Pages Appendix 1 through Appendix 60)

```
GLOBAL.BAS - 1

Declare Function inp Lib "INOUT.DLL" (ByVal address&) As Integer
Declare Sub out Lib "INOUT.DLL" (ByVal address&, ByVal value%)
Global port As Integer, ap As Integer
Global ac(0 To 4)
Global x As Integer, y As Integer, onflag As Integer
Global pot1 As Integer, pot2 As Integer
Global FirstFlag As Integer
Global p As Integer
Global tt_min As Integer
Global PName As String
Global PId As String
Global Facilty As String
Global PAge As String
Global PBed As String
Global PSex As String
Global FName As String
Global Fext As String
Global TTimeSec As Integer
Global pi As Integer
Global fr As Integer
Global TreatTimeFlag As Integer
Global FI_x As Integer
Global TargetPower As Integer
Global ref As Integer, fwd As Integer, rev As Integer
Global minr, minf, maxr, maxf
Global TFlag As Integer
Global ti As Integer
Global EndTreatTime As String
Global EndTime As String
Global PatientFile As String
Global form5flag As Integer
Global Etime As Integer
Global STime As Integer
Global frm As Integer
Global Findex As Integer, Pindex As Integer, Tindex As Integer, index As Integer
Global line1(0 To 9)
Global line2(0 To 8)
Global line3(0 To 7)
Global ystart As Integer, formi As Integer
Global cflag As Integer
Global HelpI
Global fmin, fmax, rmin, rmax Sub ReadTouch ()
'    On Error Resume Next
a = 0
c = 1
'       OUT &H280, 0
        a = inp(&H280)
        i = 10
        ma = 0
start:
    DoEvents
        Call readvalue
        If ac(1) > 225 Then onflag = 0: GoTo start
        If ac(1) < 220 And onflag = 1 GoTo start ma = ma + 1
        x = 185 - Int(ac(1) / 3) * 2 + 2'(x + a(0)) / 2      Appendix, page 1
        y = 240 - Int(ac(2)) '/ 3) * 3
```

```
GLOBAL.BAS - 2
        If formi = 0 Then
            y = y + ystart + (y - 127) / 10
        End If
        If ma < 2 GoTo start
        ma = 0

'PSET (a(0) / 210 * 600, 300 - (a(1) / 180 * 300))
        ' Circle (640 - (x - 10) / 100 * 640, (y - 10) / 70 * 200), 2
'         Print x, y
       'PRINT a(0) / 210 * 600, 300 - (a(1) / 180 * 300)
'          LOCATE 10, 10
'          PRINT a(0), a(1), a(2), a(3);
        onflag = 1
        Beep
End Sub Sub readvalue ()

For i = 0 To 3
            On i + 1 GoSub out0, out1, out2, out3
            GoSub waitpre
wa:
            st = inp(&H288)
                If (st And 16) = 0 GoTo wa
waa:
            a = inp(&H280)
            GoSub convert
            ac(i) = a
        Next i
        If Abs(fwd - ac(3)) < 3 Or Abs(rev - ac(0)) < 3 Then
                If fmin > ac(3) Then fmin = ac(3)
                If fmax < ac(3) Then fmax = ac(3)
                If rmin > ac(0) Then rmin = ac(0)
                If rmax < ac(0) Then rmax = ac(0)
        Else
                fmax = ac(3)
                fmin = ac(3)
                rmax = ac(0)
                rmin = ac(0)
        End If fwd = (fmax + fmin) / 2    'fwd * 1 + a(3)) / 2
        rev = (rmax + rmin) / 2    '(rev * 1 + a(0)) / 2

Exit Sub
waitpre:
     st = inp(&H288)
        If (st And 16) = 0 GoTo waitpre
           a = inp(&H280)
                If a <> 240 GoTo waitpre
w1:
        st = inp(&H288)
        If (st And 16) = 0 GoTo w1
             a = inp(&H280)
                If a <> 15 GoTo w1
        Return
                                                        Appendix, page  2
out0:
```

```
GLOBAL.BAS - 3
        out &H280, 16
        Return
out1:
        out &H280, 2
        Return
out2:
        out &H280, 18
        Return
out3:
        out &H280, 32
        Return convert:
        b = 0
        For m = 0 To 7
                If (a And 2 ^ m) > 0 Then
                        On m + 1 GoSub cD0, cD1, cD2, cD3, cD4, cD5, cD6, cD7
                End If
        Next m
        a = b
        Return
cD0:
        b = b + 8
        Return
cD1:
        b = b + 2
        Return
cD2:
        b = b + 32
        Return
cD3:
        b = b + 128
        Return
cD4:
        b = b + 1
        Return
cD5:
        b = b + 4
        Return
cD6:
        b = b + 16
        Return
cD7:
        b = b + 64
        Return End Sub
```

Module1.bas - 1

TEST5.BAS - 1

```
Sub power_cntrl ()
        Call readvalue
        ref = ((fwd / 256 * 5) / .042) ^ 1.66 - ((rev / 256 * 5) / .042) ^ 1.66

If TargetPower > (ref + TargetPower / 100) Then
'add.power:
            dif = TargetPower - ref
            If dif > 20 And pot2 < 255 Then
                pot2 = pot2 + dif / 15
            Else
                pot1 = pot1 + dif / 30
                If pot1 > 255 Then
                        pot2 = pot2 + 1
                        pot1 = 200

End If

End If
            If pot2 > 255 Then pot2 = 255
        Else
'sub.power:
            If TargetPower < (ref - TargetPower / 100) Then
                dif = ref - TargetPower
                If dif > 20 And pot2 > 0 Then
                    pot2 = pot2 - dif / 15
                Else
                    pot1 = pot1 - dif / 30
                    If pot1 < 0 Then
                        pot2 = pot2 - 1
                        pot1 = 200
                    End If
                End If
                If pot2 < 0 Then pot2 = 0
            End If
        End If
     out &H280, 0
    ap = pot2
    Call send_byte
    ap = pot1
    Call send_byte
End Sub Sub send_byte ()

b = 0
    For i = 0 To 7
        If (ap And 2 ^ i) > 0 Then
            On i + 1 GoSub d0, d1, d2, d3, d4, d5, d6, d7
        End If
    Next i
    out &H280, b
    Exit Sub d0:
    b = b + 16
    Return
d1:
    b = b + 2
```

Appendix . page 5

```
TEST5.BAS - 2
    Return
d2:
    b = b + 32
    Return
d3:
    b = b + 1
    Return
d4:
    b = b + 64
    Return
d5:
    b = b + 4
    Return
d6:
    b = b + 128
    Return
d7:
    b = b + 8
    Return End Sub
```

Appendix, page 6

DIAD.FRM - 1

```
    ' Dim PatientFile As String

Sub CustomTime_change ()
    Beep
    TreatTime.Caption = Str$(CustomTime.Value)
    tt_min = CustomTime.Value
End Sub Sub Form_Load ()
    form1.WindowState = 2
End Sub Sub FrequencyKey_click (Findex As Integer)
    Beep
    If Fi_x = 0 Then Fi_x = 1
    FrequencyKey(Fi_x).FontSize = 12
    'FrequencyKey(Fi_x).Height = 3
    'FrequencyKey(Fi_x).Width = 7
    FrequencyKey(Findex).FontSize = 18
    'FrequencyKey(FIndex).Height = 4
    'FrequencyKey(FIndex).Width = 9
    Fi_x = Findex
    Select Case Findex Case 1
        Frequency.Caption = "80"
        Fr = 80
        out &H280, 112
    Case 2
        Frequency.Caption = "160"
        Fr = 160
        out &H280, 96
    Case 3
        Frequency.Caption = "300"
        Fr = 300
        out &H280, 82
    Case 4
        Frequency.Caption = "400"
        Fr = 400
        out &H280, 66
    Case 5
        Frequency.Caption = "500"
        Fr = 500
        out &H280, 80

Case 6
        Frequency.Caption = "600"
        Fr = 600
        out &H280, 64
    End Select
    For i = 1 To 8000: Next i
End Sub Sub KtExit_click ()
    Beep
    form1.Hide
    form2.Show
End Sub
```

Appendix, page 7

DIAD.FRM - 2

```
Sub KtHelp_Click ()
    Beep
    HelpI = 2
    HelpForm.Show 1
End Sub

Sub KtStart_click ()
    Beep
    If tt_min = 0 Or Fr = 0 Or pi = 0 Then Exit Sub
    TreatTimeFlag = 1
    TFlag = 0
    FirstFlag = 0
    out &H280, 50
'   cflag = 1
     form1.Hide form3.WindowState = 2
    form3.Show End Sub Sub PowerLevelKey_click (pindex As Integer)
    Beep
    port = &H280
    If pi = 0 Then pi = 1
    PowerLevel.Caption = Str$(pindex)
    PowerLevelKey(pi).FontSize = 12
    'PowerLevelKey(pi).Width = 7
    PowerLevelKey(pindex).FontSize = 18
    'PowerLevelKey(PIndex).Width = 9
    pi = pindex Open "\diapulse\Power" + Chr$(pindex + 48) + ".pwr" For Input As #2
    Input #2, pot1
    Input #2, pot2
    Input #2, TargetPower
    Close #2
'    Select Case Pindex
'
'    Case 1
'        TargetPower = 310
'        pot1 = 110
'        pot2 = 110
'
'    Case 2
'        TargetPower = 390
'        pot1 = 120
'        pot2 = 120
'
'    Case 3
'        TargetPower = 440
'        pot1 = 153
'        pot2 = 130
'
'    Case 4
'        TargetPower = 525
'        pot1 = 159
'        pot2 = 140
'
```

Appendix . page  8

DIAD.FRM - 3

```
'    Case 5
'        TargetPower = 540
'        pot1 = 160
'        pot2 = 190
'
'    Case 6
'        TargetPower = 750
'        pot1 = 200
'        pot2 = 200

'    End Select
'    rmin = TargetPower
'    rmax = TargetPower
'    fmin = TargetPower
'    rmax = TargetPower out port, 0
    ap = pot2
    Call send_byte
    ap = pot1
    Call send_byte Exit Sub End Sub Sub time20_click ()
'    Beep
    TreatTime.Caption = "20"
    tt_min = 20
    CustomTime.Value = 20
End Sub Sub time30_click ()
'    Beep
    TreatTime.Caption = "30"
    tt_min = 30
    CustomTime.Value = 30

End Sub

Sub time45_click ()
'    Beep
    TreatTime.Caption = "45"
    tt_min = 45
    CustomTime.Value = 45

End Sub

Sub time60_click ()
'    Beep
    TreatTime.Caption = "60"
    tt_min = 60
    CustomTime.Value = 60

End Sub
```

Appendix . page  9

```
FORM2D.FRM - 1
        '   Dim Shared PatientFile As String

Sub BackSpace_click ()
    Beep
    Select Case p

Case 0
        PName$ = PatientName.Caption
        a = Len(PName$) - 1
        If a < 0 Then a = 0
        PatientName.Caption = Left$(PName$, a)

Case 1
        PName$ = IdNumber.Caption
        a = Len(PName$) - 1
        If a < 0 Then a = 0
        IdNumber.Caption = Left$(PName$, a)

Case 2
        PName$ = Facility.Caption
        a = Len(PName$) - 1
        If a < 0 Then a = 0
        Facility.Caption = Left$(PName$, a)

Case 3
        PName$ = Bed.Caption
        a = Len(PName$) - 1
        If a < 0 Then a = 0
        Bed.Caption = Left$(PName$, a)

Case 4
        PName$ = Age.Caption
        a = Len(PName$) - 1
        If a < 0 Then a = 0
        Age.Caption = Left$(PName$, a)

Case 5
        PName$ = Sex.Caption
        a = Len(PName$) - 1
        If a < 0 Then a = 0
        Sex.Caption = Left$(PName$, a)
    End Select
End Sub Sub Exit2_click ()
    Beep
    Form2.Hide
    form4.Show
End Sub Sub Form_Activate ()

minf = 2000
    minr = 2000
    maxf = 0
    maxr = 0 formi = 0
    Open "\diapulse\letters.ind" For Input As #4
    For i = 0 To 9
```

Appendix, page 10

```
FORM2D.FRM - 2
        Input #4, line1(i)
    Next i
    For i = 0 To 8
        Input #4, line2(i)
    Next i
    For i = 0 To 7
        Input #4, line3(i)
    Next i
    Close #4
End Sub Sub Form_Load ()
    PatientFile = ""
End Sub Sub Id_Number_click ()
    Beep
    Call SetBackColor
    p = 1
    IdNumber.Caption = ""
    Call FixBackColor
End Sub Sub KAge_click ()
    Beep
    Call SetBackColor
    p = 4
    Age.Caption = ""
    Call FixBackColor
End Sub Sub KBed_click ()
    Beep
    Call SetBackColor
    p = 3
    Bed.Caption = ""
    Call FixBackColor
End Sub Sub KEnter_click ()
    Beep
    Call SetBackColor
    p = p + 1
    If p > 5 Then p = 0
    Call FixBackColor
End Sub Sub KFacility_click ()
    Beep
    Call SetBackColor
    p = 2
    Facility.Caption = ""
    Call FixBackColor
End Sub Sub Khelp2_Click ()
    Beep
    HelpI = 1
    HelpForm.Show 1
End Sub
```

Appendix . page 11

```
FORM2D.FRM - 3
Sub KSex_click ()
    Beep
    Call SetBackColor
    p = 5
    Sex.Caption = ""
    Call FixBackColor
End Sub Sub KSpace_click ()
    Beep
    Select Case p Case 0
        PatientName.Caption = PatientName.Caption + " "

Case 1
        IdNumber.Caption = IdNumber.Caption + " "

Case 2
        Facility.Caption = Facility.Caption + " "

Case 3
        Bed.Caption = Bed.Caption + " "

Case 4
        Age.Caption = Age.Caption + " "

Case 5
        Sex.Caption = Sex.Caption + " "

End Select
End Sub

Sub letter_Click (Index As Integer)
    Beep
    Select Case p

Case 0
        PatientName.Caption = PatientName.Caption + letter(Index).Caption Case 1
        IdNumber.Caption = IdNumber.Caption + letter(Index).Caption Case 2
        Facility.Caption = Facility.Caption + letter(Index).Caption Case 3
        Bed.Caption = Bed.Caption + letter(Index).Caption Case 4
        Age.Caption = Age.Caption + letter(Index).Caption Case 5
        Sex.Caption = Sex.Caption + letter(Index).Caption End Select End Sub
```

Appendix, page 12

```
FORM2D.FRM - 4

Sub number_click (Index As Integer)
    Beep
    Select Case p

Case 0
        PatientName.Caption = PatientName.Caption + number(Index).Caption Case 1
        IdNumber.Caption = IdNumber.Caption + number(Index).Caption Case 2
        Facility.Caption = Facility.Caption + number(Index).Caption Case 3
        Bed.Caption = Bed.Caption + number(Index).Caption Case 4
        Age.Caption = Age.Caption + number(Index).Caption Case 5
        Sex.Caption = Sex.Caption + number(Index).Caption End Select End Sub Sub Patient_Name_click ()
    Beep
    PatientFile = ""
    Call SetBackColor
    p = 0
    PatientName.Caption = ""
    Call FixBackColor
End Sub Sub PatientFiles_click ()
tryagain:
    Beep
    form5.Show 1
    PatientFile = form5.File1.FileName
    If PatientFile = "" Then Exit Sub
'   On Error GoTo tryagain
    Open "\diapulse\" + PatientFile For Input As #1

Input #1, a$
        Input #1, a$
        Input #1, a$
            PatientName.Caption = a$
        Input #1, a$
            IdNumber.Caption = a$
        Input #1, a$
            Facility.Caption = a$
        Input #1, a$
            Age.Caption = a$
        Input #1, a$
            Sex.Caption = a$
        Input #1, a$
            Bed.Caption = a$ Close #1
```

Appendix, page 13

FORM2D.FRM - 5

```
End Sub

Sub Sex_Click ()
    Beep
    p = 5
    Sex.Caption = ""
End Sub

Sub TreatmentKey_click ()
    On Error GoTo NoFile
    Beep
    If PatientFile = "" And PatientName.Caption <> "" And Left$(PatientName.Capt
ion, 1) <> " " And Left$(PatientName.Caption, 1) <> "," Then
        PName = PatientName.Caption + " "
        PId = IdNumber.Caption + ","
        Facilty = Facility.Caption + ","
        Page = Age.Caption + ","
        Pbed = Bed.Caption + ","
        Psex = Sex.Caption + ","
        Fname = ""
        ni = 1
        While Mid$(PName, ni, 1) <> " "
                Fname = Fname + Mid$(PName, ni, 1)
                ni = ni + 1
        Wend Fname = Left$(Fname, 8)
        Fext = Mid$(PName, ni + 1, 3)
        If Fext = "" Then Fext = "a"
        PatientFile = Fname + "." + Fext Open "\diapulse\" + PatientFile For Append As #1

Print #1, Date$ + ",", Time$ + ",", PName + ",", PId, Facilty, Page, Pse
x, Pbed
        Close #1
    End If
    If PatientFile = "" Then Exit Sub
    Form2.Hide form1.Show
    Exit Sub
NoFile:
    Exit Sub End Sub
```

Appendix, page 14

```
FORM3D.FRM - 1

Dim FileFlag As Integer

Sub Form_Unload (Cancel As Integer)
    out port, 34
End Sub

Sub K3Pause_Click ()
    Beep
    If K3Pause.Caption = "PAUSE" Then
        out &H280, 34
        TreatTimeFlag = 0
        K3Pause.Caption = "RESUME"
    Else
        out &H280, 50
        TreatTimeFlag = 1
        K3Pause.Caption = "PAUSE"
    End If
End Sub Sub K4Exit_Click ()
    Beep
    FirstFlag = 0
    TreatTimeFlag = 0
    out &H280, 34
    K3Pause.Caption = "PAUSE"
    If FileFlag = 0 Then
            Open "\diapulse\" + PatientFile For Append As #1
        '    On Error GoTo NoFile1
            Print #1, Date$, Time$, fr, pi, tt_min - ti
            Close #1
    End If
    FileFlag = 0
    form3.Hide
    form2.WindowState = 2
    form2.Show
NoFile1:
End Sub Sub K4Help_Click ()
    Beep
    HelpI = 3
    HelpForm.Show 1

End Sub

Sub KtExitLogo_Click ()
    Beep
    FirstFlag = 0
    TreatTimeFlag = 0
    out &H280, 34
    K3Pause.Caption = "PAUSE"
    If FileFlag = 0 Then
            Open "\diapulse\" + PatientFile For Append As #1
        '    On Error GoTo NoFile2
            Print #1, Date$, Time$, fr, pi, tt_min - ti
            Close #1
    End If
    FileFlag = 0
    form3.Hide
    form2.WindowState = 2
```

Appendix, page 15

FORM3D.FRM - 2

```
    form4.Show
NoFile2:
End Sub

Sub T4Timer_Timer ()
    hr = Val(Left$(Time$, 2))
    If hr > 12 Then
        lHr$ = Str$(hr - 12) + Right$(Time$, 6) + " PM"
    Else
        lHr$ = Time$ + " AM"
    End If
    F4Time.Caption = lHr$ If FirstFlag <> 1 Then
        ddate.Caption = Date$
        TFrequency.Caption = Str$(fr)
        TpowerLevel.Caption = Str$(pi)
        ti = tt_min
        TTimeSec = 0
        FirstFlag = 1
    End If If TFlag = 0 And TreatTimeFlag = 1 And cflag = 0 Then
        TTimeSec = TTimeSec - 1
        ' If cflag = 1 Then
        '     Call power_cntrl
        '     text1.Text = ref
        '     text2.Text = pot2
        '     text3.Text = pot1
        ' End If
        'cflag = -cflag
        If TTimeSec < 0 Then
            TTimeSec = 59
            ti = ti - 1
        End If
        If ti < 0 Then
            Open "\diapluse\" + PatientFile For Append As #1
            '   On Error GoTo NoFile3
            Print #1, Date$, Time$, fr, pi, tt_min
            Close #1
            FileFlag = 1
            TFlag = 1
            TTime.Caption = "END"
            out &H280, 34
        TONE = 1800
            out 67, 182
            out 66, TONE And 255
            out 66, TONE / 256
            out 97, inp(97) Or 3
            For i = 1 To 8000
                DoEvents
                ' TONE = TONE - 1
            Next i
            out 97, inp(97) And &HFC EndTime = Time$
            form6.EndTreatTime.Caption = lHr$
            form6.Show
            TreatTimeFlag = 0
```

Appendix, page 16

```
FORM3D.FRM - 3
          Else
              TTime.Caption = Str$(ti) + ":" + Str$(TTimeSec)
          End If
     End If
NoFile3:

End Sub
```

FORM4D.FRM - 1

```
    Dim amin As Integer, omin As Integer

Sub Command1_Click ()
    Beep
    Form3.Hide
    form7.Show

End Sub

Sub TechScreen_Click ()
    Beep
    form4.Hide
    form7.Show
End Sub

Sub Form_Load ()
    WindowState = 2
    Open "\diapulse\elaps.tim" For Input As #1
    Input #1, Etime
    Close #1

'    Call ReadTouch
'    If y < 30 Then Call NewPatient_click

End Sub

Sub Image1_Click ()
    Beep
    form4.Hide
    form7.Show

End Sub

Sub NewPatient_Click ()
    Beep
    form4.Hide
    Form2.WindowState = 2
    Form2.Show
End Sub Sub Timer1_Timer ()
    lDate.Caption = Date$
    ahr = Val(Left$(Time$, 2))
    amin = Val(Mid$(Time$, 4, 2))
    If amin <> omin Then
        omin = amin
        STime = STime + 1
        If STime > 59 Then
            STime = 0
            Open "\diapulse\Elaps.tim" For Input As #2
            Input #2, Etime
            Close #2
            Etime = Etime + 1
            Open "\diapulse\Elaps.tim" For Output As #2
            Print #2, Etime
            Close #2
        End If
        form7.SysTime.Caption = "SYS TIME = " + Str$(Etime)
    End If
```

Appendix Page 18

FORM4D.FRM - 2

```
    If ahr > 12 Then
        alhr$ = Str$(ahr - 12) + Right$(Time$, 6) + " PM"
    Else
        alhr$ = Time$ + " AM"
    End If
    lTime.Caption = alhr$
End Sub
```

```
FORM5.FRM - 1

Dim Touchfile As Integer

Sub Command1_Click ()
    Beep
    PatientFile = ""
    form5.Hide
End Sub

Sub File1_click ()
    Beep
    PatientFile = form5.File1.FileName
    form5.Hide
End Sub Sub Form_Activate ()

File1.Path = "\diapulse"
        File1.Refresh
End Sub

Sub Form_Unload (Cancel As Integer)
    form5flag = 1
End Sub
```

Appendix, page 20

FORM6.FRM - 1

```
Sub Command1_Click ()
    Beep
    out &H280, 34
    form6.Hide
End Sub
```

```
FORM7.FRM - 1

'    Dim PatientFile As String

Sub Command3_Click ()

End Sub

Sub Command1_Click ()
    Beep
    If cflag = 0 Then
        cflag = 1
        command1.Caption = "TEST"
    Else
        cflag = 0
        command1.Caption = "NORMAL"
    End If
End Sub Sub Command2_Click ()
    a = Shell("\dos\edit.com \diapulse\power1.pwr", 1)
End Sub Sub Form_Load ()
    form7.WindowState = 2
End Sub Sub SelectFile_click ()
    Beep
    form5.Show 1
'   PatientFile = form5.File1.FileName ' SelectedFile.caption = PatientFile
    Load form8
    form8.Show
End Sub Sub TcExit_click ()
    Beep
    form7.Hide
    form4.Show
End Sub
```

FORM8.FRM - 1

```
Dim ix

Sub Form_Activate ()
    form8.WindowState = 2
    form8.Caption = "PATIENT FILE " + PAtientFile
'    On Error GoTo NoFile4
    If PAtientFile = "" Then form8.Hide : form7.Show : Exit Sub
data1:
    filedisp.Caption = "     DATE         TIME          NAME           ID NUMBE
R       FACILITY         AGE        SEX      ROOM/BED" + Chr$(13) + Chr$(13)
'    PatientFile = form5.File1.FileName
    Open "\diapulse\" + PAtientFile For Input As #1

Line Input #1, pd$
        filedisp.Caption = filedisp.Caption + pd$ + Chr$(13) + Chr$(13)
        filedisp.Caption = filedisp.Caption + "     DATE         TIME    FREQUENC
Y POWER    TREATMENT TIME(MIN)" + Chr$(13) + Chr$(13)
        form8.CurrentX = 0
more_data:
        ix = 2000
    While Not EOF(1) And ix < 6800
        DoEvents
        Line Input #1, pd$
'       filedisp.Caption = filedisp.Caption + pd$ + Chr$(13)
        form8.CurrentY = ix
        form8.CurrentX = 0
        form8.Print pd$
        ix = ix + 200
    Wend
    If Not EOF(1) Then Exit Sub
'    Close #1

End Sub

Sub Form_Click ()
    Beep
    If Not EOF(1) Then
    Cls
        ix = 2000
    While Not EOF(1) And ix < 6800
        DoEvents
        Line Input #1, pd$
'       filedisp.Caption = filedisp.Caption + pd$ + Chr$(13)
        form8.CurrentY = ix
        form8.CurrentX = 0
        form8.Print pd$
        ix = ix + 200
    Wend
    Exit Sub
    End If
    Close #1
    form8.Hide
    form7.Show
End Sub
```

Appendix, page 23

HELPFORM.FRM - 1

```
Sub Form_Activate ()
    HelpForm.WindowState = 2
    oldx = x
    Open "\diapulse\Help" + HelpI + ".doc" For Input As #3
more_hdata:
        Cls
        ix = 200
    While Not EOF(3) And ix < 6800
        DoEvents
        Line Input #3, pd$
    '   filedisp.Caption = filedisp.Caption + pd$ + Chr$(13)
        CurrentY = ix
        CurrentX = 0
        Print pd$
        ix = ix + 200
    Wend
    If Not EOF(3) Then
'        Call ReadTouch
        GoTo more_hdata
    End If
    Close #3
'    Call ReadTouch
    x = oldx
End Sub Sub Form_Click ()
    Beep
    HelpForm.Hide
End Sub
```

```
BACKRND.BAS - 1

02-20-1996    12:16:50      600        6          1
02-20-1996    12:40:00      600        6          1

Sub FixBackColor ()
    Select Case p

Case 0
        form2.PatientName.BackColor = &HFFFF00

Case 1
        form2.IdNumber.BackColor = &HFFFF00

Case 2
        form2.Facility.BackColor = &HFFFF00

Case 3
        form2.Bed.BackColor = &HFFFF00

Case 4
        form2.Age.BackColor = &HFFFF00

Case 5
        form2.Sex.BackColor = &HFFFF00

End Select

End Sub

Sub SetBackColor ()
    Select Case p

Case 0
        form2.PatientName.BackColor = &HFFFFFF

Case 1
        form2.IdNumber.BackColor = &HFFFFFF

Case 2
        form2.Facility.BackColor = &HFFFFFF

Case 3
        form2.Bed.BackColor = &HFFFFFF

Case 4
        form2.Age.BackColor = &HFFFFFF

Case 5
        form2.Sex.BackColor = &HFFFFFF

End Select

End Sub
```

Appendix, page 25

$PAGINATE $PAGEWIDTH=132

$SHOWINCS $NOMACEVAL

;

; USE RB 0

; R0 -              R4 - Y COORDINATE OF PIXEL

; R1 - USED BY SCANPROG.     R5 - X COORDINATE OF PIXEL

; R2 - R2 COORD.      R6 - TEMP PATT.

; R3 - R3 COORD.      R7 - BIT LOCATION IN BYTE .

;

;   NOTICE: ARx - IS THE ABSOLUTE ADDRESS OF REG x !!!!

;

;

;    reg set 1 for timer

;    reg set 2 for a/d

DEFSEG  DIACN,ABSOLUTE
        SEG     DIACN

```
        ORG    0
        jmp    70h
        org    70h
        jmp    init org    11
        jmp    30h
        org    30h
        jmp    time org    3
        mov    r0,#0
        movx   @r0,a
reti
        org    13h
        jmp    50h
        org    50h
        jmp    ad_int org    23h
        jmp    60h
        org    60h
```

```
            jmp     comm

;

ad_address  equ    8000h mux_clr     equ    0a000h ibm_wrt     equ    4000h portio      equ    0c000h pc_stat     equ    0e000h rf_dis      equ    0 sec_counter equ    0ch system_flags equ   21h io_byte     equ    22h kbd_flag    equ    system_flags.0 pc_wrt_flag equ    system_flags.1 nible       equ    system_flags.2 reflected   equ    system_flags.3 first_time  equ    system_flags.4 ad_flag     equ    system_flags.5
```

Appendix, page 28

```
ad_data      equ    30h    ; 30 to 33
ad_counter   equ    34h
old_x        equ    35h
old_y        equ    36h
frequency    equ    38h
pc_status    equ    39h
com_change   equ    40h
send_counter equ    41h
input_buf    equ    42h    ; to 44h
new_pot      equ    43h
new_pot1     equ    44h pot_data     equ    p1.0
pot_clk      equ    p1.1
pot_reset    equ    p1.2 xilinx_reset equ    p1.5
xilinx_cs    equ    p1.7
xilinx_prog  equ    p1.6 x_thld       equ    250
```

; io bits mnbr    equ    30h

;

;

;

org    100h

%include "INIT.ASM"      ; INITIALIZATION.
        mov    8eh,#3            ; set for long memory access
        mov    p2,#80h clr    a
        call   set_pot
        mov    a,#0
        jmp    new_setting

```
start:
        jb      first_time,bstart
        mov     dptr,#mux_clr
        clr     a
        movx    @dptr,a         ; reset the mux counter
        mov     ad_counter,a
        mov     dptr,#rf_dis
        mov     a,#64
        movx    @dptr,a
        setb    first_time
        mov     sbuf,pc_status wait_first_loop:
        mov     dptr,#pc_stat
        movx    a,@dptr
        jnb     acc.1,wait_first_loop mov     dptr,#rf_dis
        clr     a
        movx    @dptr,a
        mov     r1,#input_buf
        jmp     ii
```

```
bstart:
        mov     r1,#input_buf input_loop:
                mov     dptr,#pc_stat
                movx    a,@dptr
                jnb     acc.1,input_loop
ii:
                mov     dptr,#portio
                movx    a,@dptr
                mov     @r1,a
                jnz     only1
more:
                inc     r1
                cjne    r1,#input_buf+3,input_loop
                jmp     new_pot_set only1:
                cjne    r1,#input_buf,more
                mov     a,input_buf
                jz      new_pot_set
                cjne    a,#6,$+3
                jnc     status_change
```

```
            mov    send_counter,a call   send_ad jmp    start

;

status_change:

anl    a,#7 cjne   a,#6,$+3 jc     new_setting pulse_control:

rrc    a rrc    a mov    dptr,#rf_dis movx   @dptr,a new_pot_set:

call   set_pot jmp    start new_setting:

clr    xilinx_prog clr    xilinx_reset
```

```
                nop nop nop nop anl     a,#7 mov     b,#9 mul     ab mov     dpl,#0 add     a,#20h mov     dph,a add     a,#8 mov     r4,a setb    xilinx_reset call    init_xilinx jmp     start process_kbd:

clr     kbd_flag mov     r1,#old_x wait_write:

call    chk_pc_write
```

```
            jnb    pc_wrt_flag,wait_write clr    pc_wrt_flag inc    r1 wait_write1:

call   chk_pc_write jnb    pc_wrt_flag,wait_write1 clr    pc_wrt_flag ret

;       init the xilinx chip init_xilinx:

mov    r0,#0 clr    a wait_loop:  mov    a,@r0 inc    r0 cjne   r0,#80h,wait_loop mov    r0,#0 clr    a wait_loop1: mov    a,@r0 inc    r0 cjne   r0,#80h,wait_loop1
```

```
            setb    xilinx_prog
nop
nop
nop
nop
            mov     r0,#0
            mov     p2,#80h
            clr     xilinx_cs
    xloop:  clr     a
            movc    a,@a+dptr
            mov     r2,#8
nop
nop
nop
nop
nop
    x8loop: movx    @r0,a
            nop
            nop
            nop
            nop
            rr      a
```

Appendix . page 36

```
            djnz    r2,x8loop
            inc     dptr
            mov     a,dph
            cjne    a,4,xloop
            mov     a,dpl
            cjne    a,#0bch,xloop
            movx    @r0,a
nop
nop
nop
nop
movx    @r0,a
nop
nop
nop
nop
movx    @r0,a
nop
nop
nop
nop
setb    xilinx_cs
```

```
        ret send_ad:
        call    send_preamble
        mov     a,#ad_data
        add     a,send_counter
        mov     r1,a
        dec     r1
        mov     dptr,#pc_stat
        movx    a,@dptr
        jb      acc.0,$-1
        mov     a,@r1
        mov     dptr,#ibm_wrt
        movx    @dptr,a
        ret
send_preamble:
        mov     dptr,#pc_stat
        movx    a,@dptr
        jb      acc.0,$-1
        mov     dptr,#ibm_wrt
        mov     a,#55h
        movx    @dptr,a
```

```
        mov     dptr,#pc_stat movx    a,@dptr jb      acc.0,$-1 mov     dptr,#ibm_wrt mov     a,#0aah movx    @dptr,a ret
```

;******************************************************************

*****

;   Interrpt driven routine to read the A/D

;   The data into the A/D can be one of four inputs:

;

;   0   read the x coordinates

;   1   read the y coordinates

;   2   read the fwd power

;   3   read the rev power

;   using register bank 2, dptr, psw and acc

```
ad_int:
        push    psw
        clr     rs0
        setb    rs1             ; select bank 2
        push    acc
        push    dpl
        push    dph
        mov     dptr,#ad_address
        mov     a,ad_counter
        add     a,#ad_data
        mov     r0,a            ; point to the data address
        movx    a,@dptr         ; read the a/d
        mov     @r0,a
        inc     ad_counter      ; inc the data pointer
        anl     ad_counter,#3
        setb    ad_flag
        pop     dph
        pop     dpl
        pop     acc
        pop     psw
```

```
        reti read_kbd:

mov     a,ad_data clr     c subb    a,#x_thld jnc     exit_kbd mov     a,ad_data clr     c subb    a,old_x jnc     dx_pos cpl     a dx_pos:

cjne    a,#3,$+3 jnc     new_pos mov     a,ad_data+1 clr     c subb    a,old_y jnc     dy_pos cpl     a dy_pos:

cjne    a,#3,$+3
```

```
            jc      exit_kbd
    new_pos:
            mov     old_x,ad_data
            mov     old_y,ad_data+1
            setb    kbd_flag
    exit_kbd:
    ret
    set_pot:
setb    pot_reset
nop
nop
            mov     a,new_pot1
            mov     r2,#8
            call    shift_8
            mov     a,new_pot
            mov     r2,#8
            call    shift_8
            clr     pot_reset
    ret
    shift_8:
            rlc     a
            mov     pot_data,c
```

```
        nop
        clr    pot_clk
        nop
        setb   pot_clk
        nop
        djnz   r2,shift_8
        ret chk_pc_write:
            mov    dptr,#portio
            movx   a,@dptr
            jb     acc.0,pc_exit
            mov    a,@r1
            inc    dptr
            movx   @dptr,a
            setb   pc_wrt_flag
    pc_exit:
    ret
    %include "time.asm" comm:
mov     sbuf,send_counter
reti
```

END

Appendix, page 44

```
init:   mov     sp,#60h         ;
        mov     p1,#0f7h
        anl     psw,#0e7h
        ;
        mov     tmod,#21h
        mov     th0,#252    ; set for 1 ms
        mov     tl0,#232 mov     th1,#243
        mov     tl1,#243
        mov     scon,#50h
        mov     87h,#80h
        setb    tr1 setb    it0
        setb    it1 setb    tr0 mov     r0,#0H
        clr     a clrloop: mov    @r0,a
        inc     r0
        cjne    r0,#60h,clrloop mov     10,#200
        mov     11,#5 mov     ie,#97h         ; enable xint and timer
        mov     sec_counter,#0
warmup:
        mov     a,sec_counter
        cjne    a,#2,warmup
```

Appendix , page 45

```
:020000020000FC
:10200000FF0420BAFBEEFF3FBFFFFF5FFCB3FFFFF8
:10201000B7BDFDFFFAFFFBCCF7F7FFBFFFFFE7E718
:10202000F7ED9FD9DDDBFDFDFFAFFEEAF7FFFCBF5B
:10203000FFF7EFFFDDFFFFFBFF7F3FFF777FFFFF36
:10204000FFFFF7FFF7FFFFBFFBF3F7FFFCF57FFE96
:10205000F9F9F9FB9FFDFFFBF7FFFDDFDFDFE7FF8E
:10206000FEFFFFFFFFFFFFFFEFFFFFF7FFFF77FB25
:10207000FFFFFFFFD3D7BFFFFFFF7BFFBFFFFFFF8C
:10208000FFF6FDFFEFF7FFFFFFBFBFFEF7EFFFBE5D
:10209000FEDFFDFFFFFFF7BF7FFFFF7FFFEFF7FFD3
:1020A000FFBEFFFFFBFFAFDFFBBF7F7F7FE9FFDFEF
:1020B000FFFFFFEFFFFFFFFFCF3BFFFEFFFFBFFE76
:1020C000FFDFFF77777FF7FFFFFFF57EFFFFEB3B3B
:1020D000EB3FFFFFFDF7FFF7EBF7F7FFDFFDFFFF3C
:1020E0007FF3FBFFF7FF7EFFEFFFFFFFFBFDFFFF2F
:1020F00073B7FF7BFFFFFFFFDFFFFFFBFBFFDFBDBF4
:10210000FFFFFFDFFFFF7F7FFDFE9DFFFDFDFFFE69
:10211000FFFFFFEFFFEFFCFFFFFEFFEDFDF7F7DFD47
:102120005DF7DFFFF7DFBF3FFFF2F6FFBFBFFBFF4B
:10213000DDFFFFFFFFFFFFDE7FDFFFF7F7F7F7B7D73
:10214000FFFFF7EFBFFFFDFFEDDFFFFFFBF7BFFFE
:10215000EFFBF7FEEFFAFFEFBFAFFB7FBFFFF6FF2E
:10216000F6FFFFBFBC9FEEFFFFFFFBFFFFFFFEFCC
:10217000FFFEDF7FBFAF27EFFFDF5FFAF777EFFCF0
:10218000C8DBF9F3FDFFE3BF7F77F5FEFEF65FEFF7
:10219000FFDBDFBDFEBFDFF7FFAFFBBFFFFECFDF23
:1021A000FFDFFDFFFF7AFDFDFF77DFEFDE9F9CBDC8
:1021B0002FFFDFBFBFFBFEFB7BF6F6F4BCFFFFE9A2
:1021C000DFFFFBFAFFF3F7FFFBFF77FFFEFFDFF711
:1021D000EFFBFFDFFF3F7BE76F66F6CD6DEDFEFDAA
:1021E000FEFB3ADFD5D6AEADBC7DFFEF5FED9DFFC8
:1021F000FBFFF7FFFFFFFFFFFFFFEFF9FFAFFEFBF96C
:10220000EFFFFF6777CFFF5FAFFFFFFFFF7D3FFF70
:102210003BFBFFFFF7FFFFEFFFEFFFDFDEFFFEFE01
:10222000FDFD7DFFFBEFEBDEFFFFF7EDFFDFBBFF0B
:102230003BEFF7DAFFF7FFFEFEFEDDFFFBBFF7FF28
:10224000DBBFFFF7F7FBFFBFFF7DF8FFFBFEFF7F64
:10225000EFFFFDFEEFDDFED5EBFFFF5FFF5FF777E2
:10226000AFFEAF5EFDFFBFDEF7FAFFF3FFF7FFEF54
:10227000FF7FFFDEFFFFDDBBFFD377BFBFCFFF4D8B
:10228000ECEFF6F7DFAFDFF7F7FEFF7FFA77FEFF41
:10229000FFFFFF7FFFFEBF3D3F77FFFBFFF8FDFF26
:1022A000FFEFCFD6A9FFFFFFFFBFBFFE7FEFFECE40
:1022B000D7FE56EFFFFF5FFBDFD27FEFFFFBFFF79D
:1022C000FF7FDFFFEDFF3BEEFFEEFD7F7FFE7FFB3D
:1022D00079DEFFFFFF7FFBFEFEF7FFFFFDCEFEEE1
:1022E000EEFFDFFDBBFBBF3FF7FDFEFFFDFFFEDFA7
:1022F000FFDBDFBBBFBFFFFFFFFFFFFFDEFFFEE532
:10230000DF9FFF5F7FDFBFBF9EBFEFECEDFDFBF9FF
:10231000FBFFFFF3FD7EBFFFE7FBCFDFFFFDF7FD18
:10232000FFFB5F7EFFDE7EFCBF7F73EFDFD7F3B77F
:1023300066AFEFFFF7FFFFFF8FDFFFDFBEFEBFFE1
:10234000FFFF7FF763FF8FFFFFFFFFBBBAFA3FFF7F
:10235000FFFFFEFFFFFFEFFFF7DF7D7B377FF6F626
:10236000FEFFEDEFDEEE7FE9EFD9DDD7FFA7AFA7E8
:102370007FFFEFFFFBDFCFF7AFFFFFEBF3FF3FDFA9
:102380007FFEDEFFCFCEED9FBDDB9937B737FFE78E
:10239000EFEFEE7C7F7FB3B696D6FF3D2D7D77EFD6
:1023A000FFFFDF5F7EFF6FCBAEBFEFF7B777FF7F33
```

```
:1023B000EFDEDEDFEFBDEDFDFDFFFBFB7FF7FFF79F
:1023C000EEEFFFFFFFFFFFFFFFFFBFD7DF3FFF9FBDC
:1023D000EBF3FBF7EFFFBFFBBFBFBFBFFFFFFFFFF8D
:1023E000FFFFDF5BDFDFFFBFFFF97FF7FBFFB8FF1A
:1023F000EFF7FFEFFDDFBFEFFFF7E0FFFFFFFEF7F3E
:10240000FFFFFFFF3F77FBFFFFF7FFFFFFFF77DFD8
:10241000BDBBBF7F7F7FFF7EFEFEFACFFFDFFFFFEA
:10242000FFFFFFFFFFFF77EDEEEFDBDFCFBFBFAFBB
:10243000EFBD7B7B7AFAF4F4D4E9E9E9FDDFF9FB3F
:10244000FAF5F7F7EDEBEFEFFFD4DFDFBFAF977FE4
:102450006F7FFF6FE7B6F7F7EF6FEFDFDFDEFF3B72
:1024600057DBDBBFBFBF776F735BFD7DFADFEFBF6D
:10247000EFFFFFFFBFFCEEFEFBEBF7F777EFEFEFB1
:10248000BB7FFFFFFFFDFFFDFFFFF3DFDFB7BEBC0
:10249000EBF77EF7FFFFFFFDDFDEFBFFBDF7FBFD88
:1024A000FBFBE9FFF2DFFEFF9DBFDFFFFF6FEFF7F2
:1024B000DBBFDFFFFFBFFEFFFFFF3FFFEFDFFFDF01
:1024C000EFF7EFF77EFFF56D6BA5DB5BFEFBFFF72C
:1024D000FDCFBFDDFDFFFFBBF7FFFFDF7FAFFDEDF2
:1024E000DFFFFFBDFFF7BFFEF3BFFFFFBFBFFFFE74
:1024F000FFFFFFDDD7F3FFEEFF67FFFFFBFFFFFEF0
:10250000BFFEBE7DFD75EBFF5FFFB7BFBFFEFD3FAA
:10251000DFFBFFFFFB3FFFFFF7ED7FFFD5EFFFFF87
:10252000DFF9BFBF7F4F2FD7BEFF7FEFCEF7C4E5E8
:10253000CFE9CA9DFFFDD77BF7E7FBF5DFDFFFFFA4
:10254000FF3FDF3BFEBB7FFFFEF7EEEFFFFF9DFAE
:10255000FFFBFFF7B7EFFF7FFFFEFCEFFEFFFFFD86
:10256000FFBBFFFFFB7F4FFFFFEFF7FFDDFFFFFB5
:10257000BFF7BFFFFFFDFFFBF7FFFFFFFDE7EDEF3D
:10258000DFDFFF7FDF7FFFCEFFFDFDFEFFFEFFFFF2
:10259000FFFF7EFFEFEDFFFFFFFFDFDDFFFFF37AC1
:1025A0003DFDFFBF7FFFFEFFF9FB7F7FFFFFBFF74
:1025B000FFFFFEFFFF6EDDD7FFBFFFFFFF7FF7F93
:1025C000F7AECEEEFDFDFDFBFBF9FD3FFFFFFFF794
:1025D000FFFFEEF5FFFFFDF7DBFBD7B7F7BFFB676A4
:1025E000F6FFEEEFE9E9DDD3D3A3BFA7FF7FFFEF4F
:1025F000E7FBDFDFBFF797FFFFDB7F5FF77EBEFE06
:10260000FDFDFDFF9F9FDDDD37BFBB7B6F7EF7EFDD
:102610006C737BEBD6F6F6FDFDFD7FF7D8DFBFFBD5
:10262000FFFFFFF7FFFFBFD7EFEF67DDDDA7DFBFDE
:10263000FFEFFDBFFFFFFFFFDFFFF7F574EFFFFDCB
:102640006E7FFFFFFFBFBFBD77FFE7EFFFF7F7FF2D
:10265000FF5BDBDFB7F7FFBFFFFFFFEFEFBDDFA2
:10266000FFFFFAFEFFFFFF6B7FE7FFFEBFDFEF6EAE
:10267000EFFF6FFF7F7AF7BFBFFDFED17FBFB3B61D
:10268000F13BFFFF7FEFEEFEF7DD7DDDDFFDFFFFBE
:10269000777F7FFFFEFFFBFECFFFBFFFFDFFBEFD8D
:1026A000FFFFFF77FFF7CFFFBFBFFF7F3FBFBFFB3E
:1026B000FFDAFB76B5F7EDEDFFEDDFFFFFFFF5F796
:1026C000F7EDEBFB67FFFEEFDFAF9FBF7F7FFF7F85
:1026D000FFE77FF6F6EDEDECDADBFFF93BFBD7DF4A
:1026E000BDAFAE7F7D7D5DDFFDBFFFFFDFFFFFFF85
:1026F0007FFFEDEF7FBDDDBFFFFFFFFFEFFF7FFF40
:10270000FFFFFFFFFDFFFFEFFFFBFFFFDFFFFF2D
:10271000FFFFFFFFFFFDFFFFEFDFDFFFFFBFFF7FFFA
:10272000FFFEEFFFFFFFFFFFFFBFFFF7FFFFFF12
:102730007F7FFFFFFFFFBFFFFFFFFDFFFFFFEFFB
:10274000FFFFF7FDFFEFBFDFDFF7FFBFFFFFFEFFF8B
:10275000FFFFFFFAFFDFFFDFB7FFFFFFFFFFB5B09
:10276000F6FFFFFFFFF3FFFF7FFFEFBFFEFFDFFF7F
```

Appendix page 47

```
:10277000DDFFFFFFFFFDEFFDFFFBFBFFFEFFFFEFB8
:10278000EF3FEFFFFFFFFFF7FFFFFFFFFFFEFFFD44
:10279000FDFFBFFFFFFFFFFF7FFEFFFFFFFF9DFC9
:1027A000FFFFFFBFFFFFFF7FFFCE7FFFFEFEFEEBC1
:1027B000FFFFFFFF77FFFFFFBEFBFFF7FFFFFF0D
:1027C000FBFFFFFFFFFFEFFFFFFFF5FFFFFFFFFCD
:1027D000B7EFFF7FC7FFFFEEBEFEF0FFDCFBF7F30
:1027E000FBFFF7FFFFBFFFAD7EFF7EFAFDBFFFFFE0
:1027F000FFFF6DEFFDFFDFFEDFFDFFFFFF7FFFFF50
:10280000FFF7EFFEFFFFFFFFFD3EFFFFFF7FF7FB5
:10281000FFFFFFFEFBFFDFFF3FFBFFFBFFFFEFFF10
:10282000EADBFFFF95FFDFFFFFFFFF5F57FFFFBF03
:10283000FEFFF8FFFFFDFFFFFBFFFFFF7FF7FFFF3E
:10284000FFFFC9DCFFFFB3FFBFFFFFFFFFDFEFFFAD
:10285000FFDFFFFFFDF7FFF77F7FFFFFDFFEFFEFEB
:10286000FFFFFFFFFBFBFFFF77FF7FFEFFFFFFDFA9
:10287000DDFFFFBFFFBFF3BFBFFF7FFAFBFFFFF529
:10288000FFDDFFFFFFFF6773FEFFFFFFFFFEFEEEB2
:10289000DFBD3FFFFF7FF6FFE7FF7EFEF9FDFFFF95
:1028A000FFFFFF3FBF97970FAF2F7F7E5E7EEFFD4D
:0C28B000DDDCDCB9FDBFFFFF7FFFFFFF98
:020000020000FC
:10290000FF0420BAFBEEFF3FBFFFFF5FFCBEFFFFEF
:10291000B7BDFDFFFAFFFBCCF7F7FFBFFFFFE7E70F
:10292000F7ED9FD9DDDBFDFDFFAFFEEAF7FFFCBF52
:10293000FFF7EFFFDDFFFFFBFF7F3FFF777FFFFF2D
:10294000FFFFF7FFF7FFFFBFFBF3F7FFFCF57FFE8D
:10295000F9F9F9FB9FFDFFFBF7FFFDDFDFDFE7FF85
:10296000FEFFFFFFFFFFFFFFEFFFFFF7FFFF77FB1C
:10297000FFFFFFFFD3D7BFFFFFFF7BFFFBFFFFFF83
:10298000FFF6FDFFEFF7FFFFFFBFBFFEF7EFFFBE54
:10299000FEDFFDFFFFFFF7BF7FFFFF7FFFFEFF7FFCA
:1029A000FFBEFFFFFFBFFAFDFFBBF7F7F7FE9FFDFE6
:1029B000FFFFFFEFFFFFFFFFCF3BFFFEFFFFBFFE6D
:1029C000FFDFFF77777FF7FFFFFFF57EFFFFEB3B32
:1029D000EB3FFFFFFDF7FFF7EBF7F7FDFFDFFFF33
:1029E0007F3FBFFF7FF7EFFEFFFFFFFFBFDFFFF26
:1029F00073B7FF7BFFFFFFFDFFFFFFBFBFFDFBDBEB
:102A0000FFFFFFDFFFFF7F7FFDFE9DFFFDFDFFFE60
:102A1000FFFFFFEFFFEFFCFFFFEFFEDFDF7F7DFD3E
:102A20005DF7DFFFF7DFBF3FFFF2F6FFBFBFFBFF42
:102A3000DDFFFFFFFFFFFDE7FDFFFF7F7F7B7D6A
:102A4000FFFFF7EFBFFFFFDFFEDDFFFFFFBF7BFFF5
:102A5000EFFBF7FEEFFAFFEFBFAFFB7FBFFFF6FF25
:102A6000F6FFFFBFBC9FEEFFFFFFFFBFFFFFFFEFC3
:102A7000FFFFEDF7BFBFAF27EFFFDF5FFAF777EFFCE7
:102A8000C8DBF9F3FDFFE3BF7F77F5FEFEF65FEFEE
:102A9000FFDBDFBDFEBFDFF7FFAFFBBFFFFECFDF1A
:102AA000FFDFFDFFFF7AFDFDFF77DFEFDE9F9CBDBF
:102AB0002FFFDFBFBFFBFEFB7BF6F6F4BCFFFFE999
:102AC000DFFFFBFAFFF3F7FFFBFF77FFFFEFFDFF708
:102AD000EFFBFFDFFF3F7BE76F66F6CD6DEDFEFDA1
:102AE000FEFB3ADFD5D6AEADBC7DFFEF5FED9DFFBF
:102AF000FBFFF7FFFFFFFFFFFEFF9FFAFFEFBF963
:102B0000EFFFFF6777CFFF5FAFFFFFFFFF7D3FFF67
:102B10003BFBFFFF7FFFFEFFFEFFFDFDEFFFEFEF8
:102B2000FDFD7DFFFBEFEBDEFFFFF7EDFFDFBBFF02
:102B30003BEFF7DAFFF7FFFEFEFEDDFFFBBFF7FF1F
:102B4000DBBFFFFF7F7FBFFBFFF7DF8FFFBFEFF7F5B
:102B5000EFFFFDFEEFDDFED5EBFFFF5FFF5FF777D9
```

Appendix . page 48

```
:102B6000AFFEAF5EFDFFBFDEF7FAFFF3FFF7FFEF4B
:102B7000FF7FFFDEFFFFDDBBFFD377BFBFCFFF4D82
:102B8000ECEFF6F7DFAFDFF7F7FEFF7FFA77FEFF38
:102B9000FFFFFF7FFFFEBF3D3F77FFFBFFF8FDFF1D
:102BA000FFEFCFD6A9FFFFFFFFBFBFFE7FEFFECE37
:102BB000D7FE56EFFFFF5FFBDFD27FEFFFFBFFF794
:102BC000FF7FDFFFEDFF3BEEFFEEFD7F7FFE7FFB34
:102BD00079DEFFFFFFF7FFBFEFEF7FFFFFDCEFEED8
:102BE000EEFFDFFDBBFBBF3FF7FDFEFFFDFFFEDF9E
:102BF000FFDBDFBBBFBFFFFFFFFFFFFFDEFFFEE529
:102C0000DF9FFF5F7FDFBFBF9EBFEFECEDFDFBF9F6
:102C1000FBFFFFF3FD7EBFFFE7FBCFDFFFFDF7FD0F
:102C2000FFFB5F7FFFDC7EFCBF7F73EFDFD7B3F777
:102C3000E6AFEFFFF7FFFFFFF8FDFDFFFFEFEBFF54
:102C4000FFFF7FF763EF8FFFFFFFFFBBBAFA3FFF86
:102C5000FFFFFEFFFFFFEFFFF7DF7D3B73FFFEF699
:102C6000FEFFEDEFDEEE7FEDEFD1DDD7FFA7AFA7E3
:102C70007FFFFFE7DBDFCFF7AFFFFEBF3FF3FDFC8
:102C80007FFEDEFFCFCEED9FBD9BD9B7B737FFE705
:102C9000EFEFEE7C5F5BF3B696D6FF3D2D7D77EFD1
:102CA000EFFFFF5F7EFF6FCBAEBFEFFFBF67FF7F22
:102CB000EFDEDEDFEFBDEDFDFDFFFBFB7FF7FFF796
:102CC000EEEFFFFFFFFFFFFFFFFBFD7DF3FFF9FBD3
:102CD000EBF3FBF7EFFFBFFBBFBFBFBFFFFFFFFF84
:102CE000FFFFDF5BDFDFFFBFFFF97FF7FBFFB8FF11
:102CF000EFF7FFEFFDDFBFEFFFF7E0FFFFFFEF7F35
:102D0000FFFFFFFF3F77FBFFFFF7FFFFFFFF77DFCF
:102D1000BDBBBF7F7F7FFF7FEFEFEFACFFFDFFFFFE1
:102D2000FFFFFFFFFFFFF77EDEEEFDBDFCFBFBFAFB2
:102D3000EFBD7B7B7AFAF4F4D4E9E9E9FDDFF9FB36
:102D4000FAF5F7F7EDEBEFEFFFD4DFDFBFAF977FDB
:102D50006F7FFF6FE7B6F7F7EF6FEFDFDFDEFF3B69
:102D600057DBDBBFBFBF776F735BFD7DFADFEFBF64
:102D7000EFFFFFFFBFFCEEFEFBEBF7F777EFEFEFA8
:102D8000BB7FFFFFFFFFFDFFFDFFFFF3DFDFB7BEBB7
:102D9000EBF77EF7FFFFFFFDDFDEFBFFBDF7FBFD7F
:102DA000FBFBE9FFF2DFFEFF9DBFDFFFFF6FEFF7E9
:102DB000DBBFDFFFFFBFFEFFFFFF3FFFEFDFFFDFF8
:102DC000EFF7EFF77EFFF56D6BA5DB5BFEFBFFF723
:102DD000FDCFBFDDFDFFFFBBF7FFFFDF7FAFFDEDE9
:102DE000DFFFFFBDFFF7BFFEF3BFFFFFBFBFFFFE6B
:102DF000FFFFFFDDD7F3FFEEFF67FFFFFBFFFFFEE7
:102E0000BFFEBE7DFD75EBFF5FFFB7BFBFFEFD3FA1
:102E1000DFFBFFFFFB3FFFFFF7ED7FFFD5EFFFFF7E
:102E2000DFF9BFBF7F4F2FD7BEFF7FEFCEF7C4E5DF
:102E3000CFE9CA9DFFFDD77BF7E7FBF5DFDFFFFF9B
:102E4000FF3FDF3BFEBB7FFFFEF7EEEFFFFF9FDFA5
:102E5000FFFBFFF7B7EFFF7FFFFEFCEFFEFFFFFD7D
:102E6000FFBBFFFFB7F4FFFFFEFF7FFDDFFFFFAC
:102E7000BFF7BFFFFFFDFFFBF7FFFFFFFDE7EDEF34
:102E8000DFDFFF7FDF7FFFCEFFFDFDFEFFFEFFFFE9
:102E9000FFFF7EFFEFEDFFFFFFFFDFDDFFFFF37AB8
:102EA0003DFDFFBF7FFFFEFFFF9FB7F7FFFFFBFF6B
:102EB000FFFFFEFFFF6EDDD7FFFBFFFFFFF7FF7F8A
:102EC000F7AECEEEFDFDFDFBFBF9FD3FFFFFFFF78B
:102ED000FFFFEEF5FFFFDF7DBFBD7B7F7BFFB6769B
:102EE000F6FFEEEFE9E9DDD3D3A3BFA7FF7FFFEF46
:102EF000E7FBDFDFBFF797FFFFDB7F5FF77EBEFEFD
:102F0000FDFDFDFF9F9FDDDD37BFBB7B6F7EF7EFD4
:102F10006C737BEBD6F6F6FDFDFD7FF7D8DFBFFBCC
```

Appendix, page 49

```
:102F2000FFFFFFF7FFFFBFD7EFEF67DDDDA7DFBFD5
:102F3000FFEFFDBFFFFFFFFFDFFFF7F574EFFFFDC2
:102F40006E7FFFFFFFBFBFBD77FFE7EFFFF7F7FF24
:102F5000FFF5BDBDFB7F7FBFFFFFFFFEFEFBDDF99
:102F6000FFFFFAFEFFFFFF6B7FE7FFFEBFDFEF6EA5
:102F7000EFFF6FFF7F7AF7BFBFFDFED17FBFB3B614
:102F8000F13BFFFF7FEFEEFEF7DD7DDDDFFDFFFFB5
:102F9000777F7FFFFEFFFBFECFFFBFFFFDFFBEFD84
:102FA000FFFFFF77FFF7CFFFBFBFFF7F3FBFBFFB35
:102FB000FFDAFB76B5F7EDEDFFEDDFFFFFFFF5F78D
:102FC000F7EDEBFB67FFFEEFDFAF9FBF7F7FFF7F7C
:102FD000FFE77FF6F6EDEDECDADBFFF93BFBD7DF41
:102FE000BDAFAE7F7D7D5DDFFDBFFFFFDFFFFFFF7C
:102FF0007FFFEDEF7FBDDDBFFFFFFFFFEFFF7FFF37
:10300000FFFFFFFFFFDFFFFFEFFFFBFFFFDFFFFF24
:10301000FFFFFFFFFFDFFFFEFDFDFFFFFBFFF7FFF1
:10302000FFFEEFFFFFFFFFFFFFFBFFFF7FFFFFF09
:103030007F7FFFFFFFFFFBFFFFFFFDFFFFFFEFF2
:10304000FFFFF7FDFFEFBFDFDFF7FFBFFFFFEFFF82
:10305000FFFFFFFFAFFDFFFDFB7FFFFFFFFFFFB5B00
:10306000F6FFFFFFFFF3FFFF7FFFEFBFFEFFDFFF76
:10307000DDFFFFFFFFFDEFFDFFFBFBFFFEFFFFEFAF
:10308000EF3FEFFFFFFFFFF7FFFFFFFFFFFEFFFD3B
:10309000FDFFBFFFFFFFFFFFF7FFEFFFFFFFF9DFC0
:1030A000FFFFFFBFFFFFFF7FFFCE7FFFFEFEFEEBB8
:1030B000FFFFFFFF77FFFFFFFBEFBFFFF7FFFFFF04
:1030C000FBFFFFFFFFEFFFFFFFFF5FFFFFFFFFC4
:1030D000B7EFFF7FC7FFFFFEEBEFEF0FFDCFBF7F27
:1030E000FBFFF7FFFFBFFFAD7EFF7EFAFDBFFFFFD7
:1030F000FFFF6DEFFDFFDFFEDFFDFFFFFF7FFFFF47
:10310000FFF7FEFFEFFFFFFFFFD3EFFFFFF7FF7FAC
:10311000FFFFFFEFBFFFDFFF3FFBFFFBFFFFEFFF07
:10312000EADBFFFF95FFDFFFFFFFFF5F57FFFFBFFA
:10313000FEFFF8FFFFFDFFFFFBFFFFFF7FF7FFFF35
:10314000FFFFC9DCFFFFB3FFBFFFFFFFFFDFEFFFA4
:10315000FFDFFFFFFDF7FFF77F7FFFFFDFFEFFEFE2
:10316000FFFFFFFFFBFBFFFF77FF7FFEFFFFFFDFA0
:10317000DDFFFFBFFFBFF3BFBFFF7FFAFBFFFFF520
:10318000FFDDFFFFFFFF6773FEFFFFFFFFFEFEEEA9
:10319000DFBD3FFFFF7FF6FFE7FF7EFEF9FDFFFF8C
:1031A000FFFFFF3FBF97970FAF2F7F7E5E7EEFFD44
:0C31B000DDDCDCB9FDBFFFFF7FFFFFFF8F
:020000020000FC
:10320000FF0420BAFBEEFF3FBFFFFF5FFCBEFFFFE6
:10321000B7BDFDFFFAFFFBCCF7F7FFBFFFFFE7E706
:10322000F7ED9FD9DDDBFDFDFFAFFEEAF7FFFCBF49
:10323000FFF7EFFFDDFFFFFBFF7F3FFF777FFFFF24
:10324000FFFFF7FFF7FFFFBFFBF3F7FFFCF57FFE84
:10325000F9F9F9FB9FFDFFFBF7FFFDDFDFDFE7FF7C
:10326000FEFFFFFFFFFFFFFEFFFFFF7FFFF77FB13
:10327000FFFFFFFFD3D7BFFFFFFF7BFFFBFFFFFF7A
:10328000FFF6FDFFEFF7FFFFFFBFBFFEF7EFFFBE4B
:10329000FEDFFDFFFFFFF7BF7FFFFF7FFFEFF7FFC1
:1032A000FFBEFFFFFFBFFAFDFFBBF7F7F7FE9FFDFDD
:1032B000FFFFFFEFFFFFFFFFCF3BFFFEFFFFBFFE64
:1032C000FFDFFF77777FF7FFFFFFF57EFFFFEB3B29
:1032D000EB3FFFFFFFDF7FFF7EBF7F7FFDFFDFFFF2A
:1032E0007FF3FBFFF7FF7EFFEFFFFFFFFBFDFFFF1D
:1032F00073B7FF7BFFFFFFFDFFFFFFBFBFFDFBDBE2
:10330000FFFFFFDFFFFF7F7FFDFE9DFFFDFDFFFE57
```

Appendix . page 50

```
:10331000FFFFFFEFFFEFFCFFrFEFFEDFDF7F7DFD35
:103320005DF7DFFFF7DFBF3FFFF2F6FFBFBFFBFF39
:10333000DDFFFFFFFFFFFDE7FDFFFF7F7F7F7B7D61
:10334000FFFFF7EFBFFFFFDFFEDDFFFFFFBF7BFFEC
:10335000EFFBF7FEEFFAFFEFBFAFFB7FBFFFF6FF1C
:10336000F6FFFFFBEBC9FEEFFFFFFFFBFFFFFFEFBB
:10337000FFFEDF7FBFAF27EFFFDF5FFAF777EFFCDE
:10338000C8DBF9F3FDFFE3BF7F77F5FEFEF65FEFE5
:10339000FFDBDFBDFEBFDFF7FFAFFBBFFFFECFDF11
:1033A000FFDFFDFFFF7AFDFDFF77DFEFDE9F9CBDB6
:1033B0002FFFDFBFB7FBFEFB7BF6F6F4BCFFFFE998
:1033C000DFFFFBFAFFF3F7FFFBFF77FFFEFFDFF7FF
:1033D000EFFBFFDFEF3F7BE76F66F6CD6DEDFEFDA8
:1033E000FEFB3ADFD5D6AEADBC7DFFEF5BED9DFFBA
:1033F000FBFFF7FFFFFFFFFFDFEFF9FFAFFEFBF97A
:10340000EFFFFF6777CFFF5FAFFFFFFFFFF7D3FFF5E
:103410003BFBFFFFF7FFFEFFFEFFFDFDEFFFEFEEF
:10342000FDFD7DFFFBEFEBDEFFFFF7EDFFDFBBFFF9
:103430003BEFF7DAFFF7FFFEFEFEDDFFFBBFF7FF16
:10344000DBBFFFF7F7FBFFBFFF7DF8FFFBFEFF7F52
:10345000EFFFFDFEEFDDFED5EBFFFF5FFF5FF777D0
:10346000AFFEAF5EFDFFBFDEF7FAFFF3FFF7FFEF42
:10347000FF7FFFDEFFFFDDBBFFD377BFBFCFFE4D7A
:10348000ECEFF6F7DFAFDFF7B7FEFF7FFA77FEFF6F
:10349000FFFFFF7FFF7FBFBF3F77FFFBFFF8FDFF11
:1034A000FFFFCFD6A9FFFFFFFBFBFEF7FEFFECE2D
:1034B000D7FE56EFFFFFDFFADFD27FEFFFFBFFF70C
:1034C000FF7FD9FFEDFF3BEEFFEEFD7F7FFE7FFB31
:1034D00079DEFFFFFFFF7F7BFEFEF7FFFFFDCEFEED7
:1034E000EEFFDFFDBBFBBF3FF7FDFEFFFDFFFEDF95
:1034F000FFDBDFBBBFBFFFFF7F7FFFFFDEFFFEE520
:10350000DF9FFF5FFBDBBFBF9EBFEFECEDFDFBFD71
:10351000FBF7FFF3FD7EBFFFE7FBEFFBBBFDF7FD16
:10352000FFFB5F7EFFDC7E7EBD7F73EFDFD7F3B7EF
:10353000E6AFE7EFF7FFFFFFF8FDFFFDFFABEBFFA7
:10354000FFFF7FF763FF8FFFFFFFFFBBBAFA3FFF6D
:10355000FFFFFEFFFFFFFEFFFF7DF7D7B37FF7E768C
:10356000F6FFEDEFDEEE7FE9EFD1DDDFB7A7AFA726
:103570007FFFEFFFDBDFEBB7AFFFFFEBF3FF3FDFDB
:103580007FFEDFFDCFCEED9FBDDB99B7B7376FE78D
:10359000EFEFEE7C7F7FF3B696D6FD3D2D7D77EF86
:1035A000FFFFFF5F5CFF6FCBAEBFEFF7B767EF7E4C
:1035B000EFDEDEDFEFBDEDFDFDFFFBFB7FF7FFF78D
:1035C000EEEFFFFFFFFFFFFFFFFBFD7DF3FFF9FBCA
:1035D000EBF3FBF7EFFFBFFBBFBFBFBFFFFFFFFF7B
:1035E000FFFFDF5BDFDFFFBFFFF97FF7FBFFB8FF08
:1035F000EFF7FFEFFDDFBFEFFFF7E0FFFFFFEF7F2C
:10360000FFFFFFFF3F77FBFFFFF7FFFFFFFF77DFC6
:10361000BDBBBF7F7F7FFF7EFEFEFACFFFDFFFFFD8
:10362000FFFFFFFFFFFF77EDEEEFDBDFCFBFBFAFA9
:10363000EFBD7B7B7AFAF4F4D4E9E9E9FDDFF9FB2D
:10364000FAF5F7F7EDEBEFEFFFD4DFDFBFAF977FD2
:103650006F7FFF6FE7B6F7F7EF6FEFDFDFDEFF3B60
:1036600057DBDBBFBFBF776F735BFD7DFADFEFBF5B
:103670000EFFFFFFBFFCEEFEFBEBF7F777EFEFEF9F
:10368000BB7FFFFFFFFFDFFFDFFFFF3FDFDFB7BEBAE
:10369000EBF77EF7FFFFFFFFDDFDEFBFFBDF7FBFD76
:1036A000FBFBE9FFF2DFFEFF9DBFDFFFFF6FEFF7E0
:1036B000DBBFDFFFFFBFFEFFFFFF3FFFEFDFFFDFEF
:1036C000EFF7EFF77EFFF56D6BA5DB5BFEFBFFF71A
```

Appendix, page 51

```
:1036D000FDCFBFDDFDFFFFBBF7FFFFDF7FAFFDEDE0
:1036E000DFFFFFBDFFF7BFFEF3BFFFFFBFBFFFFE62
:1036F000FFFFFFDDD7F3FFEEFF67FFFFFBFFFFFEDE
:10370000BFFEBE7DFD75EBFF5FFFB7BFBFFEFD3F98
:10371000DFFBFFFFFB3FFFFFF7ED7FFFD5EFFFFF75
:10372000DFF9BFBF7F4F2FD7BEFF7FEFCEF7C4E5D6
:10373000CFE9CA9DFFFDD77BF7E7FBF5DFDFFFFF92
:10374000FF3FDF3BFEBB7FFFFEF7EEEFFFFF9FDF9C
:10375000FFFBFFF7B7EFFF7FFFFEFCEFFEFFFFFD74
:10376000FFFBBFFFFFB7F4FFFFFEFF7FFDDFFFFFA3
:10377000BFF7BFFFFFFDFFFBF7FFFFFFFDE7EDEF2B
:10378000DFDFFF7FDF7FFFCEFFFDFDFEFFFEFFFFE0
:10379000FFFF7EFFEFEDFFFFFFFFFDFDDFFFFF37AAF
:1037A0003FDFFBF7FFFFEFFFF9FB7F7FFFFFFBFF62
:1037B000FFFFFEFFFF6EDDD7FFFBFFFFFFFF7FF7F81
:1037C000F7AECEEEFDFDFDFBFBF9FD3FFFFFFFF782
:1037D000FFFFEEF5FFFFDF7DBFBD7B7F7BFFB67692
:1037E000F6FFEEEFE9E9DDD3D3A3BFA7FF7FFFEF3D
:1037F000E7FBDFDFBFF797FFFFDB7F5FF77EBEFEF4
:10380000FDFDFDFF9F9FDDDD37BFBB7B6F7EF7EFCB
:103810006C737BEBD6F6F6FDFDFD7FF7D8DFBFFBC3
:10382000FFFFFFF7FFFFBFD7EFEF67DDDDA7DFBFCC
:10383000FFEFFDBFFFFFFFFFDFFFF7F574EFFFFDB9
:103840006E7FFFFFFFBFBFBD77FFE7EFFFF7F7FF1B
:10385000FFF5BDBDFB7F7FFBFFFFFFFEFEFBDDF90
:10386000FFFFFAFEFFFFFF6B7FE7FFFEBFDFEF6E9C
:10387000EFFF6FFF7F7AF7BFBFFDFED17FBFB3B60B
:10388000F13BFFFF7FEFEEFEF7DD7DDDDFFDFFFFAC
:10389000777F7FFFFEFFFBFECFFFBFFFFDFFBEFD7B
:1038A000FFFFFF77FFF7CFFFBFBFFF7F3FBFBFFB2C
:1038B000FFDAFB76B5F7EDEDFFEDDFFFFFFFF5F784
:1038C000F7EDEBFB67FFFEEFDFAF9FBF7F7FFF7F73
:1038D000FFE77FF6F6EDEDECDADBFFF93BFBD7DF38
:1038E000BDAFAE7F7D7D5DDFFDBFFFFFDFFFFFFF73
:1038F0007FFFEDEF7FBDDDBFFFFFFFFFEFFF7FFF2E
:10390000FFFFFFFFFDFFFFFEFFFFBFFFFDFFFFF1B
:10391000FFFFFFFFFFFDFFFFEFDFDFFFFFBFFF7FFE8
:10392000FFFEEFFFFFFFFFFFFFFFBFFF7FFFFFF00
:103930007F7FFFFFFFFFBFFFFFFFFDFFFFFEFE9
:10394000FFFFF7FDFFEFBFDFDFF7FFBFFFFFEFFF79
:10395000FFFFFFFFAFFDFFFDFB7FFFFFFFFFFB5BF7
:10396000F6FFFFFFFFF3FFFF7FFFEFBFFEFFDFFF6D
:10397000DDFFFFFFFFFDEFFDFFFBFBFFFEFFFFEFA6
:10398000EF3FEFFFFFFFFFFF7FFFFFFFFFFEFFFD32
:10399000FDFFBFFFFFFFFFFFF7FFEFFFFFFFF9DFB7
:1039A000FFFFFFBFFFFFFFF7FFFCE7FFFFEFEFEEBAF
:1039B000FFFFFFFF77FFFFFFFBEFBFFFF7FFFFFFFB
:1039C000FBFFFFFFFFFFEFFFFFFFF5FFFFFFFFFBB
:1039D000B7EFFF7FC7FFFFFEEBEFEF0FFDCFBF7F1E
:1039E000FBFFF7FFFFBFFFAD7EFF7EFAFDBFFFFFCE
:1039F000FFFF6DEFFDFFDFFEDFFDFFFFFF7FFFFF3E
:103A0000FFF7FEFFEFFFFFFFFD3EFFFFFF7FF7FA3
:103A1000FFFFFFEFBFFDFFF3FFBFFFBFFFFEFFFFE
:103A2000EADBFFFF95FFDFFFFFFFFF5F57FFFFBFF1
:103A3000FEFFF8FFFFDFFFFFBFFFFF7FF7FFFF2C
:103A4000FFFFC9DCFFFFB3FFBFFFFFFFFDFEFFF9B
:103A5000FFDFFFFFFDF7FFF77F7FFFFFDFFEFFEFD9
:103A6000FFFFFFFFFBFBFFFF77FF7FFEFFFFFFDF97
:103A7000DDFFFFBFFFBFF3BFBFFF7FFAFBFFFFF517
:103A8000FFDDFFFFFFFF6773FEFFFFFFFFFFEFEEEA0
```

Appendix, page 52

```
:103A9000DFBD3FFFFF7FF6FFE7FF7EFEF9FDFFFF83
:103AA000FFFFFF3FBF97970FAF2F7F7E5E7EEFFD3B
:0C3AB000DDDCDCB9FDBFFFFF7FFFFFFF86
:020000020000FC
:103B0000FF0420BAFBEEFF3FBFFFFF5FFCBEFFFFDD
:103B1000B7BDFDFFFAFFFBECF7F7FFBFFFFFE7E7DD
:103B2000F7ED8FD9DDDBFDFDFFAFFEEAF7FFFCBF50
:103B3000FFF7EFFFDDFFFFFBFF7F3FFF777FFFFF1B
:103B4000FFFFF7FFF7DFDFAFFBF3F7FFFCF57FFECB
:103B5000F9F9FB9FFDFFFBF7FFFDDFDFDFE7FE74
:103B6000FEFFFFFFFFFFFFFEFFFFFF7FFFF77FB0A
:103B7000FFFFFFFFD3D7BFFFFFFF7BFFFBFFFFFF71
:103B8000FFF6FDFFEFF7FFFFFFBFBFFEF7EFFFBE42
:103B9000FEDFFDFFFFFFF7BF7FFFFF7FFFEFF7FFB8
:103BA000FFBEFFFFFBFFAFDFFBBF7F7F7FE9FFDFD4
:103BB000FFFFFFEFFFFFFFFFCF3BFFFEFFFFBFFE5B
:103BC000FFDFFF77777FF7FFFFFFF57EFFFFEB3B20
:103BD000EB3FFFFFFFDF7FFF7EBF7F7FFDFFDFFFF21
:103BE0007FF3FBFFF7FF7EFFEFFFFFFFFBFDFFFF14
:103BF00073B7FF7BFFFFFFFFDFFFFFFBFBFFDFBDBD9
:103C0000FFFFFDFFFFF7F7FFDFE9DFFFDFDFFFE4E
:103C1000FFFFFFEFFFFEFFCFFFFEFFEDFDF7F7DFD2C
:103C20005DF7DFFFF7DFBF3FFFFF3F6FFBFBFFBFF2F
:103C3000DDFFFFFFFFFFFFDE7FDFFFF7F7F7FFB7DD8
:103C4000FFFFF7EFBFFFFFDFFEDDFFFFFFBF7BFFE3
:103C5000EFFBF7FEEFFAFFEFBFAFFB7FDFFFF6FFF3
:103C6000F6FFFEBFBC9FEEFFFFFFFBFFFFFFEFB2
:103C7000FFFEDF77BFAF37FFFFFF5FFAF777EFFC9D
:103C8000C8DBF9F3FFFDE3BF7F77F7FEFEF65FFFCA
:103C9000FFDBDFBDFEBFDFF/FFBFFBBFFFFECFDFF8
:103CA000FFDFFDFFFFFAFDFDFF77DFEFDE9F9CBD2D
:103CB0002FFFDFBFB7FBFEFB7BF6F6F4BCFFFFE98F
:103CC000DFFFFBFAFFF3F7FFFBFF77FFFFEFFDFF7F6
:103CD000EFFBFFCFFF3F7BE76F66F6CD6DEDFEFF9D
:103CE000FEFB3ADFD5D6AEADBC7DFFEB5BED9DFFB5
:103CF000FBFFF7FFFFFFFFFFDFEFF9FFAFFEFBF971
:103D0000EFFFFF6777CFFF5FAFFFFFFFFF7D3FFF55
:103D10003BFBFFFFF7FFFFFFEFFFDFDEFFFEED6
:103D2000FDFDFDFFFBEFEBDEFFEFF7EDFFFFFFFF1C
:103D30003BEFF7DAFFF7FFFEFEFEDDFFFBBFF7FF0D
:103D4000DABFFFF7F7FFFBBFFF7DF8FFFBFEFF7F4A
:103D5000FFFFFDFEEFDDFED5EBFFFFFFFF5FF77717
:103D6000AFFEAF5EFDFFFFDFF7FAFFF3FFF7FEFF8
:103D7000FF7FFEDEFFFFDDBBFFD377BFFF7FFF4D81
:103D8000ECEFF6F7DFAFDFF7B7FFFFF7FFA77FEFF65
:103D9000FFFFFFFF7FFFBFBF3F77FFFBFFF8FDFF88
:103DA000F7FFCFD6A9FFFFFFFFBFBFFF7FEFFECE1C
:103DB000D7FE56EFFFFFFFFFFDFD27FEFFFFBFFF7DE
:103DC000FFFFDDFFEDFF3BEEFFEEFD7F7FFE7FFBA4
:103DD00079DEFBFBFFF7F7BFFFEF7FFFFFDCEFEEC6
:103DE000EEFFDFFDFBFBBF3FF7FDFEFFFDFFFEDF4C
:103DF000FFDBDFBBBFBBFFFF7FFFFFFFDEFFFEE59B
:103E0000DF9FFF5FFBDFBFBF9EBFEFECEFFDFFFD5E
:103E1000FFFFFFF3FD7EBFFFE7FBEFFBFFFDF7FDBD
:103E2000FFFB5F6FFFDE7EFDFF7F73EFDFD7F7F7EE
:103E30006EAFC78FF7FFFFFFFF8FDFDFFFBAB6BFF1A
:103E4000FFFF7FF763EF8FFFFFFDFBBBBAFA3FFF7A
:103E5000FFFFFEFFFFFFFFFFF7DF7D3B737F76F67F
:103E6000FEFDEDEFDEEE7FEDEFD9DDD7BBA6AFA710
:103E70007FFFEFE7DBDFCFB7AFFFFFEBF3EF37DF1E
```

Appendix, page 53

```
:103E80006FDEFEFDCFCEED9FBDDBD9B7B7376FE755
:103E9000EFEFEE7C5F5BB3B29656FD3D2D7D77EF85
:103EA000FFFFFF5F7EFF6FCBAEBFEF77BF67EF7E99
:103EB000EFD6DEDFEFBDEDFDFDFFFBFB7FF7FFF78C
:103EC000EEEFFFFFFFFFFFFFFFFBFD7DF3FFF9FBC1
:103ED000EBF3FBF7EFFFBFFBBFBFBFBFFFFFFFFF72
:103EE000FFFFDF5BDFDFFFBFFFF97FF7FBFFB8FFFF
:103EF000EFF7FFEFFDDFBFEFFFF7E0FFFFFFEF7F23
:103F0000FFFFFFFF3F77FBFFFFF7FFFFFFFF77DFBD
:103F1000BDBBBF7F7F7FFF7EFEFE7ACFFFDFFFFF4F
:103F2000FFFFFFFFFFFF77EDEEEFDBDFCFBFB7AFA8
:103F3000EFBD7B7B7AFAF4F4D4E9E9E9FDDFF9FB24
:103F4000FAF5F7F7EDEBEFEFFFD4DFDFBFAF977FC9
:103F50006F7FFF6FE7B6F7F7EF6FEFDFDFDEFF3B57
:103F600057DBDBBFBFBF776F735BFD7DFADFEFBF52
:103F7000EFFFFFFFBFFCEEFEFBEBF7F777EFEFEF96
:103F8000BB7FFFFFFFFFDFFFDFFFFF3DFDFB7BEBA5
:103F9000EBF77EF7FFFFFFFFDDFDEFBFFBDF7FBFD6D
:103FA000FBFBE9FFF2DFFEFF9DBFDFFFFF6FEFF7D7
:103FB000DBBFDFFFFFBFFEFFFFFF3FFFEFDFFFDFE6
:103FC000EFF7EFF77EFFF56D6BA5DB5BFEFBFFF711
:103FD000FDCFBFDDFDFFFFBBF7FFFFDF7FAFFDEDD7
:103FE000DFFFFFBDFFF7BFFEF3BFFFFFBFBFFFFE59
:103FF000FFFFFFDDD7F3FFEEFF67FFFFFBFFFFFED5
:10400000BFFEBE7DFD75EBFF5FFFB7BFBFFEFD3F8F
:10401000DFFBFFFFFFB3FFFFFF7ED7FFFD5EFFFFF6C
:10402000DFF9BFBF7F4F2FD7BEFF7FEFCEF7C4E5CD
:10403000CFE9CA9DFFFDD77BF7E7FBF5DFDFFFFF89
:10404000FF3FDF3BFEBB7FFFFEF7EEEFFFFF9FDF93
:10405000FFFBFFF7B7EFFF7FFFFEFCEFFEFFFFFD6B
:10406000FFFBBFFFFFB7F4FFFFFEFF7FFDDFFFFF9A
:10407000BFF7BFFFFFFDFFFBF7FFFFFFFDE7EDEF22
:10408000DFDFFF7FDF7FFFCEFFFDFDFEFFFEFFFFD7
:10409000FFFF7EFFEFEDFFFFFFFFDFDDFFFFF37AA6
:1040A0003DFDFFBF7FFFFEFFFF9FB7F7FFFFFBFF59
:1040B000FFFFFEFFFF6EDDD7FFFBFFFFFFF7FF7F78
:1040C000F7AECEEEFDFDFDFBFBF9FD3FFFFFFFF779
:1040D000FFFFEEF5FFFFDF7DBFBD7B7F7BFFB67689
:1040E000F6FFEEEFE9E9DDD3D3A3BFA7FF7FFFEF34
:1040F000E7FBDFDFBFF797FFFFDB7F5FF77EBEFEEB
:10410000FDFDFDFF9F9FDDDD37BFBB7B6F7EF7EFC2
:104110006C737BEBD6F6F6FDFDFD7FF7D8DFBFFBBA
:10412000FFFFFFF7FFFFBFD7EFEF67DDDDA7DFBFC3
:10413000FFEFFDBFFFFFFFFFDFFFF7F574EFFFFDB0
:104140006E7FFFFFFFBFBFBD77FFE7EFFFF7F7FF12
:10415000FFF5BDBDFB7F7FBFFFFFFFFEFEFBDDF87
:10416000FFFFFAFEFFFFFF6B7FE7FFFEBFDFEF6E93
:10417000EFFF6FFF7F7AF7BFBFFDFED17FBFB3B602
:10418000F13BFFFF7FEFEEFEF7DD7DDDDFFDFFFFA3
:10419000777F7FFFFEFFFBFECFFFBFFFFDFFBEFD72
:1041A000FFFFFF77FFF7CFFFBFBFFF7F3FBFBFFB23
:1041B000FFDAFB76B5F7EDEDFFEDDFFFFFFFF5F77B
:1041C000F7EDEBFB67FFFEEFDFAF9FBF7F7FFF7F6A
:1041D000FFE77FF6F6EDEDECDADBFFF93BFBD7DF2F
:1041E000BDAFAE7F7D7D5DDFFDBFFFFFDFFFFFF6A
:1041F0007FFFEDEF7FBDDDBFFFFFFFFFEFFF7FFF25
:10420000FFFFFFFFFDFFFFFEFFFFBFFFFDFFFFF12
:10421000FFFFFFFFFFDFFFFEFDFDFFFFFBFFF7FFDF
:10422000FFFEEFFFFFFFFFFFFFBFFFF7FFFFFFF7
:104230007F7FFFFFFFFFFFBFFFFFFFFDFFFFFEF50
```

Appendix, page 54

```
:10424000FFFFF7FDFFEFBFDFDFF7FFBFFFFFEFFF7C
:10425000FFFFFFFFAFFDFFFDFB7FFFFFFFFFFB5BEE
:10426000F6FFFFFFFFF3FFFF7FFFEFBFFEFFDFFF64
:10427000DDFFFFFFFFFDEFFDFFFBFBFFFEFFFFEF9D
:10428000EF3FEFFFFFFFFF7FFFFFFFFFFFEFFFD29
:10429000FDFFBFFFFFFFFFFFF7FFEFFFFFFFF9DFAE
:1042A000FFFFFFBFFFFFFFF7FFFCE7FFFFEFEFEEBA6
:1042B000FFFFFFFF77FFFFFFFBEFBFFFF7FFFFFFF2
:1042C000FBFFFFFFFFFFFEFFFFFFFF5FFFFFFFFFB2
:1042D000B7EFFF7FC7FFFFFEEBEFEF0FFDCFBF7F15
:1042E000FBFFF7FFFFBFFFAD7EFF7EFAFDBFFFFFC5
:1042F000FFFF6DEFFDFFDFFEDFFDFFFFFF7FFFFF35
:10430000FFF7FEFFEFFFFFFFFFD3EFFFFFF7FF7F9A
:10431000FFFFFFEFBFFFDFFF3FFBFFFBFFFFEFFFF5
:10432000EADBFFFF95FFDFFFFFFFFF5F57FFFFBFE8
:10433000FEFFF8FFFFFDFFFFFBFFFFFF7FF7FFFF23
:10434000FFFFC9DCFFFFB3FFBFFFFFFFFFDFEFFF92
:10435000FFDFFFFFFFDF7FFF77F7FFFFFDFFEFFEFD0
:10436000FFFFFFFFFBFBFFFF77FF7FFEFFFFFFDF8E
:10437000DDFFFFBFFFFBFF3BFBFFF7FFAFBFFFFF50E
:10438000FFDDFFFFFFFFF6773FEFFFFFFFFFEFEEE97
:10439000DFBD3FFFFFF7FF6FFE7FF7EFEF9FDFFFF7A
:1043A000FFFFFF3FBF97970FAF2F7F7E5E7EEFFD32
:0C43B000DDDCDCB9FDBFFFFF7FFFFFFF7D
:020000020000FC
:10440000FF0420BAFBEEFF3FBFFFFF5FFCBEFFFFD4
:10441000B7BDFDFFFAFFFBECF7F7FFBFFFFFE7E7D4
:10442000F7ED8FD9DDDBFDFDFFAFFEEAF7FFFCBF47
:10443000FFF7EFFFDCFFFFFBFF7F3FFF777FFFFF13
:10444000F7FBF7F7F7DFDFAFFBF3F7FFFCF57FFED6
:10445000F9F9FB9FFDFFFBF7FBFDDDDFDFE7FE71
:10446000FEFFFDFFFFFFFFFFEFFFFFF7FFFF77FB21
:10447000FFFFFFFFD3D7BFFFFFFF7BFFFBFFFFFF68
:10448000FFF6FDEFEFF7FFFFBFBFBFFEF7EFFFBE89
:10449000FEDFFDFFFFFFF7BF7FFFFF7FFFFEFF7FFAF
:1044A000FFBEFFFFFBFFAFDFFBBF7F7F7FE9FFDFCB
:1044B000FFFFFFFEFFFFFFFFFCF3BFFFEFFFFBFFE52
:1044C000FFDFFFF77777FF7FFFFFFF57EFFFFEB3B17
:1044D000EB3FFFFFFDF7FFF7EBF7F7FFDFFDFFFF18
:1044E0007FF3FBFFF7FF7EFFEFFFFFFFFBFDFFFF0B
:1044F00073B7FF7BFFFFFFFDFFFFFFBFBFFDFBDBD0
:10450000FFFFFDFFFF7F7FFDFE9DFFFDFDFFFE45
:10451000FFFFFFEFFFEFFCFFFFEFFEDFDF7F7DFD23
:104520005DF7DFFFF7DFBF3FFFF3F6FFBFBFFBFF26
:10453000DDFFFFFFFFFFFFDE7FDFFFF7F7F7B7D4F
:10454000FFFFF7EFBFFFFFDFFEDDFFFEFFBF7BFFDB
:10455000EBFBF7FEEFFAFFEFBFAFFB7FDFFFF6FFEE
:10456000B6FFFFBFBC9FEEFFFFFFFFBFFFFFFFEFE8
:10457000FFFEDF77BFAF37FFFFFF5FFAF777EFFC94
:10458000C8DBF9D1FFFDE3BF7F77F7FEFEF65FFFE3
:10459000FFDBDFBDFEBFDFF7FFBFFBBFFFFECFDFEF
:1045A000FFDFFDFFFF7AFDFDFF77DFEFDE9F9CBDA4
:1045B0002FFFDFBFB7FBFEFB7BF6F6F4BCFFFFE986
:1045C000DFFFFBFAFFF3F7FFFBFF77FFFEFFDFF7ED
:1045D000EFFBFFCFFF3F7BE76F66F6CD6DEDFEFF94
:1045E000FEFB3ADFD5D6AEADBC7DFFEB5BED9DFFAC
:1045F000FBFFF7FFFFFFFFFFDFEFF9FFAFFEFBF968
:10460000EFFFFF6777CFFF5FAFFFFFFFFF7D3FFF4C
:104610003BFBFFFFF7FFFFFFFEFFFDFDEFDFEFECF
:10462000FDFDFDFFFBEFEBDEFFEFF7EDFFFFFFFF13
```

```
:104630003BEFF7DAFFF7FFFEFEFEDDFFFBBFF7FF04
:10464000DABFFFF777FFFBBFFF7DF8FFFBFEFF7FC1
:10465000EFFFFDFEEFDDFED5EBFFFF77FF5FF777A6
:10466000AFFEAF5EFDFFBFDFF7FAFFF3FFF7FFEF2F
:10467000FF7FFFDEFFFFDDBBFFD377BFBFFFFE4D38
:10468000ECEFF6F7DFAFDFF737FBFF7FFA77FEFFE0
:10469000FFFFFF7FFBFFBFBF3F77FFFBFFF8FDDFA3
:1046A000FFFFCFD6A9FFFFFFFFBFBFE67FEFFECE24
:1046B000D7FE56EFFFFFDFFFDFD27FEFFFFBFFF7F5
:1046C000FFFFD9FFEDFF3BEEFFEEFD7F7FFE7FFB9F
:1046D00079DEFFFBFFF7FFBFFFEF7FFFFFDCEFEEB1
·1046E000EEFFDFFDBBFBBF3FF7FDFEFFFDFFFEDF83
:1046F000FFDBDFBBBFBFFFFFFFFFFFFFDEFFFEE50E
:10470000DF9FFF5FFFDFBEBF9EBFEFECEDFDFBF95C
:10471000FFF7FFF3FD7EBFFFE7FBCFFFBFFDF7FD18
:10472000FFFB5F6EFFDC7EFDFD7F73EFDFD7F3F7EE
:10473000E6AFC7DFF6FFFFFFF8FDFFFFFFAFEBF7C8
:10474000FFFF7FF763FF8FFFFFFDFFBBBAFA3FFF5D
:10475000FFFFFEFFFFFFFFFFF7DF7D7B77FFFEF62A
:10476000FE7CEDEFDEEE7FE9EFD3DDD7BFA7AFA78D
:104770007FFFEFEFDBDFCFF7AFFFFFEBF3EF3FDFC5
:104780007FFEFEFDCFCEED9FBDDBD9B7B7376FE61D
:10479000EFEFEE7C7F5BF3B696D6FD3D2D7D77EF98
:1047A000FFFFFF5F7EFF6FCBAEBFEFF7BF67FF7FFF
:1047B000CFD6DEDFEFBDEDFDFDFFFBFB7FF7FFF7A3
:1047C000EEEFFFFFFFFFFFFFFFFBFD7DF3FFF9FBB8
:1047D000EBF3FBF7EFFFBFFFBBFBFBFFFFFFFFFF69
:1047E000FFFFDF5BDFDFFFBFFFF97FF7FBFFB8FFF6
:1047F000EFF7FFEFFDDFBFEFFFF7E0FFFFFFEF7F1A
:10480000FFFFFFFF3F77FBFFFFF7FFFFFFFF77DFB4
:10481000BDBBBF7F7F7FFF7EFEFE7ACFFFDFFFFF46
:10482000FFFFFFFFFFFFFF77EDEEEFDBDFCFBFB7AF9F
:10483000EFBD7B7B7AFAF4F4D4E9E9E9FDDFF9FB1B
:10484000FAF5F7F7EDEBEFEFFFD4DFDFBFAF977FC0
:104850006F7FFF6FE7B6F7F7EF6FEFDFDFDEFF3B4E
:1048600057DBDBBFBFBF776F735BFD7DFADFEFBF49
:10487000EFFFFFFFFBFFCEEFEFBEBF7F777EFEFEF8D
:10488000BB7FFFFFFFFFDFFFDFFFFF3DFDFB7BEB9C
:10489000EBF77EF7FFFFFFFDDFDEFBFFBDF7FBFD64
:1048A000FBFBE9FFF2DFFEFF9DBFDFFFFF6FEFF7CE
:1048B000DBBFDFFFFFBFFEFFFFFF3FFFEFDFFFDFDD
:1048C000EFF7EFF77EFFF56D6BA5DB5BFEFBFFF708
:1048D000FDCFBFDDFDFFFFBBF7FFFFDF7FAFFDEDCE
:1048E000DFFFFFBDFFF7BFFEF3BFFFFFBFBFFFFE50
:1048F000FFFFFFDDD7F3FFEEFF67FFFFFBFFFFFECC
:10490000BFFEBE7DFD75EBFF5FFFB7BFBFFEFD3F86
:10491000DFFBFFFFFB3FFFFFF7ED7FFFD5EFFFFF63
:10492000DFF9BFBF7F4F2FD7BEFF7FEFCEF7C4E5C4
:10493000CFE9CA9DFFFDD77BF7E7FBF5DFDFFFFF80
:10494000FF3FDF3BFEBB7FFFFEF7EEEFFFFF9FDF8A
:10495000FFFBFFF7B7EFFF7FFFFEFCEFFEFFFFFD62
:10496000FFFBBFFFFFB7F4FFFFFEFF7FFDDFFFFF91
:10497000BFF7BFFFFFFDFFFBF7FFFFFFFDE7EDEF19
:10498000DFDFFF7FDF7FFFCEFFFDFDFEFFFEFFFFCE
:10499000FFFF7EFFEFEDFFFFFFFFDFDDFFFFF37A9D
:1049A0003DFDFFBF7FFFFEFFFF9FB7F7FFFFFBFF50
:1049B000FFFFFEFFFF6EDDD7FFFBFFFFFFF7FF7F6F
:1049C000F7AECEEEFDFDFDFBFBF9FD3FFFFFFFF770
:1049D000FFFFEEF5FFFFDF7DBFBD7B7F7BFFB67680
:1049E000F6FFEEEFE9E9DDD3D3A3BFA7FF7FFFEF2B
```

Appendix, page 56

```
:1049F000E7FBDFDFBFF797FFFFDB7F5FF77EBEFEE2
:104A0000FDFDFDFF9F9FDDDD37BFBB7B6F7EF7EFB9
:104A10006C737BEBD6F6F6FDFDFD7FF7D8DFBFFBB1
:104A2000FFFFFFF7FFFFBFD7EFEF67DDDDA7DFBFBA
:104A3000FFEFFDBFFFFFFFFFDFFFF7F574EFFFFDA7
:104A40006E7FFFFFFFBFBFBD77FFE7EFFFF7F7FF09
:104A5000FFF5BDBDFB7F7FFBFFFFFFFFEFEFBDDF7E
:104A6000FFFFFAFEFFFFFF6B7FE7FFFEBFDFEF6E8A
:104A7000EFFF6FFF7F7AF7BFBFFDFED17FBFB3B6F9
:104A8000F13BFFFF7FEFEEFEF7DD7DDDDFFDFFFF9A
:104A9000777F7FFFFEFFFBFECFFFBFFFFDFFBEFD69
:104AA000FFFFFF77FFF7CFFFBFBFFF7F3FBFBFFB1A
:104AB000FFDAFB76B5F7EDEDFFEDDFFFFFFFF5F772
:104AC000F7EDEBFB67FFFEEFDFAF9FBF7F7FFF7F61
:104AD000FFE77FF6F6EDEDECDADBFFF93BFBD7DF26
:104AE000BDAFAE7F7D7D5DDFFDBFFFFFDFFFFFFF61
:104AF0007FFFEDEF7FBDDDBFFFFFFFFFEFFF7FFF1C
:104B0000FFFFFFFFFFDFFFFFEFFFFBFFFFDFFFFF09
:104B1000FFFFFFFFFFDFFFFEFDFDFFFFFBFFF7FFD6
:104B2000FFFEEFFFFFFFFFFFFFFBFFFF7FFFFFFEE
:104B30007F7FFFFFFFFFFFBFFFFFFFFDFFFFFFEFD7
:104B4000FFFFF7FDFFEFBFDFDFF7FFBFFFFFFEFFF67
:104B5000FFFFFFFFAFFDFFFDFB7FFFFFFFFFFB5BE5
:104B6000F6FFFFFFFFF3FFFF7FFFEFBFFEFFDFFF5B
:104B7000DDFFFFFFFFFDEFFDFFFBFBFFFEFFFFEF94
:104B8000EF3FEFFFFFFFFF7FFFFFFFFFFFEFFFD20
:104B9000FDFFBFFFFFFFFFFF7FFEFFFFFFFF9DFA5
:104BA000FFFFFFBFFFFFFF7FFFCE7FFFFEFEFEEB9D
:104BB000FFFFFFFF77FFFFFFBEFBFFFF7FFFFFFE9
:104BC000FBFFFFFFFFFFEFFFFFFFFF5FFFFFFFFFA9
:104BD000B7EFFF7FC7FFFFFEEBEFEF0FFDCFBF7F0C
:104BE000FBFFF7FFFFBFFFAD7EFF7EFAFDBFFFFFBC
:104BF000FFFF6DEFFDFFDFFEDFFDFFFFFF7FFFFF2C
:104C0000FFF7FEFFEFFFFFFFFFD3EFFFFFF7FF7F91
:104C1000FFFFFFEFBFFFDFFF3FFBFFFBFFFFEFFFEC
:104C2000EADBFFFF95FFDFFFFFFFFF5F57FFFFBFDF
:104C3000FEFFF8FFFFFDFFFFFBFFFFFF7FF7FFFF1A
:104C4000FFFFC9DCFFFFB3FFBFFFFFFFFFFDFEFFF89
:104C5000FFDFFFFFFDF7FFF77F7FFFFFDFFEFFEFC7
:104C6000FFFFFFFFBFBFFFF77FF7FFEFFFFFFDF85
:104C7000DDFFFFBFFFBFF3BFBFFF7FFAFBFFFFF505
:104C8000FFDDFFFFFFFF6773FEFFFFFFFFFEFEEE8E
:104C9000DFBD3FFFFF7FF6FFE7FF7EFEF9FDFFFF71
:104CA000FFFFFF3FBF97970FAF2F7F7E5E7EEFFD29
:0C4CB000DDDCDCB9FDBFFFFF7FFFFFFF74
:020000020000FC
:104D0000FF0420BAFBEEFF3FBFFFFF5FFCBEFFFFCB
:104D1000B7BDFDFFFAFFFBECF7F7FFBFFFFFE7E7CB
:104D2000F7ED8FD9DDDBFDFDFFAFFEEAF7FFFCBF3E
:104D3000FFF7EFFFDCFFFFFBFF7F3FFF777FFFFF0A
:104D4000F7FBF7F7F7DFDFAFFBF3F7FFFCF57FFECD
:104D5000F9F9F9FB9FFDFFFBF7FBFDDDDFDFE7FE68
:104D6000FEFFFFDFFFFFFFFFEFFFFFF7FFFF77FB18
:104D7000FFFFFFFFD3D7BFFFFFFF7BFFFBFFFFF5F
:104D8000FFF6FDEFEFF7FFFFBFBFBFFEF7EFFFBE80
:104D9000FEDFFDFFFFFFF7BF7FFFFFF7FFFEFF7FFA6
:104DA000FFBEFFFFFFBFFAFDFFBBF7F7F7FE9FFDFC2
:104DB000FFFFFFEFFFFFFFFFCF3BFFFEFFFFBFFE49
:104DC000FFDFFF77777FF7FFFFFFF57EFFFFEB3B0E
:104DD000EB3FFFFFFFDF7FFF7EBF7F7FFDFFDFFFF0F
```

Appendix, page 57

```
:104DE0007FF3FBFFF7FF7EFFEFFFFFFFFFBFDFFFF02
:104DF00073B7FF7BFFFFFFFDFFFFFFBFBFFDFBDBC7
:104E0000FFFFFFDFFFFF7F7FFDFE9DFFFDFDFFFE3C
:104E1000FFFFFFFEFFFEFFCFFFFFEFFEDFDF7F7DFD1A
:104E20005DF7DFFFF7DFBF3FFFF3F6FFBFBFFBFF1D
:104E3000DDFFFFFFFFFFFFDE7FDFFFF7F7F7FFB7DC6
:104E4000FFFFF7EFBFFFFFDFFEDDFFFFFFBF7BFFD1
:104E5000EBFBF7FEEFFAFFEFBFAFFB7FDFFFF6FFE5
:104E6000B6FFFFBFBC9FEEFFFFFFFFBFFFFFFFEFDF
:104E7000FFFEDF77BFAF37FFFFFF5FFAF777EFFC8B
:104E8000C8DBF9D1FFFDE3BF7F77F7FEFEF65FFFDA
:104E9000FFDBDFBDFEBFDFF7FFBFFBBFFFFECFDFE6
:104EA000FFDFFDFFFFFAFDFDFF77DFEFDE9F9CBD1B
:104EB0002FFFDFBFB7FBFEFB7BF6F6F4BCFFFFE97D
:104EC000DFFFFBFAFFF3F7FFFBFF77FFFEFFDFF7E4
:104ED000EFFBFFDFFF3F7BE76F66F6CD6DEDFEFF7B
:104EE000FEFB3ADFD5D6AEADBC7DFFEB5BED9DFFA3
:104EF000FBFFF7FFFFFFF7FFDFEFF9FFAFFEFBF967
:104F0000EFFFFF6777CFFF5FAFFFFFFFFF7D3FFF43
:104F10003BFBFFFF7FFFFFFFFEFFFDFDEFDFEFEC6
:104F2000FDFDFDFFFBEFEBDEFFEFF7EDFFFFFFFF0A
:104F30003BEFF7DAFFF7FFFEFEFEDDFFFBBFF7FFFB
:104F4000DABFFFF777FFFBBFFF7DF8FFFBFEFF7FB8
:104F5000EFFFFDFEEFDDFED5EBFFFF77FF5FF7779D
:104F6000AFFEAF5EFDFFBF9FF7FAFFF3FFF7FFEF66
:104F7000FF7FFFDEFFFFDDBBFFD377BFBFFFFE4D2F
:104F8000ECEFF6F7DFAFDFF737FBFA7FFA77FEFFDC
:104F9000FFFFFF7FFBFFBFBF3F77FFFFBFFF8FDDF9A
:104FA000FFFECFD6A9FFFFFFFFFBFBFE67EEFFECE1D
:104FB000D7FE56EFFFFFDFD7DFD27FEFFFFFBFFF714
:104FC000FFFF99FFEDFF3BEEFFEEFD7F7FFE7DFBD8
:104FD00079DEFFFBFFF7FFBFFFEF7FFFFFDCEFEEA8
:104FE000EEFFDFFDBBFBBF3FF7FDFEFFFDFFFEDF7A
:104FF000FFDBDFBBBFBFFFFFFFFFFFFFDEFFFEE505
:10500000DF9FFF5FFFDFBEBF9EBFEFECEDFDFBF953
:10501000FFF7FFF3FD7EBFFFE7FBCFFFBFFDF7FD0F
:10502000FFFB5F6EFFDC7EFDFD7F73EFDFD7F3F7E5
:10503000E6AFC7DFF6FFFFFFF8FDFFFFFFAFEBF7BF
:10504000FFFF7FF763FF8FFFFFFDFFBBBAFA3FFF54
:10505000FFFFFEFFFFFFFFFFFF7DF7D7B77FFFFEF621
:10506000FE7CEDEFDEEE7FE9EFD3DDD7BFA7AFA784
:105070007FFFEFEFDBDFCFF7AFFFFFEBF3EF3FDFBC
:105080007FFEFEFDCFCEED9FBDDBD9B7B7376FE614
:10509000EFEFEE7C7F5BF3B696D6FD3D2D7D77EF8F
:1050A000FFFFFF5F7EFF6FCBAEBFEFF7BF67FF7FF6
:1050B000CFD6DEDFEFBDEDFDFDFFFBFB7FF7FFF79A
:1050C000EEEFFFFFFFFFFFFFFFBFD7DF3FFF9FBAF
:1050D000EBF3FBF7EFFFBFFBBFBFBFBFFFFFFFFF60
:1050E000FFFFDF5BDFDFFFBFFFF97FF7FBFFB8FFED
:1050F000EFF7FFEFFDDFBFEFFFF7E0FFFFFFEF7F11
:10510000FFFFFFFF3F77FBFFFFF7FFFFFFFF77DFAB
:10511000BDBBBF7F7F7FFF7EFEFE7ACFFFDFFFFF3D
:10512000FFFFFFFFFFFFF77EDEEEFDBDFCFBFB7AF96
:10513000EFBD7B7B7AFAF4F4D4E9E9E9FDDFF9FB12
:10514000FAF5F7F7EDEBEFEFFFD4DFDFBFAF977FB7
:105150006F7FFF6FE7B6F7F7EF6FEFDFDFDEFF3B45
:1051600057DBDBBFBFBF776F735BFD7DFADFEFBF40
:10517000EFFFFFFFBFFCEEFEFBEBF7F777EFEFEF84
:10518000BB7FFFFFFFFFDFFFDFFFFF3DFDFB7BEB93
:10519000EBF77EF7FFFFFFFFDDFDEFBFFBDF7FBFD5B
```

Appendix page 58

```
:1051A000FBFBE9FFF2DFFEFF9DBFDFFFFF6FEFF7C5
:1051B000DBBFDFFFFFBFFEFFFFFF3FFFEFDFFFDFD4
:1051C000EFF7EFF77EFFF56D6BA5DB5BFEFBFFF7FF
:1051D000FDCFBFDDFDFFFFBBF7FFFFDF7FAFFDEDC5
:1051E000DFFFFFBDFFF7BFFEF3BFFFFFBFBFFFFE47
:1051F000FFFFFFDDD7F3FFEEFF67FFFFFBFFFFFEC3
:10520000BFFEBE7DFD75EBFF5FFFB7BFBFFEFD3F7D
:10521000DFFBFFFFFB3FFFFFF7ED7FFFD5EFFFFF5A
:10522000DFF9BFBF7F4F2FD7BEFF7FEFCEF7C4E5BB
:10523000CFE9CA9DFFFDD77BF7E7FBF5DFDFFFFF77
:10524000FF3FDF3BFEBB7FFFFEF7EEEFFFFF9FDF81
:10525000FFFBFFFF7B7EFFF7FFFFEFCEFFEFFFFFD59
:10526000FFFBBFFFFFB7F4FFFFFEFF7FFDDFFFFF88
:10527000BFF7BFFFFFFDFFFBF7FFFFFFFDE7EDEF10
:10528000DFDFFF7FDF7FFFCEFFFDFDFEFFFEFFFFC5
:10529000FFFF7EFFEFEDFFFFFFFFDFDDFFFFF37A94
:1052A0003DFDFFBF7FFFFEFFFF9FB7F7FFFFFBFF47
:1052B000FFFFFEFFFF6EDDD7FFFBFFFFFFF7FF7F66
:1052C000F7AECEEEFDFDFDFBFBF9FD3FFFFFFFF767
:1052D000FFFFEEF5FFFFDF7DBFBD7B7F7BFFB67677
:1052E000F6FFEEEFE9E9DDD3D3A3BFA7FF7FFFEF22
:1052F000E7FBDFDFBFF797FFFFDB7F5FF77EBEFED9
:10530000FDFDFDFF9F9FDDDD37BFBB7B6F7EF7EFB0
:105310006C737BEBD6F6F6FDFDFD7FF7D8DFBFFBA8
:10532000FFFFFFF7FFFFBFD7EFEF67DDDDA7DFBFB1
:10533000FFEFFDBFFFFFFFFFDFFFF7F574EFFFFD9E
:105340006E7FFFFFFFBFBFBD77FFE7EFFFF7F7FF00
:10535000FFF5BDBDFB7F7FFBFFFFFFFFEFEFBDDF75
:10536000FFFFFAFEFFFFFF6B7FE7FFFEBFDFEF6E81
:10537000EFFF6FFF7F7AF7BFBFFDFED17FBFB3B6F0
:10538000F13BFFFF7FEFEEFEF7DD7DDDDFFDFFFF91
:10539000777F7FFFFEFFFBFECFFFBFFFFDFFBEFD60
:1053A000FFFFFF77FFF7CFFFBFBFFF7F3FBFBFFB11
:1053B000FFDAFB76B5F7EDEDFFEDDFFFFFFFF5F769
:1053C000F7EDEBFB67FFFEEFDFAF9FBF7F7FFF7F58
:1053D000FFE77FF6F6EDEDECDADBFFF93BFBD7DF1D
:1053E000BDAFAE7F7D7D5DDFFDBFFFFFDFFFFFFF58
:1053F0007FFFEDEF7FBDDDBFFFFFFFFEFFF7FFF13
:10540000FFFFFFFFFFDFFFFEFFFFBFFFFDFFFFF00
:10541000FFFFFFFFFFDFFFFEFDFDFFFFBFFF7FFCD
:10542000FFFEEFFFFFFFFFFFFFFFBFFFF7FFFFFFE5
:105430007F7FFFFFFFFFFBFFFFFFFDFFFFFFEFCE
:10544000FFFFF7FDFFEFBFDFDFF7FBFFFFFEFFF5E
:10545000FFFFFFFFAFFDFFFDFB7FFFFFFFFFB5BDC
:10546000F6FFFFFFFFF3FFFF7FFFEFBFFEFFDFFF52
:10547000DDFFFFFFFFDEFFDFFFBFBFFEFFFFEF8B
:10548000EF3FEFFFFFFFFFF7FFFFFFFFFFEFFD17
:10549000FDFFBFFFFFFFFFFFFF7FFEFFFFFFF9DF9C
:1054A000FFFFFBFFFFFF7FFFCE7FFFFEFEFEEB94
:1054B000FFFFFFFF77FFFFFFBEFBFFFF7FFFFFFE0
:1054C000FBFFFFFFFFFFEFFFFFFFFF5FFFFFFFFA0
:1054D000B7EFFF7FC7FFFFFEEBEFEF0FFDCFBF7F03
:1054E000FBFFF7FFFFBFFFAD7EFF7EFAFDBFFFFFB3
:1054F000FFFF6DEFFDFFDFFEDFFDFFFFFF7FFFFF23
:10550000FFF7FEFFEFFFFFFFFFD3EFFFFFF7FF7F88
:10551000FFFFFFEFBFFFDFFF3FFBFFBFFFFEFFFE3
:10552000EADBFFFF95FFDFFFFFFFFF5F57FFFFBFD6
:10553000FEFFF8FFFFFDFFFFFBFFFFFF7FF7FFFF11
:10554000FFFFC9DCFFFFB3FFBFFFFFFFFFDFEFFF80
:10555000FFDFFFFFFFDF7FFF77F7FFFFFDFFEFFEFBE
```

Appendix . page 59

```
:10556000FFFFFFFFFBFBFFFF77FF7FFEFFFFFFDF7C
:10557000DDFFFFBFFFBFF3BFBFFF7FFAFBFFFFF5FC
:10558000FFDDFFFFFFFF6773FEFFFFFFFFFEFEEE85
:10559000DFBD3FFFFF7FF6FFE7FF7EFEF9FDFFFF68
:1055A000FFFFFF3FBF97970FAF2F7F7E5E7EEFFD20
:0C55B000DDDCDCB9FDBFFFFF7FFFFFFF6B
:00000001FF
```

What is claimed is:

1. A treatment system for generating, regulating and radiating RF pulses in short bursts to be delivered to a patient, comprising:
- an RF pulse generator;
- an amplifier coupled to the pulse generator;
- a radiating device coupled to the amplifier to radiate RF pulses output by the amplifier;
- at least one input device for a user to input a burst repetition rate and a power level of the RF pulses to be radiated by the radiating device;
- a configurable logic device coupled to the pulse generator comprising a plurality of separately configurable logic elements;
- a memory device for storing a plurality of configuration files, each file when loaded into the configurable logic device causing the configurable logic elements to be configured so that the logic device outputs RF pulses at a pulse repetition rate input by the user;
- a controller coupled to the configurable logic device and memory device which selects the configuration file stored in the memory device to be loaded into the configurable logic device based on a burst repetition rate input by a user; and
- means for controlling the power level of the RF pulses output by system in accordance with the power level input by the user.

* * * * *